United States Patent [19]

Kanamori

[11] Patent Number: 5,576,882
[45] Date of Patent: Nov. 19, 1996

[54] ENDOSCOPE

[75] Inventor: Iwao Kanamori, Kanagawa-ken, Japan

[73] Assignee: Olympus Optical Co., Ltd., Tokyo-to, Japan

[21] Appl. No.: 44,380

[22] Filed: Apr. 7, 1993

[30] Foreign Application Priority Data

Apr. 8, 1992 [JP] Japan .................................... 4-114305

[51] Int. Cl.$^6$ .............................. G02B 23/00; A61B 1/00
[52] U.S. Cl. .......................... 359/434; 359/362; 359/423; 600/160
[58] Field of Search .................................. 359/434–435, 359/708, 710; 128/4, 6; 348/67; 385/33, 117

[56] References Cited

U.S. PATENT DOCUMENTS

| | | | |
|---|---|---|---|
| 4,784,118 | 11/1988 | Fantone et al. | 359/434 |
| 4,916,534 | 4/1990 | Takahashi et al. | 348/67 |
| 5,005,957 | 4/1991 | Kanamori et al. | 359/708 |
| 5,142,410 | 8/1992 | Ono et al. | 359/434 |

FOREIGN PATENT DOCUMENTS

| | | | |
|---|---|---|---|
| 11112 | 11/1989 | European Pat. Off. | 359/434 |
| 339915 | 2/1991 | Japan . | |
| 4146405 | 5/1992 | Japan . | |

*Primary Examiner*—Thong Nguyen
*Attorney, Agent, or Firm*—Cushman, Darby & Cushman

[57] ABSTRACT

An endoscope comprising, in order from the object side, an objective optical system and image relaying optical systems disposed in a number of n, and using, in a (n–1)th or nth image relaying optical system, an optical system for producing positive distortion so as to cancel negative distortion produced by the objective optical system, thereby correcting distortion favorably in the endoscope as a whole.

12 Claims, 18 Drawing Sheets

FIG. 1
PRIOR ART
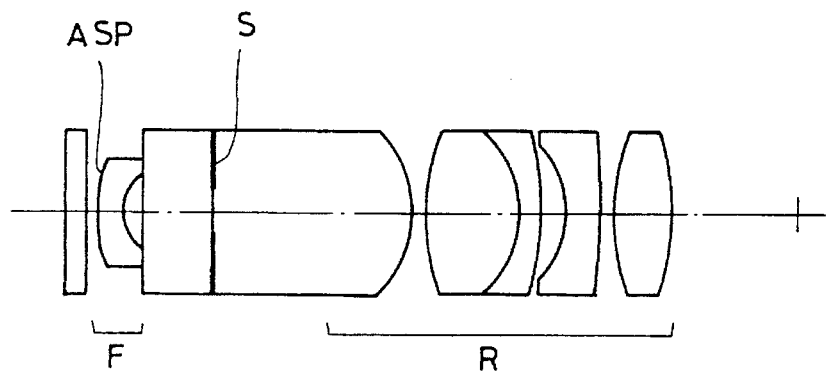
FIG. 2
PRIOR ART
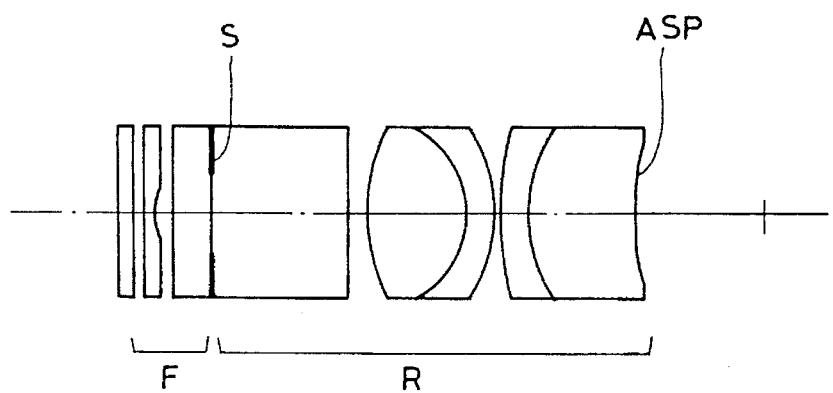
FIG. 5A  FIG. 5B  FIG. 5C  FIG. 5D
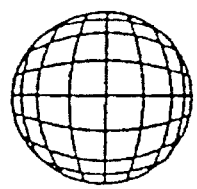 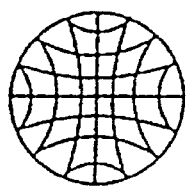 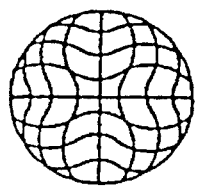 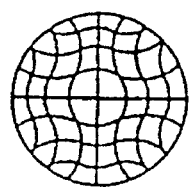

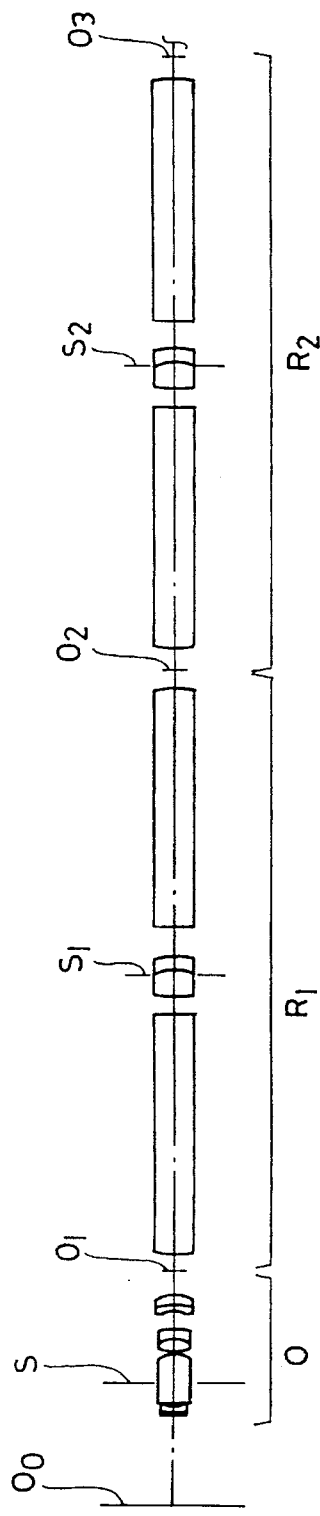
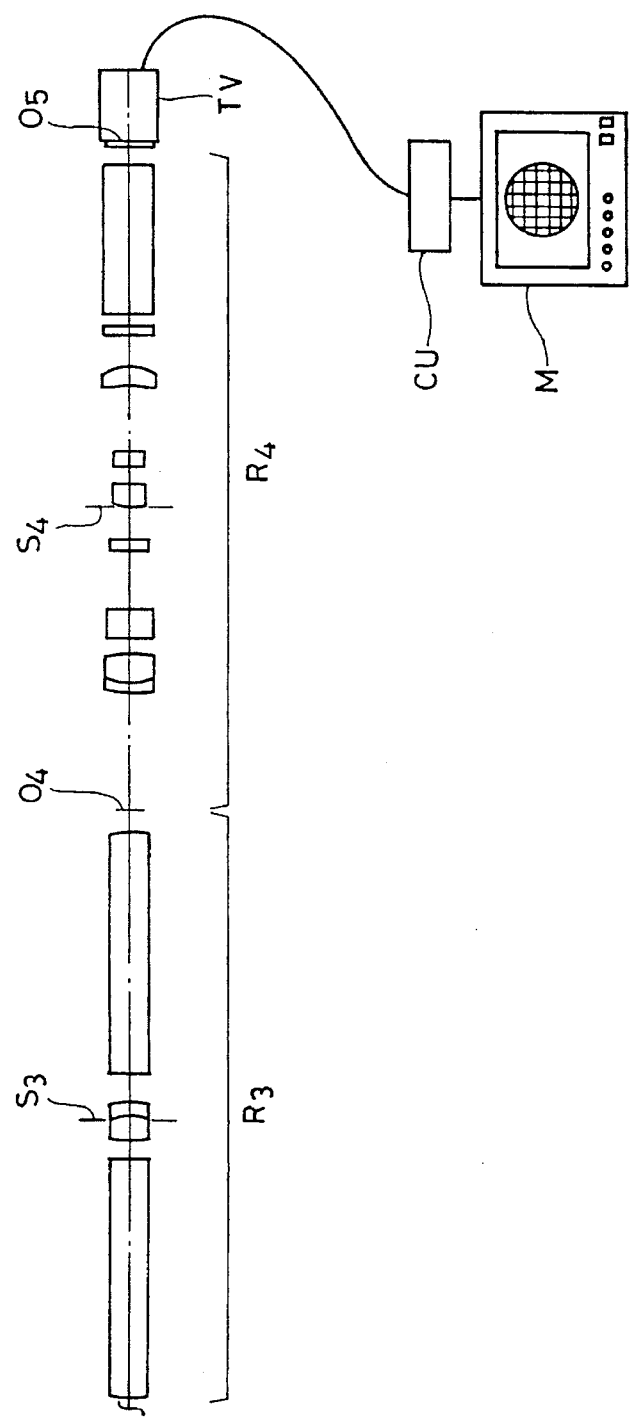
FIG. 6A
FIG. 6B

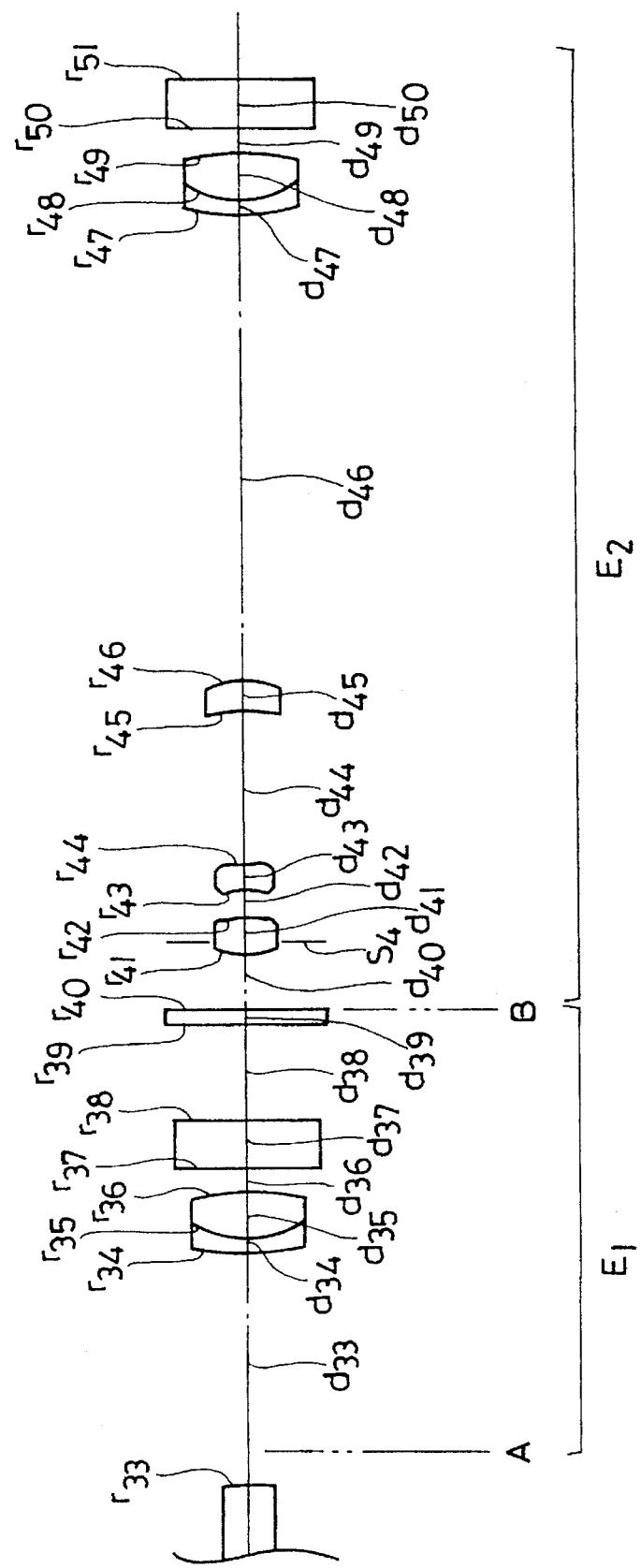

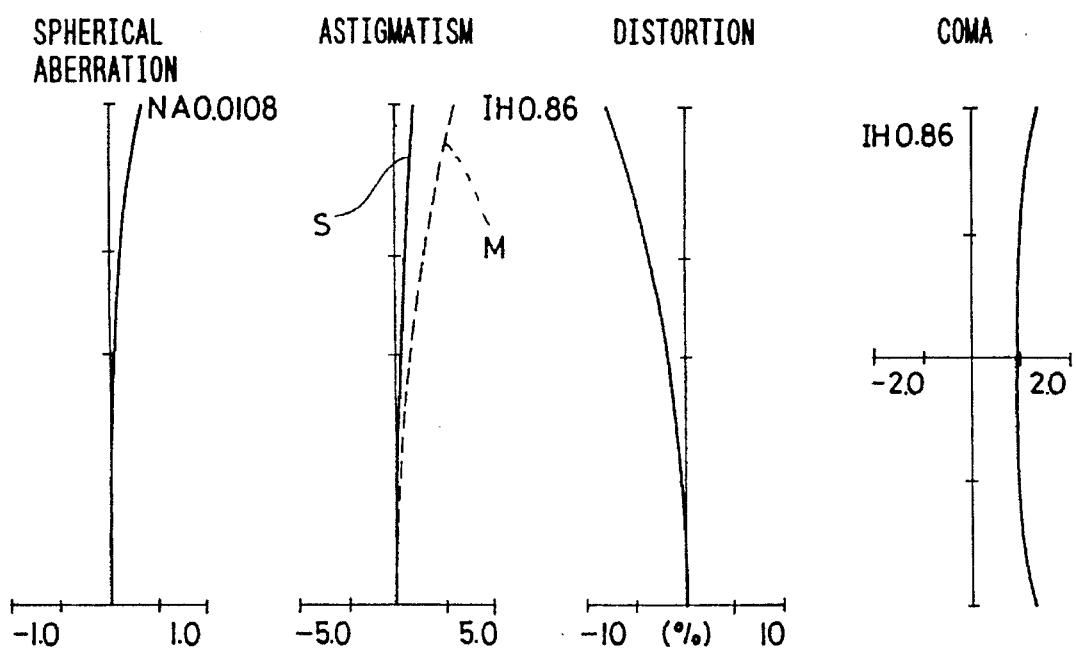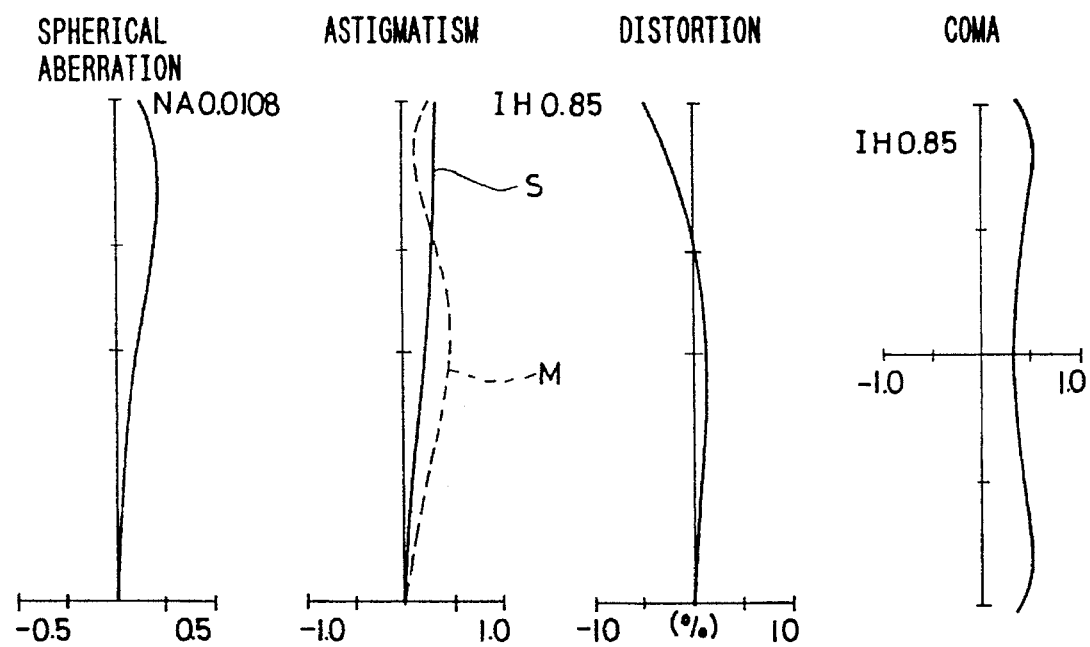

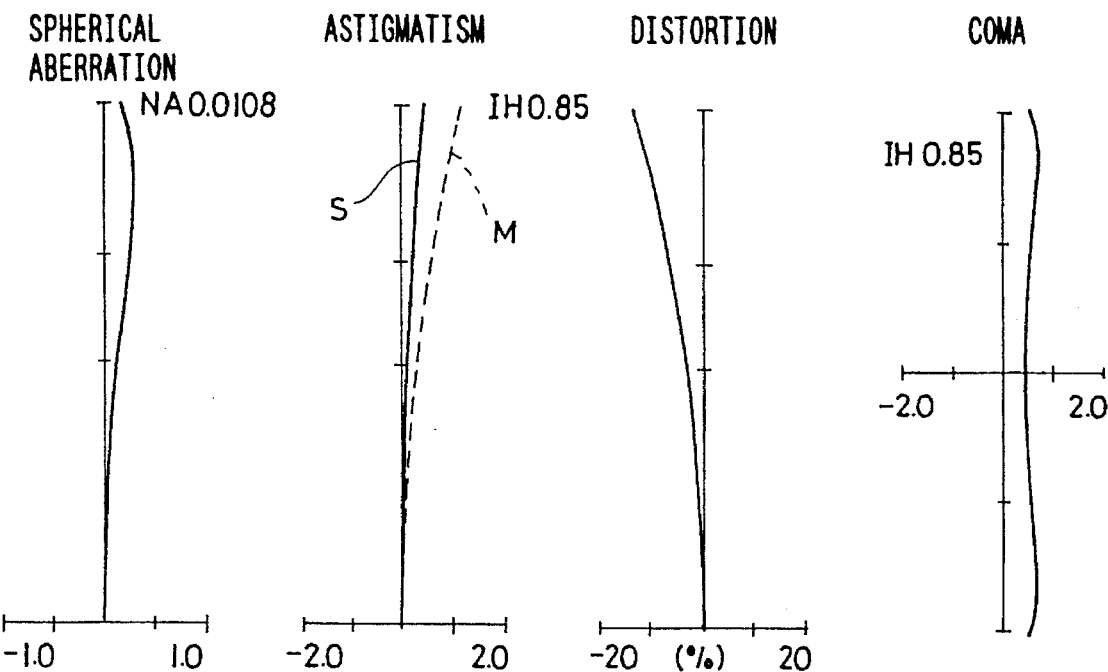
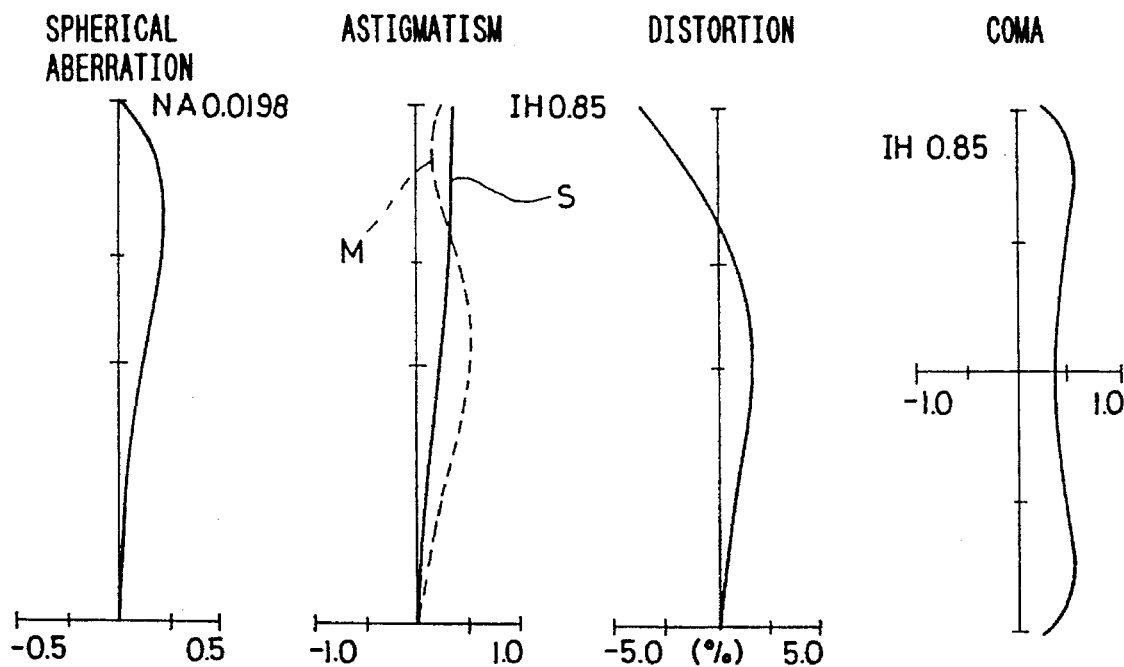

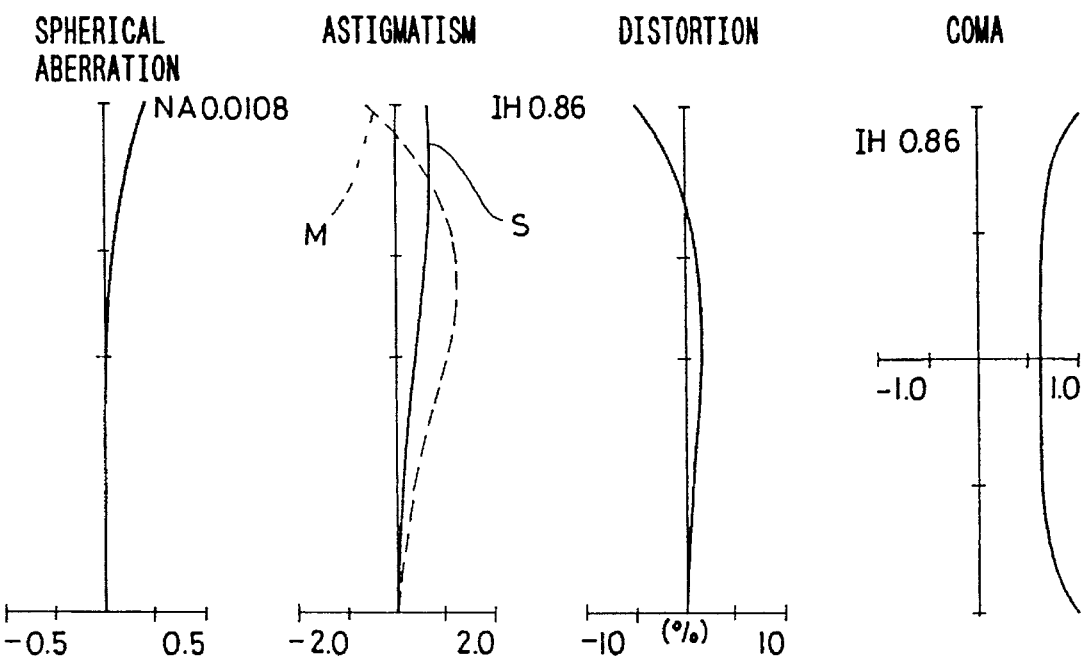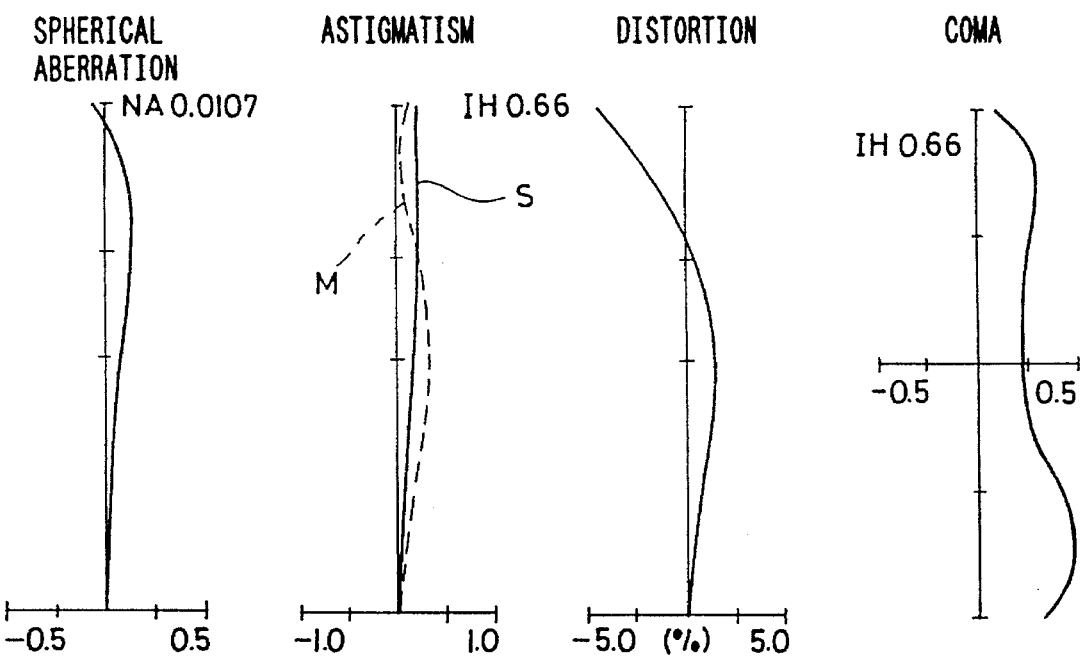

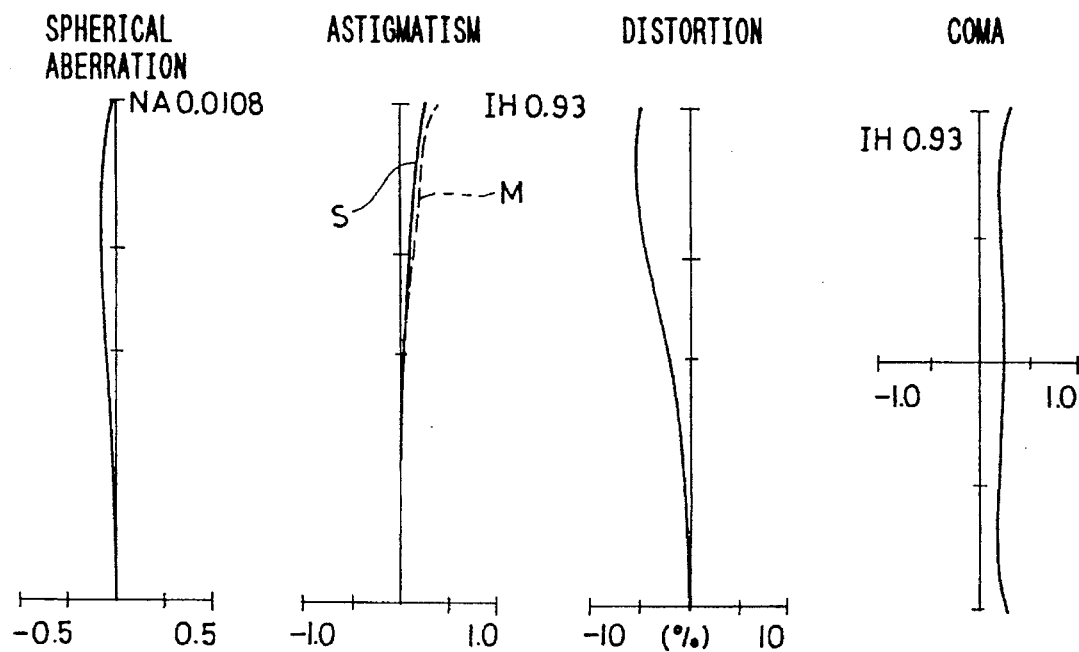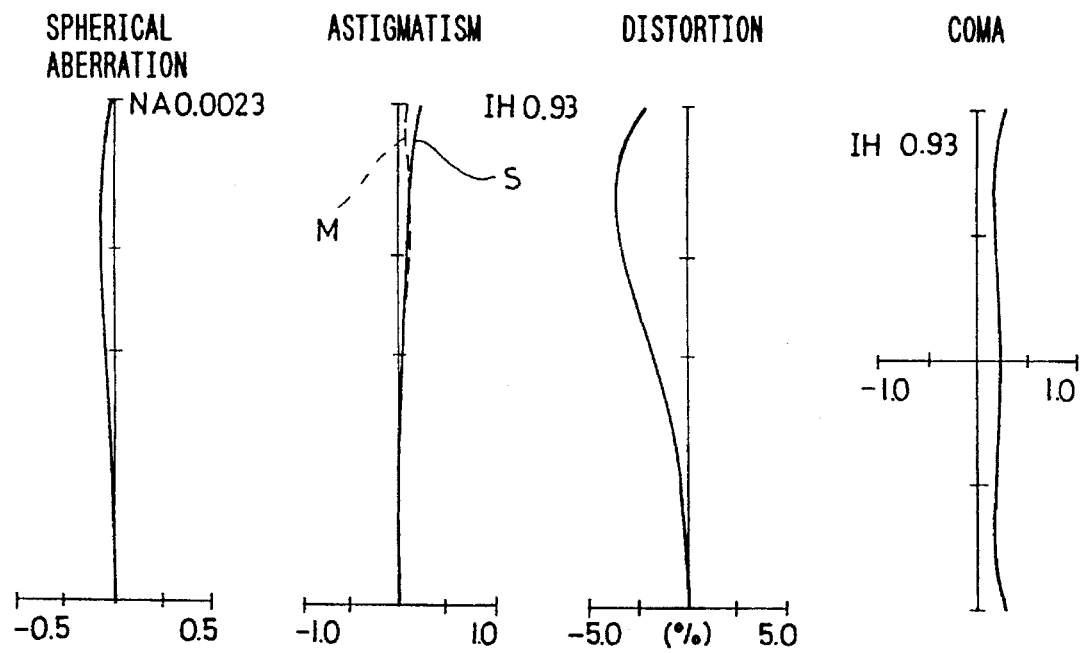

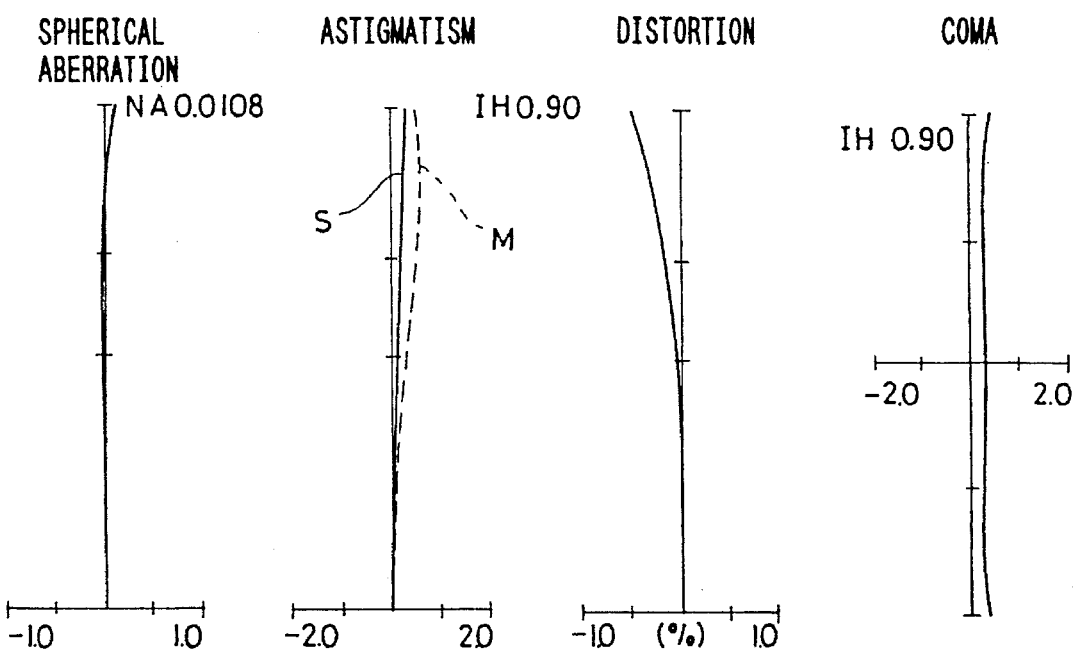
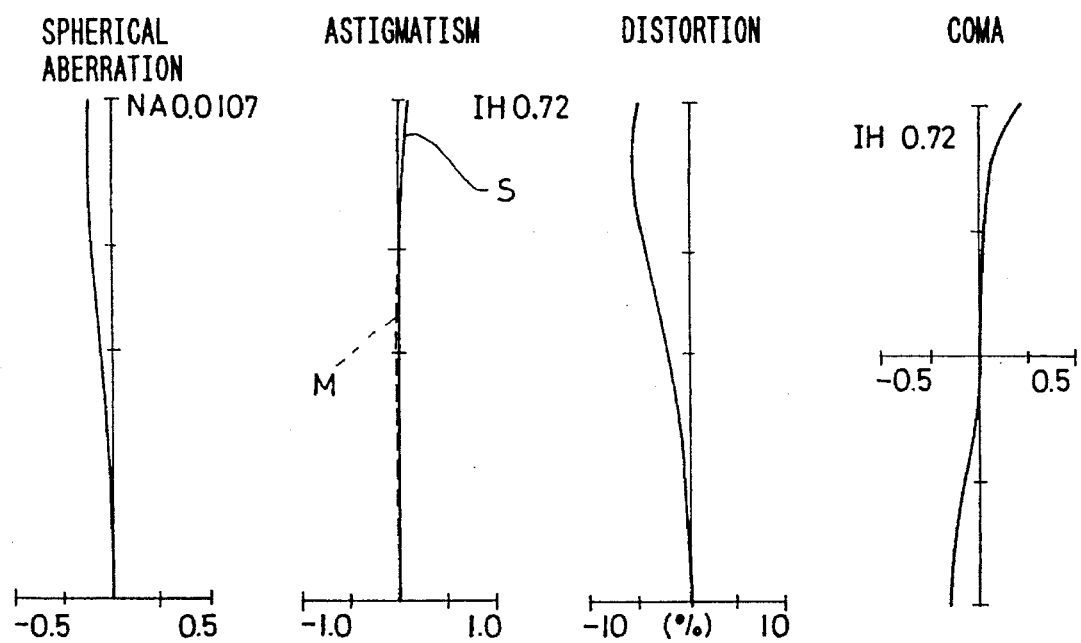

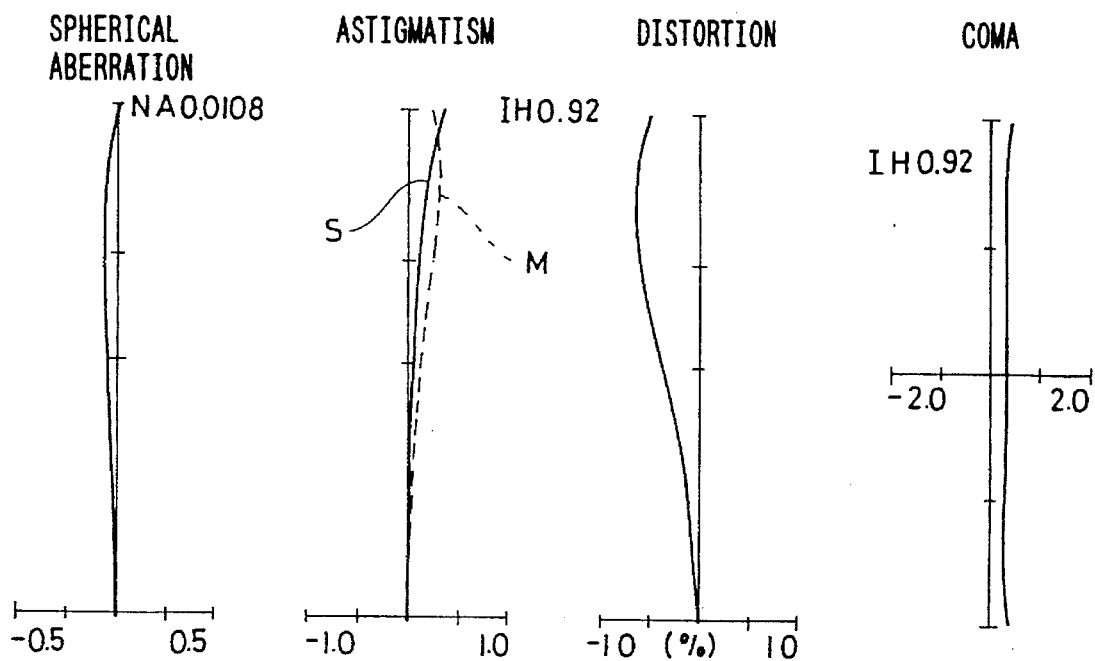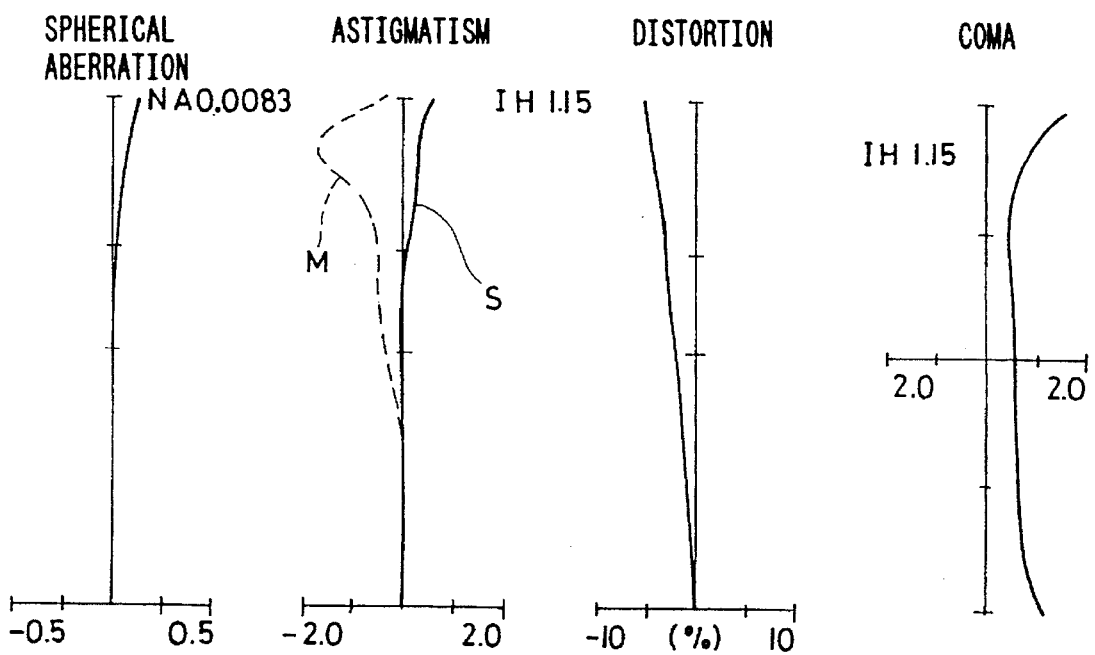

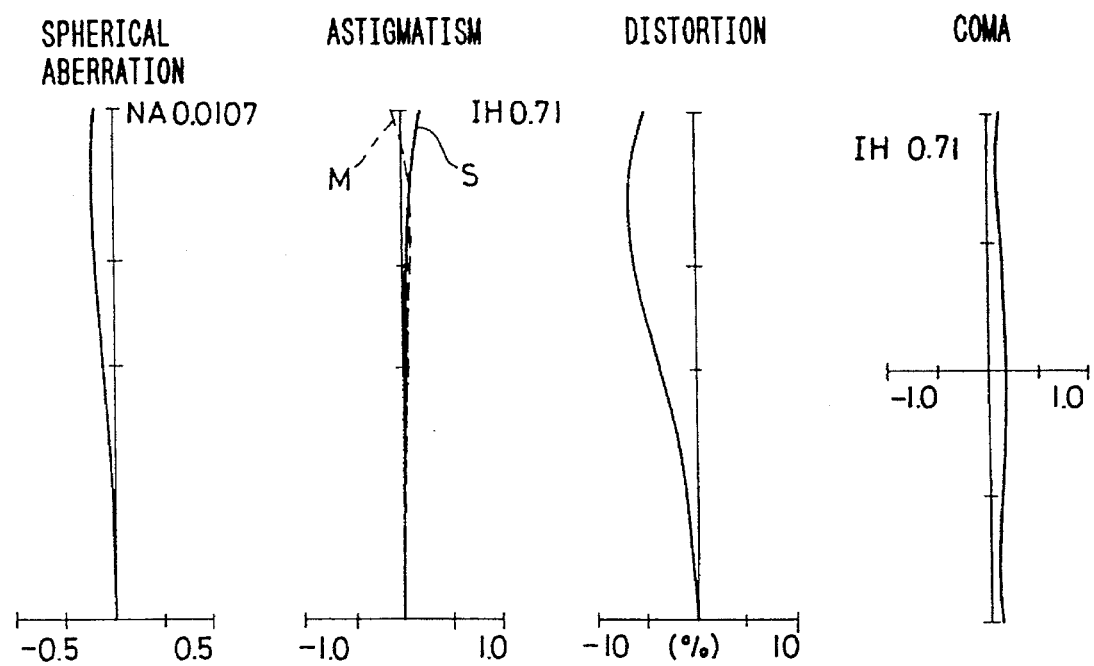
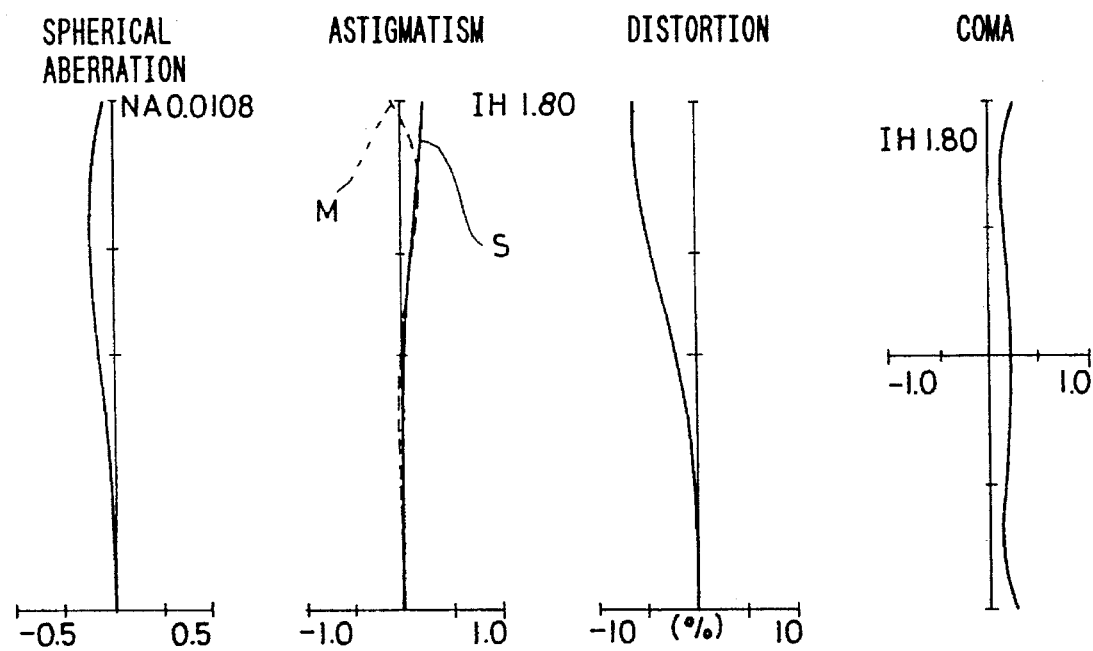

SPHERICAL ABERRATION

ASTIGMATISM

DISTORTION

COMA

ENDOSCOPE

BACKGROUND OF THE INVENTION

1. Field of the Invention

The present invention relates to an endoscope which consists of an objective optical system having favorably corrected aberrations, a plurality of image transmitting optical systems and so on.

2. Description of the Prior Art

Due to the restrictions imposed on an outside diameter and a number of lens elements of an objective optical system for endoscopes, such an optical system is configured as a telecentric type which consists, in order from the object side, of a first negative lens unit, an aperture stop and a second positive lens unit. That is to say, most of objective optical systems for endoscopes have a composition illustrated in FIG. 1 and satisfy the sine condition shown below:

$$I = f \cdot \sin \theta$$

wherein the reference symbol I represents ½ of a film size, or an image height, the reference symbol f designates a focal length of an objective optical system and the reference symbol θ denotes a half of a field angle.

An objective optical system satisfying the sine condition mentioned above produces distortion which is abruptly aggravated as a field angle of the optical system is enlarged. Relationship between distortion DT(θ) produced by the objective optical system and the angle θ thereof is expressed as follows:

$$DT(\theta) = (\cos \theta - 1) \times 100 \, (\%)$$

When a size of an image deformed by distortion is represented by y and a size of an ideal image which is calculated according to the paraxial theory is designated by $y_0$, DT is given by the following formula:

$$DT = (y - y_0)/y_0 \times 100 \, (\%)$$

This distortion is visualized as illustrated in FIG. 3A through FIG. 3F.

The objective optical system for endoscopes which satisfies the sine condition produces negative distortion (barrel type distortion) which is abruptly aggravated as the field angle 2θ is enlarged, for example, in a relation listed in the table shown below:

| Field angle | 2 θ | 40° | 60° | 80° | 100° | 120° | 140° | |
|---|---|---|---|---|---|---|---|---|
| Distortion | DT (θ) | −6 | −13.5 | −23 | −36 | −50 | −66 | (%) |

FIG. 3A through FIG. 3F show views illustrating how images are actually deformed in appearances thereof by distortion. Illustrated in these drawings are images of lattice patterns in air consisting of vertical and horizontal lines arranged at equal intervals on a plane perpendicular to an optical axis which are formed by an objective optical system producing distortion DT(θ) of 30% at a maximum image height.

The conventional objective optical system for endoscopes have, as is understood from the foregoing description, wide field angles, the telecentric type compositions, favorably corrected aberrations, and compact sizes, satisfy the sine condition, and produce remarkable negative distortion.

On images formed by the objective optical systems for endoscopes which produce the negative distortion as described above, marginal portions are small and deformed as compared with central portions. For this reason, these objective optical systems do not permit accurate measurements and analyses of shapes and forms when the optical systems are used, for example in the industrial field, for inspections and observations of objects. Further, these objective optical systems may be causes of erroneous diagnoses when used in the medical field.

As conventional examples of objective optical systems for endoscopes which are configured so as to favorably correct the negative distortion, there are known, for example, the optical systems disclosed by Japanese Patent Kokai Publication No. Hei 3-39,915 and Japanese Patent Kokai Publication No. Hei 4-146,405. These objective optical systems have compositions which are illustrated in FIG. 1 and FIG. 2 respectively. Each of these objective optical systems is of the retrofocus type which consists of a negative front unit F and a positive rear unit R disposed on both sides of an imaginary stop S, and uses an aspherical surface ASP in the front unit F or the rear unit R for correcting distortion.

A portion of an endoscope which is to be inserted into objects to be inspected has a diameter which is restricted dependently on inside diameters and inlet ports of the objects to be inspected. Since objective optical systems for endoscopes are to be disposed in the portion of endoscopes to be inserted into the objects to be inspected, diameters of the objective optical systems are restricted and the objective optical systems are composed generally of lens elements having diameters of 6 mm or smaller. On the other hand, lens elements which have aspherical surfaces are formed by polishing or heating glass materials to high temperature for fusion and molding these glass materials. Regardless of the process to form aspherical lens elements, there is posed a common problem that the aspherical lens elements cannot have design surface precision due to eccentricity caused by positioning errors, ununiform polishing, inadequate molding conditions and so on.

Allowances for eccentricities and surface precision of aspherical lens elements having small outside diameters cannot be loose and allowances which are equal to those for aspherical lens elements or stricter allowances are required for the aspherical lens elements having the small outside diameters. Accordingly, manufacturing becomes more difficult, eccentricity is to be made more easily and surface precision is apt to be lower as aspherical lens elements have smaller outside diameters. Further, allowances for injuries on lens surfaces and adhesion of foreign matters to lens surfaces are stricter for lens elements having small outside diameters than those for lens elements having large outside diameters.

As is understood from the foregoing description, manufacturing of the conventional endoscopes systems which use the aspherical surfaces adopt the aspherical lens elements is difficult and therefore requires a high cost.

In the conventional objective optical system illustrated in FIG. 1, an aspherical surface is used on a meniscus lens element which is disposed on the object side and has a convex surface on the object side. This meniscus lens element has a very strong negative power for obtaining a wide field angle which is indispensable for an objective optical system for endosocpes. For obtaining the very strong negative power of the meniscus lens element, a glass material which has a refractive index as high as possible is selected so that an image side surface of the meniscus lens element will not have a small radius of curvature and the meniscus lens element will be formed easily. Further, the glass material selected for this meniscus lens element has low dispersing power since an offaxial principal ray is high on the meniscus lens element and this lens element produces remarkable chromatic aberration.

It is therefore desirable to use a glass material having a high refractive index and a low dispersing power for a negative meniscus lens element disposed on the object side as in the conventional example of the objective optical system illustrated in FIG. 2. However, the glass material which has such a high refractive index and such low dispersing power has a fusion point on the order of 600° to 700° C. When the aspherical lens element is to be manufactured by molding as described above, it is improper to select the glass material which has the high refractive index and the low dispersing power.

For this reason, a glass material which has a fusion point on the order of 400° to 500° C., a high refractive index and a high dispersing power is selected for the aspherical lens element in the conventional objective optical system illustrated in FIG. 1. As a result, this objective optical system allows remarkable lateral chromatic aberration to be produced by the meniscus lens element which is disposed on the object side. For correcting this chromatic aberration, the objective optical system uses a cemented lens component in the rear unit thereof, requires proper selection of glass materials for lens elements composing the cemented lens component and adopts a small radius of curvature on the cemented surface. As a result, the cemented lens component requires a high manufacturing cost.

For the reasons described above, it is undesirable to use aspherical surfaces in objective optical systems for endoscopes. In addition, when objective optical systems have wide field angles, departures from reference spheres become large, marginal portions of aspherical surfaces have shorter radii of curvature than those of central portions, thereby making it difficult to design and manufacture compact objective optical systems.

SUMMARY OF THE INVENTION

A primary object of the present invention is to provide an endoscope comprising an objective optical system which has favorably corrected aberrations, especially distortion, and is composed of spherical lens elements and an aspherical lens element free from restrictions imposed on glass materials, outside diameters, etc. thereof at design and manufacturing stages.

The endoscope according to the present invention comprises, in order from the object side, an objective optical system, image relaying optical systems disposed in a number of n for consequtively relaying an image formed by the objective optical system, and an image pickup device which receives the image relayed by the image relaying optical systems and functions to convert the image into electrical signals; and is configured so as to reduce distortion in the endoscope as a whole by producing positive distortion with nth or (n−1)th image relaying optical system in an amount nearly equal to that of negative distortion produced by the objective optical system.

BRIEF DESCRIPTION OF THE DRAWINGS

FIG. 1 shows a section view illustrating a composition of the conventional objective lens system for endoscopes:

FIG. 2 shows a sectional view illustrating a composition of another conventional objective lens system for endoscopes;

FIG. 5A, FIG. 5B, FIG. 5C and FIG. 5D show views visualizing differences in image appearances caused by distortion which is produced in different relationship between aspherical surfaces and principal rays;

FIGS. 6A and 6B show sectional views illustrating a composition of a first embodiment of the endoscope according to the present invention;

FIG. 15 shows a sectional view illustrating image relaying optical systems which are used in a sixteenth embodiment of the endoscope according to the present invention;

FIGS. 17A through FIG. 32D show graphs illustrating aberration characteristics of the first through the sixteenth embodiments of the endoscope according to the present invention;

DETAILED DESCRIPTION OF THE PREFERRED EMBODIMENTS

Figures 3A, 3B, 3C:
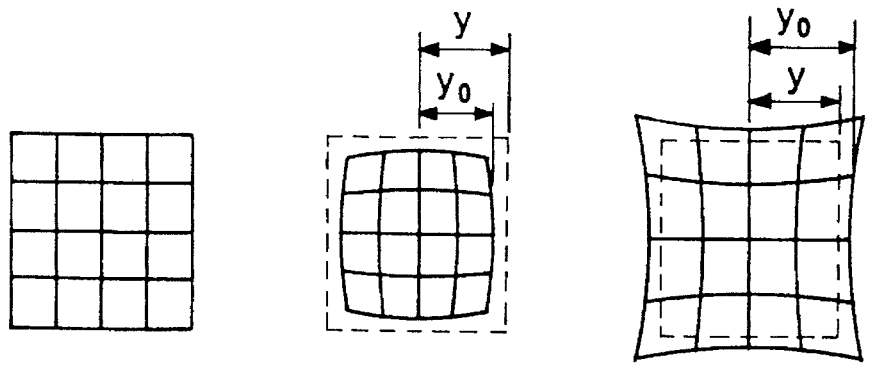
FIG. 3A, FIG. 3B, FIG. 3C, FIG. 3D, FIG. 3E and FIG. 3F show view of an image free from distortion, an image affected by barrel type distortion, an image affected by pin cushion distortion, an image affected by distortion of DT=0, and image effected by distortion of DT<0 and an image affected by distortion of DT<respectively.
Figures 3D, 3E, 3F:
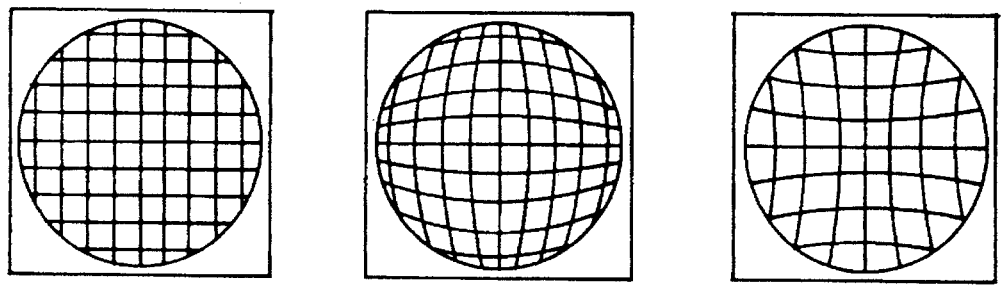
Figure 4:
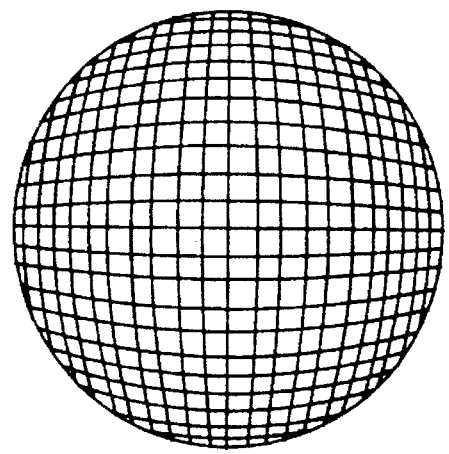
FIG. 4 shows a view illustrating an image formed by an objective lens system for endoscopes producing distortion of DT=−30%.

The endoscope according to the present invention consists, for example as shown in FIGS. 6A and 6B, of an objective optical system $O$, image relaying optical systems $R_1$, $R_2$, $R_3$ and $R_4$, and an eyepiece optical system; and is configured so as to produce positive distortion with the $(n-1)$th image relaying optical system $R_3$ or the nth image relaying optical system $R_4$. Since the image relaying optical system $R_3$ or $R_4$ is not disposed in the portion of the endoscope which is to be inserted into an object to be inspected, no restriction is imposed on an outside diameter, etc. of the image relaying optical system. When an aspherical surface is adopted for producing distortion, for example, the present invention makes it possible to use an aspherical lens element which has a large outside diameter, is rather low in surface precision thereof and allows adhesion of foreign matters in rather a large amount to the surface thereof. Further, the image relaying optical system allows to correct lateral chromatic aberration and other aberrations favorably since no restriction is imposed on a number of the lens elements which are to be disposed in the image relaying optical system.

Further, since nearly no restriction is imposed on the nth or the $(n-1)$th image relaying optical system as described above, it is possible to configure the image relaying optical system so as to produce positive distortion by composing this optical system only of spherical lens elements without using an aspherical lens element.

In order that the negative distortion produced by the objective optical system is cancelled with the positive distortion produced by the image relaying optical system, it is desirable that the following condition (1) is satisfied:
(1) $DT_L/|DT_0|>0.1$
wherein the reference symbol $DT_0$ represents the negative distortion produced at the maximum image height by the objective optical system and the reference symbol $DT_L$ designates the positive distortion produced at the maximum image height by the $(n-1)$th or the nth image relaying optical system. In addition, endoscopes are used in certain cases, for example in the medical field, for observing locations at which liquids exist and media located on the object side of the object side surface of the objective optical system are the liquids in these cases. Distortion is different between a case where air is a medium located on the object side of the objective optical system and another case where a liquid is a medium located on the object side of the objective optical system. In embodiments of the present invention which are to be described later, objective optical systems are designed on an assumption that liquids are media located on the object side of the objective optical systems though descriptions are made taking air as a standard medium. The condition (1) mentioned above is also defined taking air as a medium which is located on the object side of the objective optical system.

If the condition (1) is not satisfied, the image relaying optical system will have a function insufficinet for correcting the distortion and the negative distortion produced by the objective optical system will undesirably remain.

A shape of an aspherical surface which is required for correcting distortion is described, for example, in Japanese Patent Kokai Publication No. Hei 3-39,915. This shape can be outlined as a shape of an aspherical surface which satisfies the following condition:

$$|(K_1 - K_{0.5})/K_{0.5}| < |\cos \omega_1 - \cos \omega_{0.5}|$$

wherein the reference symbols $\omega_1$ and $\omega_{0.5}$ represent field angles at the maximum image height and ½ of the maximum image height respectively, and the reference symbols $K_1$ and $K_{0.5}$ designate values of $K$ given by the formula shown below at an image height of 1 and ½ of the maximum image height respectively.

$$K = \sin \theta_2 / \tan \theta_1$$

wherein the reference symbol $\theta_1$ represents an angle which is formed between the principal ray incident on the aspherical surface and the optical axis, the reference symbol $\theta_2$ designates an angle which is formed between the principal ray refracted by the aspherical surface and the optical axis, and the reference symbol $I$ denotes a value within a range of $I_{max} \geq I \geq I_{max}/2$ when the maximum image height is represented by $I_{max}$.

In order to correct distortion as described above, it is necessary to establish the following relationship between the image height $I$ and an angle of incidence $\theta_1$ on the aspherical surface of the principal ray which is to attain to a point located at the image height $I$:

$$I = f \cdot \tan \theta_1$$

wherein the reference symbol $f$ represents a focal length of the objective optical system as a whole.

On the other hand, there is established the following relationship between an angle of refraction $\theta_2$ and image height on the aspherical surface:

$$I \propto \sin \theta_2$$

For correcting distortion at all image heights, it is necessary that the two formula mentioned above are always satisfied. Therefore, we obtain the following formula:

$$f \cdot \tan \theta_1 \propto \sin \theta_2, \text{ or } \sin \theta_2 / \tan \theta_1 = K \quad (1)$$

Hence, distortion is constant within a range where the formula (1) is satisfied.

Examinations of relationship between variation of a value of $K$ and distortion indicates a fact that positive distortion is produced from axial portion toward marginal portion when $K$ has a larger value, whereas negative distortion is produced when $K$ has a smaller value. Therefore, the following four cases (a), (b), (c) and (d) can be considered when attentions are paid to three points which are located on the optical axis, at the image height of ½ and at the maximum image height, and values of $K$ at these points are represented by $K_0$, $K_{0.5}$ and $K_1$ respectively. Distortion produced in these cases are schematically illustrated in FIG. 5A, FIG. 5B, FIG. 5C and FIG. 5D respectively.

(a) $K_0 > K_{0.5} > K_1$
(b) $K_0 < K_{0.5} < K_1$
(c) $K_0 < K_{0.5} > K_1$
(d) $K_0 > K_{0.5} < K_1$

In case of the conventional optical system for endoscopes, the relations expressed by the following formulae establish:

$$I = f \cdot \sin \theta_1$$

$$l = f_2 \cdot \sin \theta_2$$

wherein the reference symbol $f_2$ represents a focal length of the lens unit disposed after the aperturestop.

Accordingly, comparison with a condition where distortion is corrected, or $\sin \theta_2 / \tan \theta_1 = K$, gives the following formula:

$$\sin \theta_2 / \tan \theta_1 = \cos \theta_1$$

From the formula mentioned above, it will be understood that K has a value which varies at a rate of $\cos \theta_1$. When a value of K in the vicinity of the optical axis is represented by $K_0$, a value of K at the field angle of $\theta_1$ is given as $K_0 \cos \theta_1$. Accordingly, it is sufficient for reducing distortion to satisfy the following condition:

$$|(K_1 - K_0)/K_0| < |\cos \omega_1 - 1|$$

wherein the reference symbol $\omega_1$ represents a field angle at the maximum image height.

Since an objective lens system which satisfies the sine condition is apt to produce distortion which is abruptly aggravated toward the marginal portion of an image, it can be said that the image formed by the objective lens system is deformed by distortion sufficiently little within a range from the optical axis to ½ of the maximum image height. It is therefore important to obtain an effect which is high especially within a region higher than ½ of the maximum image height or reduce distortion within this region. Taking this point into considderation, it is necessary for correcting distortion sufficiently favorably to satisfy the following condition:

$$|(K_1 - K_{0.5})/K_{0.5}| < |\cos \omega_1 - \cos \omega_{0.5}|$$

In a case where an aspherical surface is to be used in the (n−1)th or nth image relaying optical system as a means for producing positive distortion, it is necessary to satisfy at least one of conditions (2) through (5) out of the conditions mentioned below when the aspherical surface is to be disposed in the (n−1)th image relaying optical system or at least one of conditions (6) through (9) out of the following conditions when the aspherical surface is to be disposed in the nth image relaying optical system:

(2) $|AS_{n-1}|/L_{n-1} < 0.3$
(3) $|AS_{n-1}'|/L_{n-1} < 0.65$
(4) $|AS_{n-1}|/L_{n-1} < 0.65$
(5) $|AS_{n-1}'|/L_{n-1} < 0.3$
(6) $|AS_n|/L_n < 0.3$
(7) $|AS_n'|/L_n < 0.65$
(8) $|AS_n|/L_n < 0.65$
(9) $|AS_n'|/L_n < 0.3$

In the conditions (2) through (9) mentioned above, the reference symbol $AS_{n-1}$ represents a distance as measured from an image formed by the (n−2)th image relaying optical system to the aspherical surface when the aspherical surface is located on the incidence side of a pupil of the (n−1)th image relaying optical system, the reference symbol $AS_{n-1}'$ designates a distance as measured from the image formed by the (n−1)th image relaying optical system to the aspherical surface when the aspherical surface is located on the emergence side of the pupil of the (n−1)th image relaying optical system, the reference symbol $AS_n$ denotes a distance as measured from the image formed by the (n−1)th image relaying optical system to the aspherical surface when the aspherical surface is located on the incidence side of a pupil of the nth image relaying optical system, the reference symbol $AS_n'$ represents a distance as measured from the nth image relaying optical system to the aspherical surface, and the reference symbols $L_{n-1}$ and $L_n$ designate distances for which images are to be relayed by the (n−1)th image relaying optical system and the nth image relaying optical system respectively.

When distortion is to be produced by an aspherical lens element, it is necessary to vary curvature from location to location for principal rays having different image heights as described above. When an aspherical lens element is disposed in the vicinity of a pupil, principal rays which are to attain different image heights pass through substantially the same portion of the aspherical surface, thereby making it impossible to select different curvature for the principal rays which are to attain different image heights. It is therefore necessary to dispose the aspherical surface at a location apart from the pupil. When a photoelectric converter element such as a CCD image sensor is used as an image pickup device, however, a wide space must be reserved since it is necessary to dispose an infrared light cutoff filter and an optical low pass filter which functions to eliminate moiré stripes. Since various types of filters are disposed as described above, the image relaying optical system has a pupil which is located on the incidence side or the emergence side of ½ of the image relaying distance thereof and has an asymmetrical composition, thereby making an upper limit and a lower limit of a condition defining a location of the aspherical surface different dependently on the composition of the image relaying optical system.

When the space for disposing the filters is to be reserved on the emergence side of the pupil, the distance as measured from the pupil to the image formed by the (n−2)th image relaying optical system is longer than the distance as measured from the pupil to the image formed by the (n−1)th image relaying optical system in the (n−1)th image relaying optical system. Accordingly, it is sufficient to satisfy the condition (2) when the aspherical surface is to be disposed on the incidence side of the pupil or satisfy the condition (3) when the aspherical surface is to be disposed on the emergence side of the pupil. In other words, a location of the aspherical surface which is selected on the incidence side of the pupil allows a maximum value of the distance to be set as measured from the image to the aspherical surface at a small level so that the aspherical surface is not too close to the pupil.

On the basis of a concept which is similar to that described above, it is necessary that the nth image relaying optical system satisfies the condition (6) or (7).

When the space for disposing the filters is to be reserved on the emergence side of the pupil, the description made above must be reversed. Consequently, the condition (3) or (4) should be satisfied when an aspherical surface is to be disposed in the (n−1)th image relaying optical system, or the condition (8) or (9) should be satisfied when an aspherical surface is to be disposed in the nth image relaying optical system. When plurality of aspherical surfaces are to be adopted, it is sufficient that all or some of the aspherical surfaces satisfy the above-mentioned condition.

In addition, it is desirable to reserve the space for disposing the filters on the emergence side of the pupil so that the filters can be exchanged with others or removed as occasion demands taking into consideration cases where a TV camera, a photographic camera, etc. are used on the emergence side of the nth image relaying optical system.

The aspherical surface described above has a shape which is expressed by the formula shown below and at least one of aspherical surface coefficients E, F, G, H, . . . should desirably be positive:

$$x = \frac{Cy^2}{1 + \sqrt{1 - C^2 y^2}} + Ey^4 + Fy^6 + Gy^8 + Hy^{10}$$

wherein the reference symbols x and y represent values on a coordinate system on which the optical axis is taken as the x axis considering the light receiving side as positive, an intersection between the aspherical surface and the optical axis is taken as an origin, and the direction perpendicular to the x axis is taken as the y axis, the reference symbol C designates an inverse number of a radius of curvature of a circle which is in contact with the aspherical surface in the vicinity of the optical axis, and the reference symbols E, F, G, H, . . . denote the aspherical surface coefficients of the fourth, sixth, eighth, tenth, . . . orders respectively.

The positive aspherical surface coefficients mean that the aspherical surface has a shape which enhances curvature as y has a larger value when the aspherical surface is convex toward the object side or lowers curvature as y has a larger value when the aspherical surface is convex toward the image side. This means that the aspherical surface contributes to produce positive distortion as a field angle is widened or y has a larger value.

FIGS. 6A and 6B illustrates an optical system of the endoscope according to the present invention. An actual endoscope comprises optical elements of an optical system which are accommodated in a housing. An endoscope is roughly divided into an endoscope section comprising the optical elements, etc. disposed within a narrow space and a camera section which is used for photographing images relayed through the endoscope section. It is desirable that the endoscope having the configuration described above is dividable at boundaries (A), (B) and (C) mentioned below:

(A) A boundary located between the (n−2)th image relaying optical system and the (n−1)th image relaying optical system (B) A boundary located in the vicinity of the pupil of the (n−1)th image relaying optical system or the n'th image relaying optical system (C) A boundary between the n'th image relaying optical system and the image pickup device When the dividable endoscope is reattached at the boundary (A) the endoscope section comprises only the objective optical system and the image relaying optical systems, whereas the camera section comprises one or two image relaying optical system(s), the image pickup device and so on. It is desirable to configure the endoscope so as to be dividable at the boundary (A) and design the camera section thereof so as to be combinable with various endoscope sections having different compositions, thereby making it possible to use the expensive camera section commonly with the plurality of endoscope sections. Further, since the camera section comprises an image relaying optical system configured so as to correct distortion, it is possible to maintain favorably corrected distortion regardless of exchange of endoscope sections which are different from one another. Furthermore, it is possible to favorably correct distortion dependently on field angles of the endoscope sections by displacing, along the optical axis, the aspherical surface disposed in the image relaying optical system for correction of distortion in conjunction with the exchange of the endoscope sections.

When the endoscope is configured so as to be dividable at the boundary (B), a light bundle emerging from the endoscope section is a light bundle which is nearly parallel. Accordingly, it is possible to observe an object by naked eyes only with the endoscope section, thereby providing convenience for inspections, diagnoses and taking measures while observing with the naked eyes. In addition, an eyepiece lens system may be attached for observation by naked eyes.

When the endoscope section is to be used as described above, an aspherical surface which is adopted for correcting distortion, or an aspherical surface disposed on the object side of the pupil in the endoscope section makes it possible to observe images little affected by distortion by naked eyes. Further, since a nearly parallel light bundle which emerges from the endoscope section is imaged by the camera section, the camera section can be used as a camera for general endoscopes when the camera section is configured so as to be attachable to eyepiece sections of endoscopes comprising the ordinary eyepiece lenses. In this case an aspherical surface which is disposed in the optical system comprised in the camera section, i.e., an aspherical surface which is disposed on the emergence side of the pupil makes it possible to obtain images with corrected distortion which are to be photographed with the camera section attached to the eyepiece sections of the general endoscopes.

When the endoscope is configured so as to be dividable at the boundary (C), it is possible to obtain a desirable effect that the endoscope permits freely selecting infrared light cutoff filters, low pass filters, image pickup devices, etc., and is compatible with TV cameras having picture elements arranged at high densities and high resolving powers, for example those matched with HDTV system. This configuration is desirable also when the endoscope is equipped with a still camera since this configuration makes it possible to freely select image sizes and special cameras such as those for spectroscopy.

In the next place, the object of the present invention can be accomplished also by cancelling the negative distortion produced by the objective optical system with positive distortion which is produced by an eyepiece optical system. Since the eyepiece optical system is not to be disposed in the portion of the endoscope which is to be inserted into objects to be inspected and free from restrictions imposed on an outside diameter thereof, glass materials to be selected therefor, a number of lens elements to be disposed therein, etc., the eyepiece optical system is suited as a member which is to have a composition producing positive distortion. Speaking concretely, it is desirable for correcting the negative distortion produced by the objective optical system that the eyepiece optical system satisfies the following condition (10):

(10) $|DT_E/DT_0| > 0.1$ wherein the reference symbol $DT_E$ represents a value of positive distortion at the maximum image height which is produced by the n'th image relaying optical system or the eyepiece optical system and the reference symbol $DT_0$ designates a value of the negative distortion which is produced by the objective optical system.

If the condition (10) is not satisfied, the negative distortion will not be corrected sufficiently, or the negative distortion produced by the objective optical system will undesirably remain.

Figure 16:
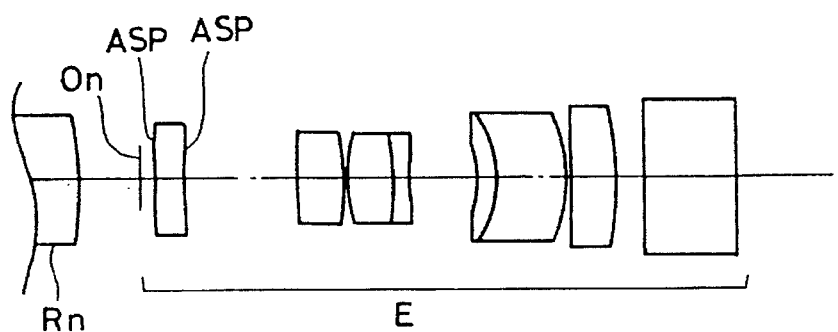
FIG. 16 shows a sectional view illustrating an example of an eyepiece system which is to be used for the endoscope according to the present invention and equipped with a means for correcting distortion.
Figures 17A, 17B, 17C, 17D:
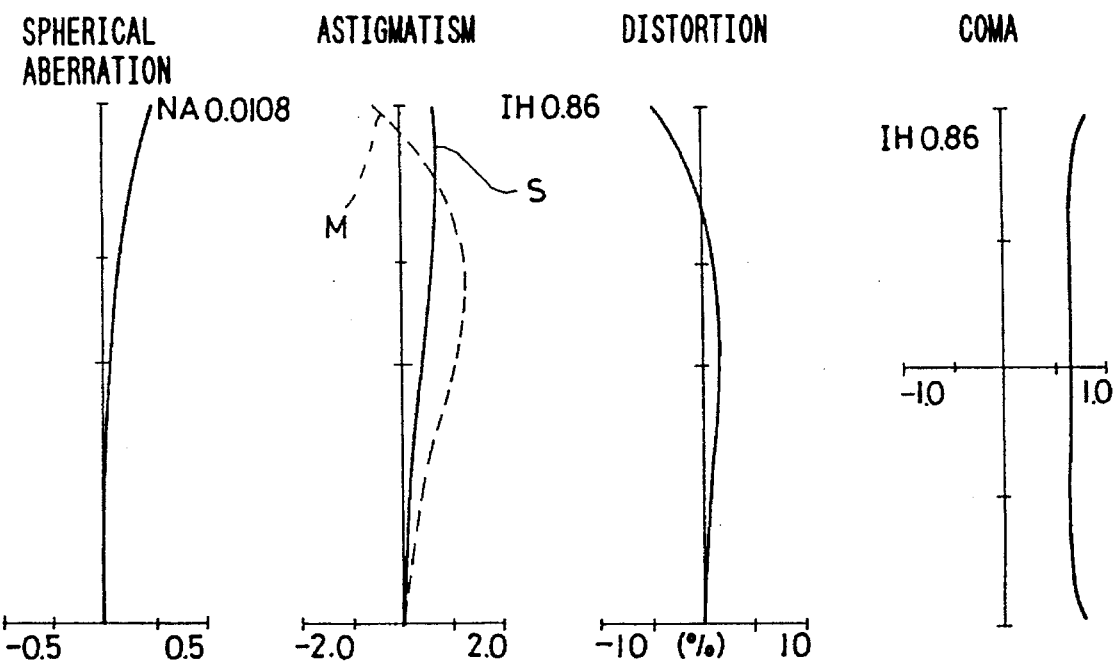
Figure 32A:
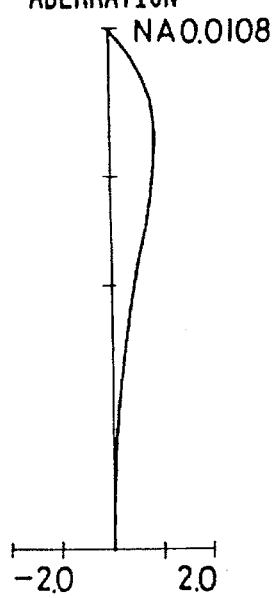
Figure 32B:
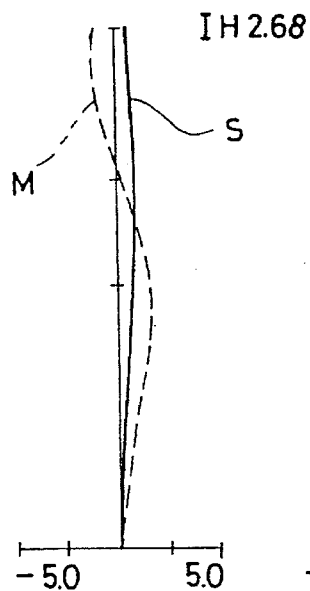
Figure 32C:
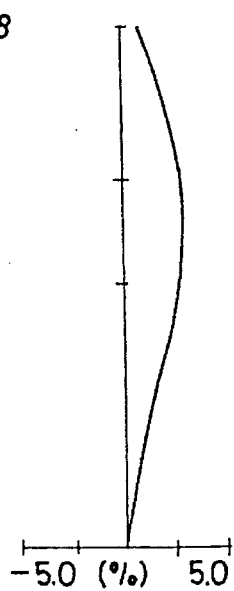
Figure 32D:
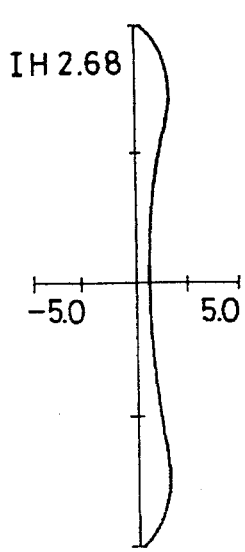

It is desirable to use an aspherical lens element as a means for producing positive distortion in the eyepiece optical system. For example, it is sufficient for this purpose to configure the surface ASP as an aspherical surface in the optical system illustrated in FIG. 16. Further, it is desirable that this aspherical surface satisfies the following condition (11):

(11) $|AS_E|/L_E<0.7$ wherein the reference symbol $AS_E$ represents a distance as measured from an image formed by the n'th image relaying optical system to the aspherical surface disposed in the eyepiece optical system and the reference symbol $L_E$ designates a distance as measured from the image formed by the n'th image relaying optical system to the end surface of incidence of the eyepiece optical system.

If the upper limit of the condition (11) is exceeded, the aspherical surface will undesirably be close to the exit pupil (eye point) and will not contribute to production of distortion.

This aspherical surface has a shape expressed by the above-mentioned formula of aspherical surface in which at least one of E, F, G, H, ... has a positive value and produces positive distortion as y has a larger value.

Further, it is possible to vary an observing magnification in conjunction with diagnosing and inspecting purposes by configuring the image relaying optical system or the eyepiece optical system so as to be attachable and re-attachable or exchangeable with another. Furthermore, certain endoscopes have zooming functions so as to be capable of changing a field angle thereof in the recent days. When an endoscope is capable of changing a field angle thereof, it is possible to observe images always in favorable conditions of aberrations by selectively using, in conjunction with the change of the field angle, eyepiece optical systems which produce distortion in different amounts for cancelling the negative distortion. Moreover, it is possible to observe images in favorably corrected conditions of aberrations regardless of the change of the field angle by configuring the aspherical lens element disposed in the eyepiece optical system so as to produce the positive distortion in variable amounts.

Now, the present invention will be described more detailedly below with reference to the preferred embodiments illustrated in the accompanying drawings and given in the form of the following numerical data:

Embodiment 1

$f = 1.000$, F number $= -13.909$
image height $= 0.8576$, object distance $= -4.0000$
field angle $=$ (in air) 97.3°, (in water) 68.4°
$DT = -4.898$

| | | | |
|---|---|---|---|
| $r_1 = \infty$ | | | |
| | $d_1 = 0.1286$ | $n_1 = 1.76820$ | $v_1 = 71.79$ |
| $r_2 = \infty$ | | | |
| | $d_2 = 0.0858$ | $n_2 = 1.78800$ | $v_2 = 47.43$ |
| $r_3 = 0.2697$ | | | |
| | $d_3 = 0.1286$ | | |
| $r_4 = \infty$ | | | |
| | $d_4 = 0.8789$ | $n_3 = 1.78800$ | $v_3 = 47.43$ |
| $r_5 = \infty$ (stop) | | | |
| | $d_5 = 1.2952$ | $n_4 = 1.78800$ | $v_4 = 47.43$ |
| $r_6 = -1.0459$ | | | |
| | $d_6 = 0.0429$ | | |
| $r_7 = 1.8486$ | | | |
| | $d_7 = 0.6046$ | $n_5 = 1.64000$ | $v_5 = 60.09$ |
| $r_8 = -0.7899$ | | | |
| | $d_8 = 0.4417$ | $n_6 = 1.87666$ | $v_6 = 23.88$ |
| $r_9 = -3.0420$ | | | |
| | $d_9 = 0.7461$ | | |
| $r_{10} = -0.8049$ | | | |
| | $d_{10} = 0.2530$ | $n_7 = 1.72825$ | $v_7 = 28.46$ |
| $r_{11} = -2.9687$ | | | |
| | $d_{11} = 0.4417$ | $n_8 = 1.77250$ | $v_8 = 49.66$ |
| $r_{12} = -1.0459$ | | | |
| | $d_{12} = 1.7581$ | | |
| $r_{13} = 4.8778$ | | | |
| | $d_{13} = 10.2916$ | $n_9 = 1.62004$ | $v_9 = 36.25$ |
| $r_{14} = \infty$ | | | |
| | $d_{14} = 0.7247$ | | |
| $r_{15} = 6.6278$ | | | |
| | $d_{15} = 1.1364$ | $n_{10} = 1.65160$ | $v_{10} = 58.67$ |
| $r_{16} = -1.4974$ | | | |
| | $d_{16} = 0.5789$ | $n_{11} = 1.80610$ | $v_{11} = 40.95$ |
| $r_{17} = -3.3448$ | | | |
| | $d_{17} = 1.2050$ | | |
| $r_{18} = \infty$ | | | |
| | $d_{18} = 10.2916$ | $n_{12} = 1.62004$ | $v_{12} = 36.25$ |
| $r_{19} = -4.8778$ | | | |
| | $d_{19} = 1.7153$ | | |
| $r_{20} = 4.8778$ | | | |
| | $d_{20} = 10.2916$ | $n_{13} = 1.62004$ | $v_{13} = 36.25$ |
| $r_{21} = \infty$ | | | |
| | $d_{21} = 0.7247$ | | |
| $r_{22} = 6.6278$ | | | |
| | $d_{22} = 1.1364$ | $n_{14} = 1.65160$ | $v_{14} = 58.67$ |
| $r_{23} = -1.4974$ | | | |
| | $d_{23} = 0.5789$ | $n_{15} = 1.80610$ | $v_{15} = 40.95$ |

-continued

Embodiment 1

| | | | |
|---|---|---|---|
| $r_{24} = -3.3448$ | | | |
| | $d_{24} = 1.2050$ | | |
| $r_{25} = \infty$ | | | |
| | $d_{25} = 10.2916$ | $n_{16} = 1.62004$ | $v_{16} = 36.25$ |
| $r_{26} = -4.8778$ | | | |
| | $d_{26} = 1.7153$ | | |
| $r_{27} = 4.8778$ | | | |
| | $d_{27} = 10.2916$ | $n_{17} = 1.62004$ | $v_{17} = 36.25$ |
| $r_{28} = \infty$ | | | |
| | $d_{28} = 0.7247$ | | |
| $r_{29} = 6.6278$ | | | |
| | $d_{29} = 1.1364$ | $n_{18} = 1.65160$ | $v_{18} = 58.67$ |
| $r_{30} = -1.4974$ | | | |
| | $d_{30} = 0.5789$ | $n_{19} = 1.80610$ | $v_{19} = 40.95$ |
| $r_{31} = -3.3448$ | | | |
| | $d_{31} = 1.2050$ | | |
| $r_{32} = \infty$ | | | |
| | $d_{32} = 10.2916$ | $n_{20} = 1.62004$ | $v_{20} = 36.25$ |
| $r_{33} = -4.8778$ | | | |
| | $d_{33} = 6.0918$ | | |
| $r_{34} = 6.6025$ | | | |
| | $d_{34} = 0.3859$ | $n_{21} = 1.78472$ | $v_{21} = 25.71$ |
| $r_{35} = 2.4884$ | | | |
| | $d_{35} = 1.2436$ | $n_{22} = 1.67003$ | $v_2 = 47.25$ |
| $r_{36} = -6.3714$ | | | |
| | $d_{36} = 0.6432$ | | |
| $r_{37} = \infty$ | | | |
| | $d_{37} = 1.2864$ | $n_{23} = 1.76820$ | $v_{23} = 71.79$ |
| $r_{38} = \infty$ | | | |
| | $d_{38} = 2.4828$ | | |
| $r_{39} = \infty$ | | | |
| | $d_{39} = 0.4288$ | $n_{24} = 1.51633$ | $v_{24} = 64.15$ |
| $r_{40} = \infty$ | | | |
| | $d_{40} = 1.4028$ | | |
| $r_{41} = 2.0100$ | | | |
| | $d_{41} = 0.9734$ | $n_{25} = 1.71300$ | $v_{25} = 53.84$ |
| $r_{42} = 93.5986$ | | | |
| | $d_{42} = 0.7633$ | | |
| $r_{43} = -1.5500$ | | | |
| | $d_{43} = 0.6304$ | $n_{26} = 1.75520$ | $v_{26} = 27.51$ |
| $r_{44} = 3.4848$ | | | |
| | $d_{44} = 2.7805$ | | |
| $r_{45} = -2.3612$ (aspherical surface) | | | |
| | $d_{45} = 0.8148$ | $n_{27} = 1.59270$ | $v_{27} = 35.29$ |
| $r_{46} = -1.5051$ (aspherical surface) | | | |
| | $d_{46} = 1.3417$ | | |
| $r_{47} = \infty$ | | | |
| | $d_{47} = 0.4288$ | $n_{28} = 1.51633$ | $v_{28} = 64.15$ |
| $r_{48} = \infty$ | | | |
| | $d_{48} = 0.4288$ | | |
| $r_{49} = \infty$ | | | |
| | $d_{49} = 6.4322$ | $n_{29} = 1.54869$ | $v_{29} = 45.55$ |
| $r_{50} = \infty$ | | | |
| | $d_{50} = 0.8576$ | | |
| $r_{51} = \infty$ | | | |
| | $d_{51} = 0.1715$ | $n_{30} = 1.51633$ | $v_{30} = 64.15$ |
| $r_{52} = \infty$ | | | | aspherical surface coefficients (45th surface) $P = 1.0000, E = 0.12532$
$F = -0.4305, \times 10^{-4}, G = -0.12993 \times 10^{-8}$ (46th surface) $P = 1.0000, E = 0.10675$
$F = 0.88372 \times 10^{-4}, G = 0.34025 \times 10^{-8}$ $DT_L = 8.39$, $DT_0 = -31.72$, $|DT_L/DT_0| = 0.265$
$AS_4 = 10.48$, $L_4 = 28.72$, $|AS_4|/L_4 = 0.365$

Embodiment 3

$f = 1.000$, F number $= -13.824$
image height $= 0.8522$, object distance $= -4.0000$
$SK = 0.093$, field angle = (in air) 95°
(in water) 68.4°, $DT = -4.918$
$r_1 = \infty$ -continued Embodiment 3

| | | | |
|---|---|---|---|
| $r_2 = \infty$ | $d_1 = 0.1278$ | $n_1 = 1.76820$ | $v_1 = 71.79$ |
| $r_3 = 0.2680$ | $d_2 = 0.0852$ | $n_2 = 1.78800$ | $v_2 = 47.43$ |
| $r_4 = \infty$ | $d_3 = 0.1278$ | | |
| $r_5 = \infty$ (stop) | $d_4 = 0.8435$ | $n_3 = 1.78800$ | $v_3 = 47.43$ |
| $r_6 = -1.0392$ | $d_5 = 1.2869$ | $n_4 = 1.78800$ | $v_4 = 47.43$ |
| $r_7 = 1.8368$ | $d_6 = 0.0426$ | | |
| $r_8 = -0.7848$ | $d_7 = 0.6008$ | $n_5 = 1.64000$ | $v_5 = 60.09$ |
| $r_9 = -3.0226$ | $d_8 = 0.4389$ | $n_6 = 1.84666$ | $v_6 = 23.88$ |
| $r_{10} = -0.7997$ | $d_9 = 0.7414$ | | |
| $r_1 = -2.9497$ | $d_{10} = 0.2514$ | $n_7 = 1.72825$ | $v_7 = 28.46$ |
| $r_{12} = -1.0392$ | $d_{11} = 0.4389$ | $n_8 = 1.77250$ | $v_8 = 49.66$ |
| $r_{13} = 4.8466$ | $d_{12} = 1.7469$ | | |
| $r_{14} = \infty$ | $d_{13} = 10.2258$ | $n_9 = 1.62004$ | $v_9 = 36.25$ |
| $r_{15} = 6.5854$ | $d_{14} = 0.7201$ | | |
| $r_{16} = -1.4879$ | $d_{15} = 1.1291$ | $n_{10} = 1.65160$ | $v_{10} = 58.67$ |
| $r_{17} = -3.3234$ | $d_{16} = 0.5752$ | $n_{11} = 1.80610$ | $v_{11} = 40.95$ |
| $r_{18} = \infty$ | $d_{17} = 1.1973$ | | |
| $r_{19} = -4.8466$ | $d_{18} = 10.2258$ | $n_{12} = 1.62004$ | $v_{12} = 36.25$ |
| $r_{20} = 4.8466$ | $d_{19} = 1.7043$ | | |
| $r_{21} = \infty$ | $d_{20} = 10.2258$ | $n_{13} = 1.62004$ | $v_{13} = 36.25$ |
| $r_{22} = 6.5854$ | $d_{21} = 0.7201$ | | |
| $r_{23} = -1.4879$ | $d_{22} = 1.1291$ | $n_{14} = 1.65160$ | $v_{14} = 58.67$ |
| $r_{24} = -3.3234$ | $d_{23} = 0.5752$ | $n_{15} = 1.80610$ | $v_{15} = 40.95$ |
| $r_{25} = \infty$ | $d_{24} = 1.1973$ | | |
| $r_{26} = -4.8466$ | $d_{25} = 10.2258$ | $n_{16} = 1.62004$ | $v_{16} = 36.25$ |
| $r_{27} = 4.8466$ | $d_{26} = 1.7043$ | | |
| $r_{28} = \infty$ | $d_{27} = 10.2258$ | $n_{17} = 1.62004$ | $v_{17} = 36.25$ |
| $r_{29} = 6.5854$ | $d_{28} = 0.7201$ | | |
| $r_{30} = -1.4879$ | $d_{29} = 1.1291$ | $n_{18} = 1.65160$ | $v_{18} = 58.67$ |
| $r_{31} = -3.3234$ | $d_{30} = 0.5752$ | $n_{19} = 1.80610$ | $v_{19} = 40.95$ |
| $r_{32} = \infty$ | $d_{31} = 1.1973$ | | |
| $r_{33} = -4.8466$ | $d_{32} = 10.2258$ | $n_{20} = 1.62004$ | $v_{20} = 36.25$ |
| $r_{34} = 6.5603$ | $d_3 = 6.0528$ | | |
| $r_{35} = 2.4725$ | $d_{34} = 0.3835$ | $n_{21} = 1.78472$ | $v_{21} = 25.71$ |
| $r_{36} = -6.306$ | $d_{35} = 1.2356$ | $n_{22} = 1.67003$ | $v_{22} = 47.25$ |
| $r_{37} = \infty$ | $d_{36} = 0.6391$ | | |
| $r_{38} = \infty$ | $d_{37} = 1.2782$ | $n_{23} = 1.76820$ | $v_{23} = 71.79$ |
| $r_{39} = \infty$ | $d_{38} = 2.4670$ | | |
| $r_{40} = \infty$ | $d_{39} = 0.4261$ | $n_{24} = 1.51633$ | $v_{24} = 64.15$ |

-continued

Embodiment 3

| | | | |
|---|---|---|---|
| $r_{41} = 3.2180$ (aspherical surface) | $d_{40} = 1.4004$ | | |
| | $d_{41} = 0.9672$ | $n_{25} = 1.71300$ | $v_{25} = 53.84$ |
| $r_{42} = -3.3627$ (aspherical surface) | | | |
| | $d_{42} = 0.7584$ | | |
| $r_{43} = -1.3483$ | | | |
| | $d_{43} = 0.6263$ | $n_{26} = 1.75520$ | $v_{26} = 27.51$ |
| $r_{44} = 4.2396$ (aspherical surface) | | | |
| | $d_{44} = 4.0020$ | | |
| $r_{45} = -2.35643$ (aspherical surface) | | | |
| | $d_{45} = 0.8095$ | $n_{27} = 1.59270$ | $v_{27} = 35.29$ |
| $r_{46} = -1.5753$ (aspherical surface) | | | |
| | $d_{46} = 1.3265$ | | |
| $r_{47} = \infty$ | | | |
| | $d_{47} = 0.4261$ | $n_{28} = 1.51633$ | $v_{28} = 64.15$ |
| $r_{48} = \infty$ | | | |
| | $d_{48} = 0.4261$ | | |
| $r_{49} = \infty$ | | | |
| | $d_{49} = 6.3911$ | $n_{29} = 1.54869$ | $v_{29} = 45.55$ |
| $r_{50} = \infty$ | | | |
| | $d_{50} = 0.8522$ | | |
| $r_{51} = \infty$ | | | |
| | $d_{51} = 0.1704$ | $n_{30} = 1.51633$ | $v_{30} = 64.15$ |
| $r_{52} = \infty$ | | | | aspherical surface coefficients

| | |
|---|---|
| (41th surface) | $P = 1.0000$, $E = -0.15335 \times 10^{-1}$, $F = 0.29323 \times 10^{-1}$, $G = 0.43862$ |
| (42th surface) | $P = 1.0000$, $E = -0.27106 \times 10^{-2}$, $F = 0.10501$, $G = 0.61813$ |
| (44th syrface) | $P = 1.0000$, $E = -0.31304 \times 10^{-1}$, $F = -0.29503$, $G = -0.21036 \times 10$ |
| (45th surface) | $P = 1.0000$, $E = 0.13137$, $F = -0.31858 \times 10^{-2}$, $G = -0.13989 \times 10^{-1}$ |
| (46th surface) | $P = 1.0000$, $E = 0.10108$, $F = 0.47117 \times 10^{-2}$, $G = 0.71273 \times 10^{-2}$ |

$DT_L = 8.48$, $DT_0 = -31.72$, $|DT_L/DT_0| = 0.267$
$AS_4 = 14.40$, $L_4 = 29.77$, $|AS_4|/L_4 = 0.484$

Embodiment 6

$f = 1.000$, F number $= -13.037$,
image height $= 0.8584$, object distance $= -4.3000$
field angle $=$ (in air) 95°, (in water) 68.4°
$DT = -5.003$

| | | | |
|---|---|---|---|
| $r_1 = \infty$ | | | |
| | $d_1 = 0.1288$ | $n_1 = 1.76820$ | $v_1 = 71.79$ |
| $r_2 = \infty$ | | | |
| | $d_2 = 0.0858$ | $n_2 = 1.78800$ | $v_2 = 47.43$ |
| $r_3 = 0.2700$ | | | |
| | $d_3 = 0.1288$ | | |
| $r_4 = \infty$ | | | |
| | $d_4 = 0.8496$ | $n_3 = 1.78800$ | $v_3 = 47.43$ |
| $r_5 = \infty$ (stop) | | | |
| | $d_5 = 1.2963$ | $n_4 = 1.78800$ | $v_4 = 47.43$ |
| $r_6 = -1.0468$ | | | |
| | $d_6 = 0.0429$ | | |
| $r_7 = 1.8502$ | | | |
| | $d_7 = 0.6052$ | $n_5 = 1.64000$ | $v_5 = 60.09$ |
| $r_8 = -0.7906$ | | | |
| | $d_8 = 0.4421$ | $n_6 = 1.84666$ | $v_6 = 23.88$ |
| $r_9 = -3.0446$ | | | |
| | $d_9 = 0.7468$ | | |
| $r_{10} = -0.8056$ | | | |
| | $d_{10} = 0.2532$ | $n_7 = 1.72825$ | $v_7 = 28.46$ |
| $r_{11} = -2.9712$ | | | |
| | $d_{11} = 0.4421$ | $n_8 = 1.77250$ | $v_8 = 49.66$ |
| $r_{12} = -1.0468$ | | | |
| | $d_{12} = 1.7597$ | | |
| $r_{13} = 4.8820$ | | | |
| | $d_{13} = 10.3004$ | $n_9 = 1.62004$ | $v_9 = 36.25$ |
| $r_{14} = \infty$ | | | |

-continued

Embodiment 6

| | | | |
|---|---|---|---|
| | $d_{14} = 0.7253$ | | |
| $r_{15} = 6.6335$ | $d_{15} = 1.1373$ | $n_{10} = 1.65160$ | $v_{10} = 58.67$ |
| $r_{16} = -1.4987$ | $d_{16} = 0.5794$ | $n_{11} = 1.80610$ | $v_{11} = 40.95$ |
| $r_{17} = -3.3476$ | $d_{17} = 1.2060$ | | |
| $r_{18} = \infty$ | $d_{18} = 10.3004$ | $n_{12} = 1.62004$ | $v_{12} = 36.25$ |
| $r_{19} = -4.8820$ | $d_{19} = 1.7167$ | | |
| $r_{20} = 4.8820$ | $d_{20} = 10.3004$ | $n_{13} = 1.62004$ | $v_{13} = 36.25$ |
| $r_{21} = \infty$ | $d_{21} = 0.7253$ | | |
| $r_{22} = 6.6335$ | $d_{22} = 1.1373$ | $n_{14} = 1.65160$ | $v_{14} = 58.67$ |
| $r_{23} = -1.4987$ | $d_{23} = 0.5794$ | $n_{15} = 1.80610$ | $v_{15} = 40.95$ |
| $r_{24} = -3.3476$ | $d_{24} = 1.2060$ | | |
| $r_{25} = \infty$ | $d_{25} = 10.3004$ | $n_{16} = 1.62004$ | $v_{16} = 36.25$ |
| $r_{26} = -4.8820$ | $d_{26} = 1.7167$ | | |
| $r_{27} = 4.8820$ | $d_{27} = 10.3004$ | $n_{17} = 1.62004$ | $v_{17} = 36.25$ |
| $r_{28} = \infty$ | $d_{28} = 0.7253$ | | |
| $r_{29} = 6.6335$ | $d_{29} = 1.1373$ | $n_{18} = 1.65160$ | $v_{18} = 58.67$ |
| $r_{30} = -1.4987$ | $d_{30} = 0.5794$ | $n_{19} = 1.80610$ | $v_{19} = 40.95$ |
| $r_{31} = -3.3476$ | $d_{31} = 1.2060$ | | |
| $r_{32} = \infty$ | $d_{32} = 10.3004$ | $n_{20} = 1.62004$ | $v_{20} = 36.25$ |
| $r_{33} = -4.8820$ | $d_{33} = 6.0970$ | | |
| $r_{34} = 6.6082$ | $d_{34} = 0.3863$ | $n_{21} = 1.78472$ | $v_{21} = 25.71$ |
| $r_{35} = 2.4906$ | $d_{35} = 1.2446$ | $n_{22} = 1.67003$ | $v_{22} = 47.25$ |
| $r_{36} = -6.3768$ | $d_{36} = 0.6438$ | | |
| $r_{37} = \infty$ | $d_{37} = 1.2876$ | $n_{23} = 1.76820$ | $v_{23} = 71.79$ |
| $r_{38} = \infty$ | $d_{38} = 2.4850$ | | |
| $r_{39} = \infty$ | $d_{39} = 0.4292$ | $n_{24} = 1.51633$ | $v_{24} = 64.15$ |
| $r_{40} = \infty$ | $d_{40} = 1.4040$ | | |
| $r_{41} = 2.2740$ | $d_{41} = 0.9742$ | $n_{25} = 1.71300$ | $v_{25} = 53.84$ |
| $r_{42} = -16.9838$ | $d_{42} = 0.7639$ | | |
| $r_{43} = -1.8326$ | $d_{43} = 0.6309$ | $n_{26} = 1.75520$ | $v_{26} = 27.51$ |
| $r_{44} = 3.0113$ | $d_{44} = 2.7797$ | | |
| $r_{45} = -2.2661$ (aspherical surface) | $d_{45} = 0.815$ | $n_{27} = 1.8300$ | $v_{27} = 40.78$ |
| $r_{46} = -1.7989$ (aspherical surface) | $d_{46} = 1.3428$ | | |
| $r_{47} = \infty$ | $d_{47} = 0.4292$ | $n_{28} = 1.51633$ | $v_{28} = 64.15$ |
| $r_{48} = \infty$ | $d_{48} = 0.4292$ | | |
| $r_{49} = \infty$ | $d_{49} = 6.4378$ | $n_{29} = 1.54869$ | $v_{29} = 45.55$ |
| $r_{50} = \infty$ | $d_{50} = 0.8584$ | | |
| $r_{51} = \infty$ | $d_{51} = 0.1717$ | $n_{30} = 1.51633$ | $v_{30} = 64.15$ |
| $r_{52} = \infty$ | | | |

-continued

Embodiment 6 aspherical surface coefficients (45th surface) $P = 1.0000, E = 0.13352$
$F = -0.43569 \times 10^{-4}, G = 0.87072 \times 10^{-1}$
(46th surface) $P = 1.000, E = 0.87072 \times 10^{-1}$
$F = 0.87024 \times 10^{-4}, G = 0.33315 = 10^{-8}$
$DT_L = 8.38,$ $DT_0 = -31.72,$ $|DT_L/DT_0| = 0.264$
$AS_4 = 10.48,$ $L_4 = 28.73$ $|AS_4|/L_4 = 0.365$

Embodiment 7

$f = 1.000$, F number = $-13.083$,
image height = 0.6579, object distance = $-3.3000$
field angle = (in air) 69.8°, DT = $-4.474$

| | | | |
|---|---|---|---|
| $r_1 = \infty$ | | | |
| | $d_1 = 0.0987$ | $n_1 = 1.76820$ | $v_1 = 71.79$ |
| $r_2 = \infty$ | | | |
| | $d_2 = 0.0658$ | $n_2 = 1.78800$ | $v_2 = 47.43$ |
| $r_3 = 0.2154$ | | | |
| $r_4 = \infty$ | | | |
| | $d_4 = 0.6514$ | $n_3 = 1.788800$ | $v_3 = 47.43$ |
| $r_5 = \infty$ (stop) | | | |
| | $d_5 = 0.9934$ | $n_4 = 1.78800$ | $v_4 = 47.43$ |
| $r_6 = -0.7629$ | | | |
| | $d_6 = 0.0329$ | | |
| $r_7 = 1.2821$ | | | |
| | $d_7 = 0.4638$ | $n_5 = 1.64000$ | $v_5 = 60.09$ |
| $r_8 = -0.6729$ | | | |
| | $d_8 = 0.3388$ | $n_6 = 1.84666$ | $v_6 = 23.88$ |
| $r_9 = -6.8714$ | | | |
| | $d_9 = 0.5724$ | | |
| $r_{10} = -0.5898$ | | | |
| | $d_{10} = 0.1941$ | $n_7 = 1.72825$ | $v_7 = 28.46$ |
| $r_{11} = -2.1848$ | | | |
| | $d_{11} = 0.3388$ | $n_8 = 1.77250$ | $v_8 = 49.66$ |
| $r_{12} = -0.8542$ | | | |
| | $d_{12} = 1.3487$ | | |
| $r_{13} = 2.1500$ | | | |
| | $d_{13} = 7.8947$ | $n_9 = 1.62004$ | $v_9 = 36.25$ |
| $r_{14} = \infty$ | | | |
| | $d_{14} = 0.5559$ | | |
| $r_{15} = 5.0842$ | | | |
| | $d_{15} = 0.8717$ | $n_{10} = 1.65160$ | $v_{10} = 58.67$ |
| $r_{16} = -1.1487$ | | | |
| | $d_{16} = 0.4441$ | $n_{11} = 1.80610$ | $v_{11} = 40.95$ |
| $r_{17} = -2.5658$ | | | |
| | $d_{17} = 0.9243$ | | |
| $r_{18} = \infty$ | | | |
| | $d_{18} = 7.8947$ | $n_{12} = 1.62004$ | $v_{12} = 36.25$ |
| $r_{19} = -3.7418$ | | | |
| | $d_{19} = 1.3158$ | | |
| $r_{20} = 3.7418$ | | | |
| | $d_{20} = 7.8947$ | $n_{13} = 1.62004$ | $v_{13} = 36.25$ |
| $r_{21} = \infty$ | | | |
| | $d_{21} = 0.5559$ | | |
| $r_{22} = 5.0842$ | | | |
| | $d_{22} = 0.8717$ | $n_{14} = 1.65160$ | $v_{14} = 58.67$ |
| $r_{23} = -1.1487$ | | | |
| | $d_{23} = 0.4441$ | $n_{15} = 1.80610$ | $v_{15} = 40.95$ |
| $r_{24} = -2.5658$ | | | |
| | $d_{24} = 0.9243$ | | |
| $r_{25} = \infty$ | | | |
| | $d_{25} = 7.8947$ | $n_{16} = 1.62004$ | $v_{16} = 36.25$ |
| $r_{26} = -3.7418$ | | | |
| | $d_{26} = 1.3158$ | | |
| $r_{27} = 3.7418$ | | | |
| | $d_{27} = 7.8947$ | $n_{17} = 1.62004$ | $v_{17} = 36.25$ |
| $r_{28} = \infty$ | | | |
| | $d_{28} = 0.5559$ | | |
| $r_{29} = 5.0842$ | | | |
| | $d_{29} = 0.8717$ | $n_{18} = 1.65160$ | $v_{18} = 58.67$ |
| $r_{30} = -1.1487$ | | | |
| | $d_{30} = 0.4441$ | $n_{19} = 1.80610$ | $v_{19} = 40.95$ |
| $r_{31} = -2.5658$ | | | |
| | $d_{31} = 0.9243$ | | |

Embodiment 7

| | | | |
|---|---|---|---|
| $r_{32} = \infty$ | | | |
| | $d_{32} = 7.8947$ | $n_{20} = 1.62004$ | $v_{20} = 36.25$ |
| $r_{33} = -3.7418$ | | | |
| | $d_{33} = 4.6343$ | | |
| $r_{34} = 5.0648$ | | | |
| | $d_{34} = 0.2961$ | $n_{21} = 1.78472$ | $v_{21} = 25.71$ |
| $r_{35} = 1.9089$ | | | |
| | $d_{35} = 0.9539$ | $n_{22} = 1.67003$ | $v_{22} = 47.25$ |
| $r_{36} = -4.8875$ | | | |
| | $d_{36} = 0.4934$ | | |
| $r_{37} = \infty$ | | | |
| | $d_{37} = 0.9868$ | $n_{23} = 1.76820$ | $v_{23} = 71.79$ |
| $r_{38} = \infty$ | | | |
| | $d_{38} = 1.9046$ | | |
| $r_{39} = \infty$ | | | |
| | $d_{39} = 0.3289$ | $n_{24} = 1.51633$ | $v_{24} = 64.15$ |
| $r_{40} = \infty$ | | | |
| | $d_{40} = 0.9108$ | | |
| $r_{41} = 2.4845$ (aspherical surface) | | | |
| | $d_{41} = 0.7467$ | $n_{25} = 1.71300$ | $v_{25} = 53.84$ |
| $r_{42} = -2.5961$ (aspherical surface) | | | |
| | $d_{42} = 0.5855$ | | |
| $r_{43} = -1.0409$ | | | |
| | $d_{43} = 0.4836$ | $n_{26} = 1.75520$ | $v_{26} = 27.51$ |
| $r_{44} = 3.2731$ (aspherical surface) | | | |
| | $d_{44} = 3.0897$ | | |
| $r_{45} = -1.8176$ (aspherical surface) | | | |
| | $d_{45} = 0.6250$ | $n_{27} = 1.59270$ | $v_{27} = 35.29$ |
| $r_{46} = -1.2162$ (aspherical surface) | | | |
| | $d_{46} = 1.1945$ | | |
| $r_{47} = \infty$ | | | |
| | $d_{47} = 0.3289$ | $n_{28} = 1.51633$ | $v_{28} = 64.15$ |
| $r_{48} = \infty$ | | | |
| | $d_{48} = 0.3289$ | | |
| $r_{49} = \infty$ | | | |
| | $d_{49} = 4.9342$ | $n_{29} = 1.54869$ | $v_{29} = 45.55$ |
| $r_{50} = \infty$ | | | |
| | $d_{50} = 0.6579$ | | |
| $r_{51} = \infty$ | | | |
| | $d_{51} = 0.1316$ | $n_{30} = 1.51633$ | $v_{30} = 64.15$ |
| $r_{52} = \infty$ | | | |

| | aspherical surface coefficients |
|---|---|
| (41th surface) | $P = 1.000$, $E = -0.33325 \times 10^{-1}$ |
| | $F = 0.10691$, $G = 0.26829 \times 10$ |
| (42th surface) | $P = 1.0000$, $E = -0.58905 \times 10^{-2}$ |
| | $F = 0.38286$, $G = 0.37810 \times 10$ |
| (4th surface) | $P = 1.0000$, $E = -0.68028 \times 10^{-1}$ |
| | $F = -0.10757 \times 10$, $G = -0.12867 \times 10^2$ |
| (45th surface) | $P = 1.0000$, $E = 0.28548$ |
| | $F = -0.11615 \times 10^{-1}$, $G = -0.85568 \times 10^{-1}$ |
| (46th surface) | $P = 1.0000$, $E = 0.21966$ |
| | $F = 0.17178 \times 10^{-1}$, $G = 0.43596 \times 10^{-1}$ |
| $DT_L = 10.53$, | $DT_0 = -15.0$, $DT_L/DT_0| = 0.702$ |
| $AS_4 = 11.29$, | $L_4 = 22.96$, $|AS_4/L_4| = 0.492$ |

Embodiment 8

$f = 1.000$, F number $= -15.875$,
image height $= 0.9266$, object distance $= -3.7000$
SK $= 0.001$, field angle $=$ (in air) 99.2°,
(in water) 70°, DT $= -5.005$

| | | | |
|---|---|---|---|
| $r_1 = \infty$ | | | |
| | $d_1 = 0.1112$ | $n_1 = 1.76820$ | $v_1 = 71.79$ |
| $r_2 = \infty$ | | | |
| | $d_2 = 0.0741$ | $n_2 = 1.78800$ | $v_2 = 47.43$ |
| $r_3 = 0.2331$ | | | |
| | $d_3 = 0.1112$ | | |
| $r_4 = \infty$ | | | |
| | $d_4 = 0.7363$ | $n_3 = 1.78800$ | $v_3 = 47.43$ |
| $r_5 = \infty$ (stop) | | | |

-continued

Embodiment 8

| | | | |
|---|---|---|---|
| $r_6 = -0.9040$ | $d_5 = 1.1170$ | $n_4 = 1.78800$ | $v_4 = 47.43$ |
| $r_7 = 1.5979$ | $d_6 = 0.0371$ | | |
| $r_8 = -0.6827$ | $d_7 = 0.5226$ | $n_5 = 1.64000$ | $v_5 = 60.09$ |
| $r_9 = -2.6294$ | $d_8 = 0.3818$ | $n_6 = 1.84666$ | $v_6 = 23.88$ |
| $r_{10} = -0.6957$ | $d_9 = 0.6449$ | | |
| $r_{11} = -2.5660$ | $d_{10} = 0.2187$ | $n_7 = 1.72825$ | $v_7 = 28.46$ |
| $r_{12} = -0.9040$ | $d_{11} = 0.3818$ | $n_8 = 1.77250$ | $v_8 = 49.66$ |
| $r_{13} = 4.2161$ | $d_{12} = 1.5196$ | | |
| $r_{14} = \infty$ | $d_{13} = 8.8955$ | $n_9 = 1.62004$ | $v_9 = 36.25$ |
| $r_{15} = 5.7287$ | $d_{14} = 0.6264$ | | |
| $r_{16} = -1.2943$ | $d_{15} = 0.9822$ | $n_{10} = 1.65160$ | $v_{10} = 58.67$ |
| $r_{17} = -2.8910$ | $d_{16} = 0.5004$ | $n_1 = 1.80610$ | $v_{11} = 40.95$ |
| $r_{18} = \infty$ | $d_{17} = 1.0415$ | | |
| $r_{19} = -4.2161$ | $d_{18} = 8.8955$ | $n_{12} = 1.62004$ | $v_{12} = 36.25$ |
| $r_{20} = 4.2161$ | $d_{19} = 1.4826$ | | |
| $r_{21} = \infty$ | $d_{20} = 8.8955$ | $n_{13} = 1.62004$ | $v_{13} = 36.25$ |
| $r_{22} = 5.7287$ | $d_{21} = 0.6264$ | | |
| $r_{23} = -1.2943$ | $d_{22} = 0.9822$ | $n_{14} = 1.65160$ | $v_{14} = 58.67$ |
| $r_{24} = -2.8910$ | $d_{23} = 0.5004$ | $n_{15} = 1.80610$ | $v_{15} = 40.95$ |
| $r_{25} = \infty$ | $d_{24} = 1.0415$ | | |
| $r_{26} = -4.2161$ | $d_{25} = 8.8955$ | $n_{16} = 1.62004$ | $v_{16} = 36.25$ |
| $r_{27} = 4.2161$ | $d_{26} = 1.4826$ | | |
| $r_{28} = \infty$ | $d_{27} = 8.8955$ | $n_{17} = 1.62004$ | $v_{17} = 36.25$ |
| $r_{29} = 5.7287$ | $d_{28} = 0.6264$ | | |
| $r_{30} = -1.2943$ | $d_{29} = 0.9822$ | $n_{18} = 1.65160$ | $v_{18} = 58.67$ |
| $r_{31} = -2.8910$ | $d_{30} = 0.5004$ | $n_{19} = 1.80610$ | $v_{19} = 40.95$ |
| $r_{32} = \infty$ | $d_{31} = 1.0415$ | | |
| $r_3 = -4.2161$ | $d_{32} = 8.8955$ | $n_{20} = 1.62004$ | $v_{20} = 36.25$ |
| $r_{34} = -1.9714$ (aspherical surface) | $d_{33} = 0.9217$ | | |
| $r_{35} = 3.0482$ (aspherical surface) | $d_{34} = 0.3706$ | $n_{21} = 1.51633$ | $v_{21} = 64.15$ |
| $r_{36} = 6.8801$ | $d_{35} = 1.3952$ | | |
| $r_{37} = -3.6937$ | $d_{36} = 0.5708$ | $n_{22} = 1.71300$ | $v_{22} = 53.84$ |
| $r_{38} = 1.8078$ | $d_{37} = 0.0408$ | | |
| $r_{39} = -2.9085$ | $d_{38} = 0.5745$ | $n_{23} = 1.61700$ | $v_{23} = 62.79$ |
| $r_{40} = 1.2613$ | $d_{39} = 0.1927$ | $n_{24} = 1.59270$ | $v_{24} = 35.29$ |
| $r_{41} = -1.0568$ | $d_{40} = 0.8154$ | | |
| $r_{42} = -1.2446$ | $d_{41} = 0.2409$ | $n_{25} = 1.7520$ | $v_{25} = 27.51$ |
| $r_{43} = -1.6391$ | $d_{42} = 0.8599$ | $n_{26} = 1.69680$ | $v_{26} = 56.49$ |
| | $d_{43} = 0.0556$ | | |

-continued

Embodiment 8

| | | | |
|---|---|---|---|
| $r_{44} = -18.8015$ | | | |
| | $d_{44} = 0.5486$ | $n_{27} = 1.80400$ | $v_{27} = 46.57$ |
| $r_{45} = -4.5904$ | | | |
| | $d_{45} = 0.3468$ | | |
| $r_{46} = \infty$ | | | |
| | $d_{46} = 1.1119$ | $n_{28} = 1.76820$ | $v_{28} = 71.79$ |
| $r_{47} = \infty$ | | | |
| | $d_{47} = 1.1119$ | | |
| $r_{48} = \infty$ | | | |
| | $d_{48} = 0.3706$ | $n_{29} = 1.51633$ | $v_{29} = 64.15$ |
| $r_{49} = \infty$ | | | |
| | $d_{49} = 1.2163$ | | |
| $r_{50} = 2.1605$ | | | |
| | $d_{50} = 0.8414$ | $n_{30} = 1.71300$ | $v_{30} = 53.84$ |
| $r_{51} = -39.9663$ | | | |
| | $d_{51} = 0.6597$ | | |
| $r_{52} = -3.1145$ | | | |
| | $d_{52} = 0.5448$ | $n_{31} = 1.75520$ | $v_{31} = 27.51$ |
| $r_{53} = 1.8725$ | | | |
| | $d_{53} = 1.2231$ | | |
| $r_{54} = 11.0460$ | | | |
| | $d_{54} = 0.7042$ | $n_{32} = 1.59270$ | $v_{32} = 35.29$ |
| $r_5 = -3.7561$ | | | |
| | $d_{55} = 1.1558$ | | |
| $r_{56} = \infty$ | | | |
| | $d_{56} = 0.3706$ | $n_{33} = 1.51633$ | $v_{33} = 64.15$ |
| $r_{57} = \infty$ | | | |
| | $d_{57} = 0.3706$ | | |
| $r_{58} = \infty$ | | | |
| | $d_{58} = 5.5597$ | $n_{34} = 1.54869$ | $v_{34} = 45.55$ |
| $r_{59} = \infty$ | | | |
| | $d_{59} = 0.7413$ | | |
| $r_{60} = \infty$ | | | |
| | $d_{60} = 0.1483$ | $n_{35} = 1.51633$ | $v_{35} = 64.15$ |
| $r_{61} = \infty$ | | | |

| aspherical surface coefficients | |
|---|---|
| (34th surface) | $P = 1.000, E = 0.95022$ |
| | $F = 0.70429 \times 10, G = 0.14920 \times 10^2$ |
| (35th surface) | $P = 1.000, E = -0.30583$ |
| | $F = 0.33279 \times 10, G = -0.41329 \times 10$ |
| $DT_L = 11.59,$ | $DT_0 = -35.19,$ $DT_L/DT_0 = 0.329,$ |
| $AS_3 = 0.54,$ | $L_4 = 22.31,$ $|AS_3|/L_4 = 0.024$ |

Embodiment 10

$f = 1.000$, F number $= -15.849$,
image height $= 0.8951$, object distance $= -3.6000$
field angle $=$ (in air) 100.3°, (in water) 70°,
$DT = -5.008$

| | | | |
|---|---|---|---|
| $r_1 = \infty$ | | | |
| | $d_1 = 0.1074$ | $n_1 = 1.76820$ | $v_1 = 71.79$ |
| $r_2 = \infty$ | | | |
| | $d_2 = 0.0716$ | $n_2 = 1.78800$ | $v_2 = 47.43$ |
| $r_3 = 0.2252$ | | | |
| | $d_3 = 0.1074$ | | |
| $r_4 = \infty$ | | | |
| | $d_4 = 0.7114$ | $n_3 = 1.78800$ | $v_3 = 47.43$ |
| $r_5 = \infty$ (stop) | | | |
| | $d_5 = 1.0787$ | $n_4 = 1.78800$ | $v_4 = 47.43$ |
| $r_6 = -0.8733$ | | | |
| | $d_6 = 0.0358$ | | |
| $r_7 = 1.5435$ | | | |
| | $d_7 = 0.5048$ | $n_5 = 1.64000$ | $v_5 = 60.09$ |
| $r_8 = -0.6595$ | | | |
| | $d_8 = 0.3688$ | $n_6 = 1.84666$ | $v_6 = 23.88$ |
| $r_9 = -2.5399$ | | | |
| | $d_9 = 0.6230$ | | |
| $r_{10} = -0.6720$ | | | |
| | $d_{10} = 0.2112$ | $n_7 = 1.72825$ | $v_7 = 28.46$ |
| $r_{11} = -2.4787$ | | | |
| | $d_{11} = 0.3688$ | $n_8 = 1.77250$ | $v_8 = 49.66$ |
| $r_{12} = -0.873$ | | | |
| | $d_{12} = 1.4680$ | | |
| $r_{13} = 4.0727$ | | | |

-continued

Embodiment 10

| | | | |
|---|---|---|---|
| $r_{14} = \infty$ | $d_{13} = 8.5929$ | $n_9 = 1.62004$ | $v_9 = 36.25$ |
| $r_{15} = 5.5338$ | $d_{14} = 0.6051$ | | |
| $r_{16} = -1.2503$ | $d_{15} = 0.9488$ | $n_{10} = 1.65160$ | $v_{10} = 58.67$ |
| $r_{17} = -2.7927$ | $d_{16} = 0.4834$ | $n_{11} = 1.80610$ | $v_{11} = 40.95$ |
| $r_{18} = \infty$ | $d_{17} = 1.0061$ | | |
| $r_{19} = -4.0727$ | $d_{18} = 8.5929$ | $n_{12} = 1.62004$ | $v_{12} = 36.25$ |
| $r_{20} = 4.0727$ | $d_{19} = 1.4322$ | | |
| $r_{21} = \infty$ | $d_{20} = 8.5929$ | $n_{13} = 1.62004$ | $v_{13} = 36.25$ |
| $r_{22} = 5.5338$ | $d_{21} = 0.6051$ | | |
| $r_{23} = -1.2503$ | $d_{22} = 0.9488$ | $n_{14} = 1.65160$ | $v_{14} = 58.67$ |
| $r_{24} = -2.7927$ | $d_{23} = 0.4834$ | $n_{15} = 1.80610$ | $v_{15} = 40.95$ |
| $r_{25} = \infty$ | $d_{24} = 1.0061$ | | |
| $r_{26} = -4.0727$ | $d_{25} = 8.5929$ | $n_{16} = 1.62004$ | $v_{16} = 36.25$ |
| $r_{27} = 4.0727$ | $d_{26} = 1.4322$ | | |
| $r_{28} = \infty$ | $d_{27} = 8.5929$ | $n_{17} = 1.62004$ | $v_{17} = 36.25$ |
| $r_{29} = 5.5338$ | $d_{28} = 0.6051$ | | |
| $r_{30} = -1.2503$ | $d_{29} = 0.9488$ | $n_{18} = 1.65160$ | $v_{18} = 58.67$ |
| $r_{31} = -2.7927$ | $d_{30} = 0.4834$ | $n_{19} = 1.80610$ | $v_{19} = 40.95$ |
| $r_{32} = \infty$ | $d_{31} = 1.0061$ | | |
| $r_{33} = -2.2870$ (aspherical surface) | $d_{32} = 8.5929$ | $n_{20} = 1.62004$ | $v_{20} = 36.25$ |
| $r_{34} = \infty$ | $d_{33} = 0.9600$ | | |
| $r_{35} = \infty$ | $d_{34} = 0.3580$ | $n_{21} = 1.51633$ | $v_{21} = 64.15$ |
| $r_{36} = 5.4255$ | $d_{35} = 1.2153$ | | |
| $r_{37} = -1.9813$ | $d_{36} = 0.5514$ | $n_{22} = 1.71300$ | $v_2 = 53.84$ |
| $r_{38} = 2.5551$ | $d_{37} = 0.0394$ | | |
| $r_{39} = -0.6161$ | $d_{38} = 0.5550$ | $n_{23} = 1.61700$ | $v_{23} = 62.79$ |
| $r_{40} = 0.8516$ | $d_{39} = 0.1862$ | $n_{24} = 1.59270$ | $v_{24} = 35.29$ |
| $r_{41} = -1.0480$ | $d_{40} = 0.7877$ | | |
| $r_{42} = -6.7288$ | $d_{41} = 0.2327$ | $n_{25} = 1.75520$ | $v_{25} = 27.51$ |
| $r_{43} = -1.7392$ | $d_{42} = 0.8306$ | $n_{26} = 1.69680$ | $v_{26} = 56.49$ |
| $r_4 = 8.7666$ | $d_{43} = 0.0537$ | | |
| $r_{45} = -6.5691$ | $d_4 = 0.5299$ | $n_{27} = 1.80400$ | $v_{27} = 46.57$ |
| $r_{46} = \infty$ | $d_{45} = 0.4675$ | | |
| $r_{47} = \infty$ | $d_{46} = 1.0741$ | $n_{28} = 1.76820$ | $v_{28} = 71.79$ |
| $r_{48} = \infty$ | $d_{47} = 1.0741$ | | |
| $r_{49} = \infty$ | $d_{48} = 0.3580$ | $n_{29} = 1.51633$ | $v_{29} = 64.15$ |
| $r_{50} = 2.0870$ | $d_{49} = 1.1749$ | | |
| $r_{51} = -38.6069$ | $d_{50} = 0.8127$ | $n_{30} = 1.71300$ | $v_{30} = 53.84$ |
| | $d_{51} = 0.6373$ | | |

-continued

Embodiment 10

| | | | |
|---|---|---|---|
| $r_{52} = -3.0086$ | | | |
| | $d_{52} = 0.5263$ | $n_{31} = 1.75520$ | $v_{31} = 27.51$ |
| $r_{53} = 1.8088$ | | | |
| | $d_{53} = 1.1815$ | | |
| $r_{54} = 10.6702$ | | | |
| | $d_{54} = 0.6803$ | $n_{32} = 1.59270$ | $v_{32} = 35.29$ |
| $r_{55} = -3.6284$ | | | |
| | $d_5 = 1.1165$ | | |
| $r_{56} = \infty$ | | | |
| | $d_{56} = 0.3580$ | $n_3 = 1.51633$ | $v_{33} = 64.15$ |
| $r_{57} = \infty$ | | | |
| | $d_{57} = 0.3580$ | | |
| $r_{58} = \infty$ | | | |
| | $d_{58} = 5.3706$ | $n_{34} = 1.54869$ | $v_{34} = 45.55$ |
| $r_{59} = \infty$ | | | |
| | $d_{59} = 0.7161$ | | |
| $r_{60} = \infty$ | | | |
| | $d_{60} = 0.1432$ | $n_{35} = 1.51633$ | $v_{35} = 64.15$ |
| $r_{61} = \infty$ | | | | aspherical surface coefficients

(3th surface) $\quad P = 1.0000, E = 0.60855$
$F = -0.12947 \times 10, G = 0.11011 \times 10$
$DT_L = 11.12,\quad DT_0 = -35.92,\quad DT_L/|DT_0| = 0.310,$
$AS_3 = -0.67,\quad L_4 = 21.69,\quad |AS_3|/L_4 = 0.031$

Embodiment 11

$f = 1.000$, F number $= -15.949$
image height $= 0.7228$, object distance $= -2.9000$
field angle $=$ (in air) 71.5°, DT $= -5.166$

| | | | |
|---|---|---|---|
| $r_1 = \infty$ | | | |
| | $d_1 = 0.0867$ | $n_1 = 1.76820$ | $v_1 = 71.79$ |
| $r_2 = \infty$ | | | |
| | $d_2 = 0.0578$ | $n_2 = 1.78800$ | $v_2 = 47.43$ |
| $r_3 = 0.1893$ | | | |
| | $d_3 = 0.0867$ | | |
| $r_4 = \infty$ | | | |
| | $d_4 = 0.5725$ | $n_3 = 1.78800$ | $v_3 = 47.43$ |
| $r_5 = \infty$ (stop) | | | |
| | $d_5 = 0.8730$ | $n_4 = 1.78800$ | $v_4 = 47.43$ |
| $r_6 = -0.6705$ | | | |
| | $d_6 = 0.0289$ | | |
| $r_7 = 1.1268$ | | | |
| | $d_7 = 0.4076$ | $n_5 = 1.64000$ | $v_5 = 60.09$ |
| $r_8 = -0.5914$ | | | |
| | $d_8 = 0.2978$ | $n_6 = 1.84666$ | $v_6 = 23.88$ |
| $r_9 = -6.0-390$ | | | |
| | $d_9 = 0.5030$ | | |
| $r_{10} = -0.5184$ | | | |
| | $d_{10} = 0.1706$ | $n_7 = 1.72825$ | $v_7 = 28.46$ |
| $r_1 = -1.9201$ | | | |
| | $d_{11} = 0.2978$ | $n_8 = 1.77250$ | $v_8 = 49.66$ |
| $r_{12} = -0.7507$ | | | |
| | $d_{12} = 1.1853$ | | |
| $r_{13} = 1.8896$ | | | |
| | $d_{13} = 6.9384$ | $n_9 = 1.62004$ | $v_9 = 36.25$ |
| $r_{14} = \infty$ | | | |
| | $d_{14} = 0.4886$ | | |
| $r_{15} = 4.4683$ | | | |
| | $d_{15} = 0.7661$ | $n_{10} = 1.65160$ | $v_{10} = 58.67$ |
| $r_{16} = -1.0095$ | | | |
| | $d_{16} = 0.3903$ | $n_{11} = 1.80610$ | $v_{11} = 40.95$ |
| $r_{17} = -2.2550$ | | | |
| | $d_{17} = 0.8124$ | | |
| $r_{18} = \infty$ | | | |
| | $d_{18} = 6.9384$ | $n_{12} = 1.62004$ | $v_{12} = 36.25$ |
| $r_{19} = -3.2885$ | | | |
| | $d_{19} = 1.1564$ | | |
| $r_{20} = 3.2885$ | | | |
| | $d_{20} = 6.9384$ | $n_{13} = 1.62004$ | $v_{13} = 36.25$ |
| $r_{21} = \infty$ | | | |
| | $d_{21} = 0.4886$ | | |
| $r_{22} = 4.4683$ | | | |
| | $d_{22} = 0.7661$ | $n_{14} = 1.65160$ | $v_{14} = 58.67$ |

-continued

Embodiment 11

| | | | |
|---|---|---|---|
| $r_{23} = -1.0095$ | $d_{23} = 0.3903$ | $n_{15} = 1.80610$ | $v_{15} = 40.95$ |
| $r_{24} = -2.2550$ | $d_{24} = 0.8124$ | | |
| $r_{25} = \infty$ | $d_{25} = 6.9384$ | $n_{16} = 1.62004$ | $v_{16} = 36.25$ |
| $r_{26} = -3.2885$ | $d_{26} = 1.1564$ | | |
| $r_{27} = 3.2885$ | $d_{27} = 6.9384$ | $n_{17} = 1.62004$ | $v_{17} = 36.25$ |
| $r_{28} = \infty$ | $d_{28} = 0.4886$ | | |
| $r_{29} = 4.4683$ | $d_{29} = 0.7661$ | $n_{18} = 1.65160$ | $v_{18} = 58.67$ |
| $r_{30} = -1.0095$ | $d_{30} = 0.3903$ | $n_{19} = 1.80610$ | $v_{19} = 40.95$ |
| $r_{31} = -2.2550$ | $d_{31} = 0.8124$ | | |
| $r_{32} = \infty$ | $d_{32} = 6.9384$ | $n_{20} = 1.62004$ | $v_{20} = 36.25$ |
| $r_{33} = -3.2885$ | $d_{33} = 0.7085$ | | |
| $r_{34} = -1.5377$ (aspherical surface) | $d_{34} = 0.2891$ | $n_{21} = 1.51633$ | $v_{21} = 64.15$ |
| $r_{35} = 2.3776$ (aspherical surface) | $d_{35} = 1.0882$ | | |
| $r_{36} = 5.3664$ | $d_{36} = 0.4452$ | $n_{22} = 1.71300$ | $v_{22} = 53.84$ |
| $r_{37} = -2.8811$ | $d_{37} = 0.0318$ | | |
| $r_{38} = 1.4101$ | $d_{38} = 0.4481$ | $n_{23} = 1.61700$ | $v_{23} = 62.79$ |
| $r_{39} = -2.2686$ | $d_{39} = 0.1503$ | $n_{24} = 1.59270$ | $v_{24} = 35.29$ |
| $r_{40} = 0.9838$ | $d_{40} = 0.6360$ | | |
| $r_{41} = -0.8243$ | $d_{41} = 0.1879$ | $n_{25} = 1.75520$ | $v_{25} = 27.51$ |
| $r_{42} = -0.9708$ | $d_{42} = 0.6707$ | $n_{26} = 1.69680$ | $v_{26} = 56.49$ |
| $r_{43} = -1.2785$ | $d_{43} = 0.0434$ | | |
| $r_{44} = -14.6651$ | $d_4 = 0.4279$ | $n_{27} = 1.80400$ | $v_{27} = 46.57$ |
| $r_{45} = -3.5805$ | $d_{45} = 0.2705$ | | |
| $r_{46} = \infty$ | $d_{46} = 0.8673$ | $n_{28} = 1.76820$ | $v_{28} = 71.79$ |
| $r_{47} = \infty$ | $d_{47} = 0.8673$ | | |
| $r_{48} = \infty$ | $d_{48} = 0.2891$ | $n_{29} = 1.51633$ | $v_{29} = 64.15$ |
| $r_{49} = \infty$ | $d_{49} = 0.9487$ | | |
| $r_{50} = 1.6852$ | $d_{50} = 0.6563$ | $n_{30} = 1.71300$ | $v_{30} = 53.84$ |
| $r_{51} = -31.1735$ | $d_{51} = 0.5146$ | | |
| $r_{52} = -2.4293$ | $d_{52} = 0.4250$ | $n_{31} = 1.75520$ | $v_{31} = 27.51$ |
| $r_{53} = 1.4605$ | $d_{53} = 0.9540$ | | |
| $r_{54} = 8.6158$ | $d_{54} = 0.5493$ | $n_{32} = 1.59270$ | $v_{32} = 35.29$ |
| $r_5 = -2.9297$ | $d_{55} = 0.9015$ | | |
| $r_{56} = \infty$ | $d_{56} = 0.2891$ | $n_{33} = 1.51633$ | $v_3 = 64.15$ |
| $r_{57} = \infty$ | $d_{57} = 0.2891$ | | |
| $r_{58} = \infty$ | $d_{58} = 4.3365$ | $n_{34} = 1.54869$ | $v_{34} = 45.55$ |
| $r_{59} = \infty$ | $d_{59} = 0.5782$ | | |
| $r_{60} = \infty$ | $d_{60} = 0.1156$ | $n_{35} = 1.51633$ | $v_{35} = 64.15$ |
| $r_{61} = \infty$ | | | |

-continued

Embodiment 11 aspherical surface coefficients (34th surface) $P = 1.0000$, $E = 0.20024 \times 10$
$F = 0.24395 \times 10^2$, $G = 0.84944 \times 10^2$
(35th surface) $P = 1.0000$, $E = -0.63338$
$F = 0.11527 \times 10^2$, $G = -0.23530 \times 10^2$
$DT_L = 13.68$, $DT_O = -18.84$, $|DT_L/DT_O| = 0.73$
$AS_3 = 0.42$, $L_4 = 17.4$, $|AS_3|/L_4 = 0.024$

Embodiment 12

$f = 1.000$, F number $= -15.849$
image height $= 0.9104$, object distance $= -3.6400$
field angle $=$ (in air) $99.7°$, (in water) $= 70°$
$DT = -5.001$

| | | | |
|---|---|---|---|
| $r_1 = \infty$ | | | |
| | $d_1 = 0.1092$ | $n_1 = 1.76820$ | $v_1 = 71.79$ |
| $r_2 = \infty$ | | | |
| | $d_2 = 0.0728$ | $n_2 = 1.78800$ | $v_2 = 47.43$ |
| $r_3 = 0.2291$ | | | |
| | $d_3 = 0.1092$ | | |
| $r_4 = \infty$ | | | |
| | $d_4 = 0.7235$ | $n_3 = 1.78800$ | $v_3 = 47.43$ |
| $r_5 = \infty$ (stop) | | | |
| | $d_5 = 1.0974$ | $n_4 = 1.78800$ | $v_4 = 47.43$ |
| $r_6 = -0.8882$ | | | |
| | $d_6 = 0.0364$ | | |
| $r_7 = 1.5699$ | | | |
| | $d_7 = 0.5135$ | $n_5 = 1.64000$ | $v_5 = 60.09$ |
| $r_8 = -0.6708$ | | | |
| | $d_8 = 0.3751$ | $n_6 = 1.84666$ | $v_6 = 23.88$ |
| $r_9 = -2.5834$ | | | |
| | $d_9 = 0.6336$ | | |
| $r_{10} = -0.6835$ | | | |
| | $d_{10} = 0.2149$ | $n_7 = 1.72825$ | $v_7 = 28.46$ |
| $r_{11} = -2.5211$ | | | |
| | $d_{11} = 0.3751$ | $n_8 = 1.77250$ | $v_8 = 49.66$ |
| $r_{12} = -0.8882$ | | | |
| | $d_{12} = 1.4931$ | | |
| $r_{13} = 4.1424$ | | | |
| | $d_{13} = 8.7400$ | $n_9 = 1.62004$ | $v_9 = 36.25$ |
| $r_{14} = \infty$ | | | |
| | $d_{14} = 0.6154$ | | |
| $r_{15} = 5.6286$ | | | |
| | $d_{15} = 0.9650$ | $n_{10} = 1.65160$ | $v_{10} = 58.67$ |
| $r_{16} = -1.2717$ | | | |
| | $d_{16} = 0.4916$ | $n_{11} = 1.80610$ | $v_{11} = 40.95$ |
| $r_{17} = -2.8405$ | | | |
| | $d_{17} = 1.0233$ | | |
| $r_{18} = \infty$ | | | |
| | $d_{18} = 8.7400$ | $n_{12} = 1.62004$ | $v_{12} = 36.25$ |
| $r_{19} = -4.1424$ | | | |
| | $d_{19} = 1.4567$ | | |
| $r_{20} = 4.1424$ | | | |
| | $d_{20} = 8.7400$ | $n_{13} = 1.62004$ | $v_{13} = 36.25$ |
| $r_{21} = \infty$ | | | |
| | $d_{21} = 0.6154$ | | |
| $r_{22} = 5.6286$ | | | |
| | $d_{22} = 0.9650$ | $n_{14} = 1.65160$ | $v_{14} = 58.67$ |
| $r_{23} = -1.2717$ | | | |
| | $d_{23} = 0.4916$ | $n_{15} = 1.80610$ | $v_{15} = 40.95$ |
| $r_{24} = -2.8405$ | | | |
| | $d_{24} = 1.0233$ | | |
| $r_{25} = \infty$ | | | |
| | $d_{25} = 8.7400$ | $n_{16} = 1.62004$ | $v_{16} = 36.25$ |
| $r_{26} = -4.1424$ | | | |
| | $d_{26} = 1.4567$ | | |
| $r_{27} = 4.1424$ | | | |
| | $d_{27} = 8.7400$ | $n_{17} = 1.62004$ | $v_{17} = 36.25$ |
| $r_{28} = \infty$ | | | |
| | $d_{28} = 0.6154$ | | |
| $r_{29} = 5.6286$ | | | |
| | $d_{29} = 0.9650$ | $n_{18} = 1.65160$ | $v_{18} = 58.67$ |
| $r_{30} = -1.2717$ | | | |
| | $d_{30} = 0.4916$ | $n_{19} = 1.80610$ | $v_{19} = 40.95$ |

-continued

Embodiment 12

| | | | |
|---|---|---|---|
| $r_{31} = -2.8405$ | | | |
| | $d_{31} = 1.0233$ | | |
| $r_{32} = \infty$ | | | |
| | $d_{32} = 8.7400$ | $n_{20} = 1.62004$ | $v_{20} = 36.25$ |
| $r_{33} = -4.1424$ | | | |
| | $d_{33} = 0.8871$ | | |
| $r_{34} = -8.5391$ (aspherical surface) | | | |
| | $d_{34} = 0.3642$ | $n_{21} = 1.51633$ | $v_{21} = 64.15$ |
| $r_{35} = 7.0933$ (aspherical surface) | | | |
| | $d_{35} = 1.3947$ | | |
| $r_{36} = 6.2764$ | | | |
| | $d_{36} = 0.5608$ | $n_{22} = 1.71300$ | $v_{22} = 53.84$ |
| $r_{37} = -4.1698$ | | | |
| | $d_{37} = 0.0401$ | | |
| $r_{38} = 1.7539$ | | | |
| | $d_{38} = 0.5645$ | $n_{23} = 1.61700$ | $v_{23} = 62.79$ |
| $r_{39} = 9.0023$ | | | |
| | $d_{39} = 0.1894$ | $n_{24} = 1.59270$ | $v_{24} = 35.29$ |
| $r_{40} = 1.2404$ | | | |
| | $d_{40} = 0.8012$ | | |
| $r_{41} = -1.0211$ | | | |
| | $d_{41} = 0.2367$ | $n_{25} = 1.75220$ | $v_{25} = 27.51$ |
| $r_{42} = -4.6678$ | | | |
| | $d_{42} = 0.8449$ | $n_{26} = 1.69680$ | $v_{26} = 56.49$ |
| $r_{43} = -1.6288$ | | | |
| | $d_{43} = 0.0546$ | | |
| $r_{44} = 160.2083$ | | | |
| | $d_{44} = 0.5390$ | $n_{27} = 1.80400$ | $v_{27} = 46.57$ |
| $r_{45} = -4.9362$ | | | |
| | $d_{45} = 0.3168$ | | |
| $r_{46} = \infty$ | | | |
| | $d_{46} = 1.0925$ | $n_{28} = 1.76820$ | $v_{28} = 71.79$ |
| $r_{47} = \infty$ | | | |
| | $d_{47} = 1.0925$ | | |
| $r_{48} = \infty$ | | | |
| | $d_{48} = 0.3642$ | $n_{29} = 1.51633$ | $v_{29} = 64.15$ |
| $r_{49} = \infty$ | | | |
| | $d_{49} = 1.2055$ | | |
| $r_{50} = 2.1313$ | | | |
| | $d_{50} = 0.8267$ | $n_{30} = 1.71300$ | $v_{30} = 53.84$ |
| $r_{51} = -41.2318$ | | | |
| | $d_{51} = 0.6482$ | | |
| $r_{52} = -3.0694$ | | | |
| | $d_{52} = 0.5353$ | $n_{31} = 1.75520$ | $v_{31} = 27.51$ |
| $r_{53} = 1.8060$ | | | |
| | $d_{53} = 1.2017$ | | |
| $r_{54} = 10.7148$ (aspherical surface) | | | |
| | $d_{54} = 0.6919$ | $n_{32} = 1.59270$ | $v_{32} = 35.29$ |
| $r_{55} = -3.4543$ (aspherical surface) | | | |
| | $d_{55} = 1.1251$ | | |
| $r_{56} = \infty$ | | | |
| | $d_{56} = 0.3642$ | $n_{33} = 1.51633$ | $v_{33} = 64.15$ |
| $r_{57} = \infty$ | | | |
| | $d_{57} = 0.3642$ | | |
| $r_{58} = \infty$ | | | |
| | $d_{58} = 5.4625$ | $n_{34} = 1.54869$ | $v_{34} = 45.55$ |
| $r_{59} = \infty$ | | | |
| | $d_{59} = 0.7283$ | | |
| $r_{60} = \infty$ | | | |
| | $d_{60} = 0.1457$ | $n_{35} = 1.51633$ | $v_{35} = 64.15$ |
| $r_{61} = \infty$ | | | |

| | aspherical surface coefficients |
|---|---|
| (34th surface) | $P = 1.0000$, $E = 0.26547$ |
| | $F = 0.33037 \times 10$, $G = 0.50948 \times 10^2$ |
| (35th surface) | $P = 1.0000$, $E = -0.95542 \times 10^{-1}$ |
| | $F = -0.37236$, $G = 0.88179 \times 10$ |
| (54th surface) | $P = 1.0000$, $R = -0.89677 \times 10^{-1}$ |
| | $F = 0.19300 \times 10^{-3}$, $G = 0.12131 \times 10^{-2}$ |
| (55th surface) | $P = 1.0000$, $E = 0.10436 \times 10^{-2}$ |
| | $F = 0.40163 \times 10^{-4}$, $G = -0.70770 \times 10^{-3}$ |
| $DT_L = 11.87$, | $DT_0 = -35.52$, $DT_L/|DT_0| = 0.33$ |
| $AS_3 = 0.51$, | $L_4 = 21.91$, $|AS_3|/L_4 = 0.02$, $AS_4 = 8.89$ |
| $|AS_4|/L_4 = 0.41$ | |

Embodiment 13 f = 1.000, F number = −12.572
image height = 1.1468, object distance = −4.5900
field angle = (in air) 100°, DT = −4.997

| | | | |
|---|---|---|---|
| $r_1 = \infty$ | | | |
| | $d_1 = 0.1376$ | $n_1 = 1.76820$ | $v_1 = 71.79$ |
| $r_2 = \infty$ | | | |
| | $d_2 = 0.0917$ | $n_2 = 1.78800$ | $v_2 = 47.43$ |
| $r_3 = 0.2885$ | | | |
| | $d_3 = 0.1376$ | | |
| $r_4 = \infty$ | | | |
| | $d_4 = 0.9116$ | $n_3 = 1.78800$ | $v_3 = 47.43$ |
| $r_5 = \infty$ (stop) | | | |
| | $d_5 = 1.3820$ | $n_4 = 1.78800$ | $v_4 = 47.43$ |
| $r_6 = -1.1188$ | | | |
| | $d_6 = 0.0459$ | | |
| $r_7 = 1.9775$ | | | |
| | $d_7 = 0.6468$ | $n_5 = 1.64000$ | $v_5 = 60.09$ |
| $r_8 = -0.8450$ | | | |
| | $d_8 = 0.4725$ | $n_6 = 1.84666$ | $v_6 = 23.88$ |
| $r_9 = -3.2541$ | | | |
| | $d_9 = 0.7982$ | | |
| $r_{10} = -0.8610$ | | | |
| | $d_{10} = 0.2706$ | $n_7 = 1.72825$ | $v_7 = 28.46$ |
| $r_{11} = -3.1757$ | | | |
| | $d_{11} = 0.4725$ | $n_8 = 1.77250$ | $v_8 = 49.66$ |
| $r_{12} = -1.1188$ | | | |
| | $d_{12} = 1.8807$ | | |
| $r_{13} = 5.2179$ | | | |
| | $d_{13} = 11.0092$ | $n_9 = 1.62004$ | $v_9 = 36.25$ |
| $r_{14} = \infty$ | | | |
| | $d_{14} = 0.7752$ | | |
| $r_{15} = 7.0899$ | | | |
| | $d_{15} = 1.2156$ | $n_{10} = 1.65160$ | $v_{10} = 58.67$ |
| $r_{16} = -1.6018$ | | | |
| | $d_{16} = 0.6193$ | $n_{11} = 1.80610$ | $v_{11} = 40.95$ |
| $r_{17} = -3.5780$ | | | |
| | $d_{17} = 1.2890$ | | |
| $r_{18} = \infty$ | | | |
| | $d_{18} = 11.0092$ | $n_{12} = 1.62004$ | $v_{12} = 36.25$ |
| $r_{19} = -5.2179$ | | | |
| | $d_{19} = 1.8349$ | | |
| $r_{20} = 5.2179$ | | | |
| | $d_{20} = 11.0092$ | $n_{13} = 1.62004$ | $v_{13} = 36.25$ |
| $r_{21} = \infty$ | | | |
| | $d_{21} = 0.7752$ | | |
| $r_{22} = 7.0889$ | | | |
| | $d_{22} = 1.2156$ | $n_{14} = 1.65160$ | $v_{14} = 58.67$ |
| $r_{23} = -1.6018$ | | | |
| | $d_{23} = 0.6193$ | $n_{15} = 1.80610$ | $v_{15} = 40.95$ |
| $r_{24} = -3.5780$ | | | |
| | $d_{24} = 1.2890$ | | |
| $r_{25} = \infty$ | | | |
| | $d_{25} = 11.0092$ | $n_{16} = 1.62004$ | $v_{16} = 36.25$ |
| $r_{26} = -5.2179$ | | | |
| | $d_{26} = 1.8349$ | | |
| $r_{27} = 5.2179$ | | | |
| | $d_{27} = 11.0092$ | $n_{17} = 1.62004$ | $v_{17} = 36.25$ |
| $r_{28} = \infty$ | | | |
| | $d_{28} = 0.7752$ | | |
| $r_{29} = 7.0899$ | | | |
| | $d_{29} = 1.2156$ | $n_{18} = 1.65160$ | $v_{18} = 58.67$ |
| $r_{30} = -1.6018$ | | | |
| | $d_{30} = 0.6193$ | $n_{19} = 1.80610$ | $v_{19} = 40.95$ |
| $r_{31} = -3.5780$ | | | |
| | $d_{31} = 1.2890$ | | |
| $r_{32} = \infty$ | | | |
| | $d_{32} = 11.0092$ | $n_{20} = 1.62004$ | $v_{20} = 36.25$ |
| $r_{33} = -5.2179$ | | | |
| | $d_{33} = 1.1174$ | | |
| $r_{34} = -1.7424$ (aspherical surface) | | | |
| | $d_{34} = 0.4587$ | $n_{21} = 1.51633$ | $v_{21} = 64.15$ |
| $r_{35} = -6.8163$ (aspherical surface) | | | |
| | $d_{35} = 1.7604$ | | |
| $r_{36} = 13.2295$ | | | |
| | $d_{36} = 0.7064$ | $n_{22} = 1.71300$ | $v_{22} = 53.84$ |
| $r_{37} = -6.2573$ | | | |
| | $d_{37} = 0.0505$ | | |
| $r_{38} = 2.3743$ | | | |

-continued

Embodiment 13

| | | | |
|---|---|---|---|
| $r_{39} = 4.4242$ | $d_{38} = 0.7110$ | $n_{23} = 1.61700$ | $v_{23} = 62.79$ |
| $r_{40} = 1.4967$ | $d_{39} = 0.2385$ | $n_{24} = 1.59270$ | $v_{24} = 35.29$ |
| $r_{41} = -1.2817$ | $d_{40} = 1.0092$ | | |
| $r_{42} = -8.9174$ | $d_{41} = 0.2982$ | $n_{25} = 1.75520$ | $v_{25} = 27.51$ |
| $r_{43} = -2.0456$ | $d_{42} = 1.0642$ | $n_{26} = 1.69680$ | $v_{26} = 56.49$ |
| $r_{44} = 65.16091$ | $d_{43} = 0.0688$ | | |
| $r_{45} = -5.9127$ | $d_{44} = 0.6789$ | $n_{27} = 1.80400$ | $v_{27} = 46.57$ |
| $r_{46} = 2.6861$ (aspherical surface) | $d_{45} = 1.9743$ | | |
| $r_{47} = -56.7455$ (aspherical surface) | $d_{46} = 1.0413$ | $n_{28} = 1.71300$ | $v_{28} = 53.84$ |
| $r_{48} = -3.9380$ | $d_{47} = 0.8165$ | | |
| $r_{49} = 2.2606$ | $d_{48} = 0.6743$ | $n_{29} = 1.75520$ | $v_{29} = 27.51$ |
| $r_{50} = 11.8306$ | $d_{49} = 1.5138$ | | |
| $r_{51} = -4.0690$ (aspherical surface) | $d_{50} = 0.8716$ | $n_{30} = 1.59270$ | $v_{30} = 35.29$ |
| $r_{52} = \infty$ | $d_{51} = 1.0532$ | | |
| $r_{53} = \infty$ | $d_{52} = 0.4587$ | $n_{31} = 1.51633$ | $v_{31} = 64.15$ |
| $r_{54} = \infty$ | $d_{53} = 0.4587$ | | |
| $r_{55} = \infty$ | $d_{54} = 6.807$ | $n_{32} = 1.54869$ | $v_{32} = 45.55$ |
| $r_{56} = \infty$ | $d_{55} = 0.9174$ | | |
| $r_{57} = \infty$ | $d_{56} = 0.1835$ | $n_{33} = 1.51633$ | $v_{33} = 64.15$ |

| | aspherical surface coefficients |
|---|---|
| (34th surface) | $P = 1.0000$, $E = 0.23038$ |
| | $F = 0.21222 \times 10$, $G = 0.503939$ |
| (35th surface) | $P = 1.0000$, $E = -0.70576$ |
| | $F = -0.10698 \times 10$, $G = -0.33745$ |
| (46th surface) | $P = 1.0000$, $E = -0.54186 \times 10^{-3}$ |
| | $F = 0.13130 \times 10^{-2}$, $G = -0.50898 \times 10^{-3}$ |
| (47th surface) | $P = 1.0000$, $E = 0.83674 \times 10^{-3}$ |
| | $F = -0.71126 \times 10^{-3}$, $G = -0.11388 \times 10^{-3}$ |
| (51th surface) | $P = 1.0000$, $E = 0.47097 \times 10^{-2}$ |
| | $F = 0.50775 \times 10^{-3}$, $G = -0.58144 \times 10^{-3}$ |
| $DT_L = 30.72$, | $DT_0 = -35.72$, $DT_L/|DT_0| = 0.86$ |
| $AS_3 = 0.65$, | $L_4 = 24.08$, $|AS_3|/L_4 = 0.027$, |
| $AS_4 = 14.87$, | $|AS_4|/L_4 = 0.618$ |

Embodiment 14

$f = 1.000$, F number $= -15.927$
image height $= 0.7074$, object distance $= -2.8300$
field angle $=$ (in air) 71.6°, $DT = -5.113$

| | | | |
|---|---|---|---|
| $r_1 = \infty$ | | | |
| | $d_1 = 0.0849$ | $n_1 = 1.76820$ | $v_1 = 71.79$ |
| $r_2 = \infty$ | | | |
| | $d_2 = 0.0566$ | $n_2 = 1.78800$ | $v_2 = 47.43$ |
| $r_3 = 0.1853$ | | | |
| | $d_3 = 0.0849$ | | |
| $r_4 = \infty$ | | | |
| | $d_4 = 0.5603$ | $n_3 = 1.78800$ | $v_3 = 47.43$ |
| $r_5 = \infty$ (stop) | | | |
| | $d_5 = 0.8545$ | $n_4 = 1.78800$ | $v_4 = 47.43$ |
| $r_6 = -0.6562$ | | | |
| | $d_6 = 0.0283$ | | |
| $r_7 = 1.1029$ | | | |
| | $d_7 = 0.3990$ | $n_5 = 1.64000$ | $v_5 = 60.09$ |
| $r_8 = -0.5789$ | | | |
| | $d_8 = 0.2915$ | $n_6 = 1.84666$ | $v_6 = 23.88$ |

-continued

Embodiment 14

| | | | |
|---|---|---|---|
| $r_9 = -5.9109$ | | | |
| | $d_9 = 0.4924$ | | |
| $r_{10} = -0.5074$ | | | |
| | $d_{10} = 0.1669$ | $n_7 = 1.72825$ | $v_7 = 28.46$ |
| $r_{11} = -1.8794$ | | | |
| | $d_{11} = 0.2915$ | $n_8 = 1.77250$ | $v_8 = 49.66$ |
| $r_{12} = -0.7348$ | | | |
| | $d_{12} = 1.1602$ | | |
| $r_{13} = 1.8495$ | | | |
| | $d_{13} = 6.7912$ | $n_9 = 1.62004$ | $v_9 = 36.25$ |
| $r_{14} = \infty$ | | | |
| | $d_{14} = 0.4782$ | | |
| $r_{15} = 4.3735$ | | | |
| | $d_{15} = 0.7499$ | $n_{10} = 1.65160$ | $v_{10} = 58.67$ |
| $r_{16} = -0.9881$ | | | |
| | $d_{16} = 0.3820$ | $n_{11} = 1.80610$ | $v_{11} = 40.95$ |
| $r_{17} = -2.2071$ | | | |
| | $d_{17} = 0.7951$ | | |
| $r_{18} = 0\ \infty$ | | | |
| | $d_{18} = 6.7912$ | $n_{12} = 1.62004$ | $v_{12} = 36.25$ |
| $r_{19} = 1.1319$ | | | |
| | $d_{19} = 1.1319$ | | |
| $r_{20} = 3.2187$ | | | |
| | $d_{20} = 6.7912$ | $n_{13} = 1.62004$ | $v_{13} = 36.25$ |
| $r_{21} = \infty$ | | | |
| | $d_{21} = 0.4782$ | | |
| $r_{22} = 4.3735$ | | | |
| | $d_{22} = 0.7499$ | $n_{14} = 1.65160$ | $v_{14} = 58.67$ |
| $r_{23} = -0.9881$ | | | |
| | $d_{23} = 0.3820$ | $n_{15} = 1.80610$ | $v_{15} = 40.95$ |
| $r_{24} = -2.2071$ | | | |
| | $d_{24} = 0.7951$ | | |
| $r_{25} = \infty$ | | | |
| | $d_{25} = 6.7912$ | $n_{16} = 1.62004$ | $v_{16} = 36.25$ |
| $r_{26} = -3.2187$ | | | |
| | $d_{26} = 1.1319$ | | |
| $r_{27} = 3.2187$ | | | |
| | $d_{27} = 6.7912$ | $n_{17} = 1.62004$ | $v_{17} = 36.25$ |
| $r_{28} = \infty$ | | | |
| | $d_{28} = 0.4782$ | | |
| $r_{29} = 4.3735$ | | | |
| | $d_{29} = 0.7499$ | $n_{18} = 1.65160$ | $v_{18} = 58.67$ |
| $r_{30} = -0.9881$ | | | |
| | $d_{30} = 0.3820$ | $n_{19} = 1.80610$ | $v_{19} = 40.95$ |
| $r_{31} = -2.2071$ | | | |
| | $d_{31} = 0.7951$ | | |
| $r_{32} = \infty$ | | | |
| | $d_{32} = 6.7912$ | $n_{20} = 1.62004$ | $v_{20} = 36.25$ |
| $r_{33} = -3.2187$ | | | |
| | $d_{33} = 0.6791$ | | |
| $r_{34} = -6.6351$ (aspherical surface) | | | |
| | $d_{34} = 0.2830$ | $n_{21} = 1.51633$ | $v_{21} = 64.15$ |
| $r_{35} = 5.5117$ (aspherical surface) | | | |
| | $d_{35} = 1.0837$ | | |
| $r_{36} = 4.8769$ | | | |
| | $d_{36} = 0.4358$ | $n_{22} = 1.71300$ | $v_{22} = 53.84$ |
| $r_{37} = -3.2400$ | | | |
| | $d_{37} = 0.0311$ | | |
| $r_{38} = 1.3628$ | | | |
| | $d_{38} = 0.4386$ | $n_{23} = 1.61700$ | $v_{23} = 62.79$ |
| $r_{39} = 6.9950$ | | | |
| | $d_{39} = 0.1471$ | $n_{24} = 1.59270$ | $v_{24} = 35.29$ |
| $r_{40} = 0.9638$ | | | |
| | $d_{40} = 0.6225$ | | |
| $r_{41} = -0.7934$ | | | |
| | $d_{41} = 0.1839$ | $n_{25} = 1.75520$ | $v_{25} = 27.51$ |
| $r_{42} = -3.6270$ | | | |
| | $d_{42} = 0.6565$ | $n_{26} = 1.69680$ | $v_{26} = 56.49$ |
| $r_{43} = -1.2656$ | | | |
| | $d_{43} = 0.0424$ | | |
| $r_{44} = 124.4856$ | | | |
| | $d_{44} = 0.4188$ | $n_{27} = 1.80400$ | $v_{27} = 46.57$ |
| $r_{45} = -3.8356$ | | | |
| | $d_{45} = 0.2462$ | | |
| $r_{46} = \infty$ | | | |
| | $d_{46} = 0.8489$ | $n_{28} = 1.76820$ | $v_{28} = 71.79$ |
| $r_{47} = \infty$ | | | |
| | $d_{47} = 0.8489$ | | |

Embodiment 14

$r_{48} = \infty$
$\quad d_{48} = 0.2830 \quad n_{29} = 1.51633 \quad \nu_{29} = 64.15$
$r_{49} = \infty$
$\quad d_{49} = 0.9367$
$r_{50} = 1.6561$
$\quad d_{50} = 0.6423 \quad n_{30} = 1.71300 \quad \nu_{30} = 53.84$
$r_{51} = -32.0381$
$\quad d_{51} = 0.5037$
$r_{52} = -2.3850$
$\quad d_{52} = 0.4160 \quad n_{31} = 1.75520 \quad \nu_{31} = 27.51$
$r_{53} = 1.4033$
$\quad d_{53} = 0.9338$
$r_{54} = 8.3256$ (aspherical surface)
$\quad d_{54} = 0.5376 \quad n_{32} = 1.59270 \quad \nu_{32} = 35.29$
$r_{55} = -2.6841$ (aspherical surface)
$\quad d_{55} = 0.8742$
$r_{56} = \infty$
$\quad d_{56} = 0.2830 \quad n_{33} = 1.51633 \quad \nu_{33} = 64.15$
$r_{57} = \infty$
$\quad d_{57} = 0.2830$
$r_{58} = \infty$
$\quad d_{58} = 4.2445 \quad n_{34} = 1.54869 \quad \nu_{34} = 45.55$
$r_{59} = \infty$
$\quad d_{59} = 0.5659$
$r_{60} = \infty$
$\quad d_{60} = 0.1132 \quad n_{35} = 1.51633 \quad \nu_{35} = 64.15$
$r_{61} = \infty$ aspherical surface coefficients (34th surface) $\quad P = 1.0000, E = 0.56587$
$\quad F = 0.11663 \times 10^2, G = 0.29792 \times 10^3$
(35th surface) $\quad P = 1.0000, E = -0.20365$
$\quad F = -0.13146 \times 10, G = 0.51562 \times 10^2$
(54th surface) $\quad P = 1.0000, E = -0.19115 \times 10^{-2}$
$\quad F = 0.68137 \times 10^{-3}, G = 0.70934 \times 10^{-2}$
(55th surface) $\quad P = 1.0000, E = 0.22246 \times 10^{-2}$
$\quad F = 0.14179 \times 10^{-3}, G = -0.41382 \times 10^{-2}$ $DT_L = 13.78, \quad DT_0 = -18.89, \quad |DT_L/DT_0| = 0.73$
$AS_3 = 0.40, \quad L_4 = 17.02, \quad |AS_3|/L_4 = 0.02, AS_4 = 6.90$
$|AS_4|/L_4 = 0.41$

Embodiment 15

$f = 516.297$, F number $= 561.561$
image height $= 7.5000$, object distance $= -10.0000$
$SK = -1000.017$ field angle $=$ (in air) $95°$,
(in water) $68.8°$, $DT = -6.342$ $r_1 = \infty$
$\quad d_1 = 0.3000 \quad n_1 = 1.76820 \quad \nu_1 = 71.79$
$r_2 = \infty$
$\quad d_2 = 0.2000 \quad n_2 = 1.78800 \quad \nu_2 = 47.43$
$r_3 = 0.6290$
$\quad d_3 = 0.3000$
$r_4 = \infty$
$\quad d_4 = 1.9864 \quad n_3 \text{ ' } 1.78800 \quad \nu_3 = 47.43$
$r_5 = \infty$ (stop)
$\quad d_5 = 3.0136 \quad n_4 = 1.7880 \quad \nu_4 = 47.43$
$r_6 = -2.4390$
$\quad d_6 \text{ 3' } 0.1000$
$r_7 = 4.3110$
$\quad d_7 = 1.4100 \quad n_5 = 1.64000 \quad \nu_5 = 60.09$
$r_8 = -1.8420$
$\quad d_8 = 1.0300 \quad n_6 = 1.84666 \quad \nu_6 = 23.88$
$r_9 = -7.0940$
$\quad d_9 = 1.7400$
$r_{10} = -1.8770$
$\quad d_{10} = 0.5900 \quad n_7 = 1.72825 \quad \nu_7 = 28.46$
$r_{11} = -6.9230$
$\quad d_{11} = 1.0300 \quad n_8 = 1.77250 \quad \nu_8 = 49.66$
$r_{12} = -2.4390$
$\quad d_{12} = 4.1000$
$r_{13} = 11.3750$
$\quad d_{13} = 24.0000 \quad n_9 = 1.62004 \quad \nu_9 = 36.25$
$r_{14} = \infty$
$\quad d_{14} = 1.6900$ -continued

Embodiment 15

| | | | |
|---|---|---|---|
| $r_{15} = 15.4560$ | $d_{15} = 2.6500$ | $n_{10} = 1.65160$ | $\nu_{10} = 58.67$ |
| $r_{16} = -3.4290$ | $d_{16} = 1.3500$ | $n_{11} = 1.80610$ | $\nu_{11} = 40.95$ |
| $r_{17} = -7.800$ | $d_{17} = 2.8100$ | | |
| $r_{18} = \infty$ | $d_{18} = 24.0000$ | $n_{12} = 1.62004$ | $\nu_{12} = 36.25$ |
| $r_{19} = -11.3750$ | $d_{19} = 4.0000$ | | |
| $r_{20} = 11.3750$ | $d_{20} = 24.0000$ | $n_{13} = 1.62004$ | $\nu_{13} = 36.25$ |
| $r_{21} = \infty$ | $d_{21} = 1.6900$ | | |
| $r_{22} = 15.4560$ | $d_{22} = 2.6500$ | $n_{14} = 1.65160$ | $\nu_{14} = 58.67$ |
| $r_{23} = -3.4920$ | $d_{23} = 1.3500$ | $n_{15} = 1.80610$ | $\nu_{15} = 40.95$ |
| $r_{24} = -7.8000$ | $d_{24} = 2.8100$ | | |
| $r_{25} = \infty$ | $d_{25} = 24.0000$ | $n_{16} = 1.62004$ | $\nu_{16} = 36.25$ |
| $r_{26} = -11.3750$ | $d_{26} = 4.0000$ | | |
| $r_{27} = 11.3750$ | $d_{27} = 24.0000$ | $n_{17} = 1.62004$ | $\nu_{17} = 36.25$ |
| $r_{28} = \infty$ | $d_{28} = 1.6900$ | | |
| $r_{29} = 15.4560$ | $d_{29} = 2.6500$ | $n_{18} = 1.65160$ | $\nu_{18} = 58.67$ |
| $r_{30} = -3.4920$ | $d_{30} = 1.3500$ | $n_{19} = 1.80610$ | $\nu_{19} = 40.95$ |
| $r_{31} = -7.8000$ | $d_{31} = 2.8100$ | | |
| $r_{32} = \infty$ | $d_{32} = 24.0000$ | $n_{20} = 1.62004$ | $\nu_{20} = 36.25$ |
| $r_{33} = -11.3750$ | $d_{33} = 2.4868$ | | |
| $r_{34} = -5.3189$ (aspherical surface) | $d_{34} = 1.0000$ | $n_{21} = 1.51633$ | $\nu_{21} = 64.15$ |
| $r_{35} = 8.2240$ (aspherical surface) | $d_{35} = 3.7642$ | | |
| $r_{36} = 18.5625$ | $d_{36} = 1.5400$ | $n_{22} = 1.71300$ | $\nu_{22} = 53.84$ |
| $r_{37} = -9.9657$ | $d_{37} = 0.1100$ | | |
| $r_{38} = 4.8775$ | $d_{38} = 1.5500$ | $n_{23} = 1.61700$ | $\nu_{23} = 62.79$ |
| $r_{39} = -7.8470$ | $d_{39} = 0.5200$ | $n_{24} = 1.59270$ | $\nu_{24} = 35.29$ |
| $r_{40} = 3.4031$ | $d_{40} = 2.2000$ | | |
| $r_{41} = -2.8512$ | $d_{41} = 0.6500$ | $n_{25} = 1.75520$ | $\nu_{25} = 27.51$ |
| $r_{42} = -3.3580$ | $d_{42} = 2.3200$ | $n_{26} = 1.69680$ | $\nu_{26} = 56.49$ |
| $r_{43} = -4.4224$ | $d_{43} = 0.1500$ | | |
| $r_{44} = -50.7265$ | $d_{44} = 1.4800$ | $n_{27} = 1.80400$ | $\nu_{27} = 46.57$ |
| $r_{45} = -12.3848$ | $d_{45} = 0.9358$ | | |
| $r_{46} = \infty$ | $d_{46} = 3.0000$ | $n_{28} = 1.76820$ | $\nu_{28} = 71.79$ |
| $r_{47} = \infty$ | | | | aspherical surface coefficients (34th surface) $P = 1.0000$, $E = 0.48384 \times 10^{-1}$
$F = 0.49266 \times 10^{-1}$, $G = 0.14338 \times 10^{-1}$
(35th surface) $P = 1.0000$, $E = -0.15572 \times 10^{-1}$
$F = 0.23279 \times 10^{-1}$, $G = -0.39716 \times 10^{-2}$ $DT_E = 8.81$, $DT_O = -32.4$, $|DT_E/DT_O| = 0.27$
$AS_3 = 1.45$, $L_E = 19.67$, $|AS_3|/L_E = 0.074$

Embodiment 16

$f = -59.412$, F number $= -1034.540$
image height $= 7.5000$, object distance $= -10.0000$
SK $= -1000.000$, field angle $=$ (in air) 95°,
(in water) 68.8°, DT $= -2.299$

| | | | |
|---|---|---|---|
| $r_1 = \infty$ | | | |
| | $d_1 = 0.3000$ | $n_1 = 1.76820$ | $v_1 = 71.79$ |
| $r_2 = \infty$ | | | |
| | $d_2 = 0.2000$ | $n_2 = 1.78800$ | $v_2 = 47.43$ |
| $r_3 = 0.6290$ | | | |
| | $d_3 = 0.3000$ | | |
| $r_4 = \infty$ | | | |
| | $d_4 = 1.9797$ | $n_3 = 1.78800$ | $v_3 = 47.43$ |
| $r_5 = \infty$ (stop) | | | |
| | $d_5 = 3.0203$ | $n_4 = 1.78800$ | $v_4 = 47.43$ |
| $r_6 = -2.4390$ | | | |
| | $d_6 = 0.1000$ | | |
| $r_7 = 4.3110$ | | | |
| | $d_7 = 1.4100$ | $n_5 = 1.64000$ | $v_5 = 60.09$ |
| $r_8 = -1.8420$ | | | |
| | $d_8 = 1.0300$ | $n_6 = 1.84666$ | $v_6 = 23.88$ |
| $r_9 = -7.0940$ | | | |
| | $d_9 = 1.7400$ | | |
| $r_{10} = -1.8770$ | | | |
| | $d_{10} = 0.5900$ | $n_7 = 1.72825$ | $v_7 = 28.46$ |
| $r_{11} = -6.9230$ | | | |
| | $d_{11} = 1.0300$ | $n_8 = 1.77250$ | $v_8 = 49.66$ |
| $r_{12} = -2.4390$ | | | |
| | $d_{12} = 4.1000$ | | |
| $r_{13} = 11.3750$ | | | |
| | $d_{13} = 24.0000$ | $n_9 = 1.62004$ | $v_9 = 36.25$ |
| $r_{14} = \infty$ | | | |
| | $d_{14} = 1.6900$ | | |
| $r_{15} = 15.4560$ | | | |
| | $d_{15} = 2.6500$ | $n_{10} = 1.65160$ | $v_{10} = 58.67$ |
| $r_{16} = -3.4920$ | | | |
| | $d_{16} = 1.3500$ | $n_{11} = 1.80610$ | $v_{11} = 40.95$ |
| $r_{17} = -7.8000$ | | | |
| | $d_{17} = 2.8100$ | | |
| $r_{18} = \infty$ | | | |
| | $d_{18} = 24.0000$ | $n_{12} = 1.62004$ | $v_{12} = 36.25$ |
| $r_{19} = -11.3750$ | | | |
| | $d_{19} = 4.0000$ | | |
| $r_{20} = 11.3750$ | | | |
| | $d_{20} = 24.0000$ | $n_{13} = 1.62004$ | $v_{13} = 36.25$ |
| $r_{21} = \infty$ | | | |
| | $d_{21} = 1.6900$ | | |
| $r_{22} = 15.4560$ | | | |
| | $d_{22} = 2.6500$ | $n_{14} = 1.65160$ | $v_{14} = 58.67$ |
| $r_{23} = -3.4920$ | | | |
| | $d_{23} = 1.3500$ | $n_{15} = 1.80610$ | $v_{15} = 40.95$ |
| $r_{24} = -7.8000$ | | | |
| | $d_{24} = 2.8100$ | | |
| $r_{25} = \infty$ | | | |
| | $d_{25} = 24.0000$ | $n_{16} = 1.62004$ | $v_{16} = 36.25$ |
| $r_{26} = -11.3750$ | | | |
| | $d_{26} = 4.0000$ | | |
| $r_{27} = 11.3750$ | | | |
| | $d_{27} = 24.0000$ | $n_{17} = 1.62004$ | $v_{17} = 36.25$ |
| $r_{28} = \infty$ | | | |
| | $d_{28} = 1.6900$ | | |
| $r_{29} = 15.4560$ | | | |
| | $d_{29} = 2.6500$ | $n_{18} = 1.65160$ | $v_{18} = 58.67$ |
| $r_{30} = -3.4920$ | | | |
| | $d_{30} = 1.3500$ | $n_{19} = 1.80610$ | $v_{19} = 40.95$ |
| $r_{31} = -7.8000$ | | | |
| | $d_{31} = 2.8100$ | | |
| $r_{32} = \infty$ | | | |
| | $d_{32} = 24.0000$ | $n_{20} = 1.62004$ | $v_{20}$ 3' $36.25$ |
| $r_{33} = -11.3750$ | | | |
| | $d_3 = 14.2060$ | | |
| $r_{34} = 15.3970$ | | | |
| | $d_{34} = 0.9000$ | $n_{21} = 1.78472$ | $v_{21} = 25.71$ |
| $r_{35} = 5.8030$ | | | |
| | $d_{35} = 2.9000$ | $n_{22} = 1.67003$ | $v_{22} = 47.25$ |
| $r_{36} = -14.8580$ | | | |
| | $d_{36} = 1.5000$ | | |
| $r_{37} = \infty$ | | | |
| | $d_{37} = 3.0000$ | $n_{23} = 1.76820$ | $v_{23} = 71.79$ |

-continued

Embodiment 16

| | | | |
|---|---|---|---|
| $r_{38} = \infty$ | | | |
| | $d_{38} = 5.7900$ | | |
| $r_{39} = \infty$ | | | |
| | $d_{39} = 1.0000$ | $n_{24} = 1.51633$ | $v_{24} = 64.15$ |
| $r_{40} = \infty$ | | | |
| | $d_{40}$ 3' 3.2868 | | |
| $r_{41} = 7.5527$ (aspherical surface) | | | |
| | $d_{41} = 2.2700$ | $n_{25} = 1.71300$ | $v_{25} = 53.84$ |
| $r_{42} = -7.8922$ (aspherical surface) | | | |
| | $d_{42} = 1.7800$ | | |
| $r_{43} = -3.1644$ | | | |
| | $d_{43} = 1.4700$ | $n_{26} = 1.75520$ | $v_{26} = 27.51$ |
| $r_{44} = 9.9503$ (aspherical surface) | | | |
| | $d_{44} = 9.3927$ | | |
| $r_{45} = -5.5256$ (aspherical surface) | | | |
| | $d_{45} = 1.9000$ | $n_{27} = 1.59270$ | $v_{27} = 35.29$ |
| $r_{46} = -3.6973$ (aspherical surface) | | | |
| | $d_{46} = 28.2360$ | | |
| $r_{47} = 15.3970$ | | | |
| | $d_{47} = 0.9000$ | $n_{28} = 1.72825$ | $v_{28} = 28.46$ |
| $r_{48} = 5.8030$ | | | |
| | $d_{48} = 2.9000$ | $n_{29} = 1.67003$ | $v_{29} = 47.25$ |
| $r_{49} = -14.8580$ | | | |
| | $d_{49} = 1.5000$ | | |
| $r_{50} = \infty$ | | | |
| | $d_{50} = 3.0000$ | $n_{30} = 1.76820$ | $v_{30} = 71.79$ |
| $r_{51} = \infty$ | | | | aspherical surface coefficient (41th surface) $P = 1.0000, E = -0.11862 \times 10^{-2}$
$F = 0.41175 \times 10^{-3}, G = 0.11181 \times 10^{-2}$
(42th surface) $P = 1.0000, E = -0.20967 \times 10^{-3}$
$F = 0.14746 \times 10^{-2}, G = 0.15758 \times 10^{-2}$
(44th surface) $P = 1.0000, E = -0.24214 \times 10^{-2}$
$F = -0.41429 \times 10^{-2}, G = -0.53626 \times 10^{-2}$
(45th surface) $P = 1.0000, E = 0.10162 \times 10^{-1}$
$F = -0.44735 \times 10^{-4}, G = -0.35661 \times 10^{-4}$
(46th surface) $P = 1.0000, E = 0.78186 \times 10^{-2}$
$F = 0.66163 \times 10^{-4}, G = 0.18169 \times 10^{-4}$
$DT_E = 12.89,$ $DT_0 = -32.4,$ $|DT_E/DT_0| = 0.40$ wherein the reference symbols $r_1, r_2, \ldots$ represent radii of curvature on the surfaces of the respective lens elements, the reference symbols $d_1, d_2, \ldots$ designate thicknesses of the respective lens elements and airspaces reserved therebetween, the reference symbols $n_1, n_2, \ldots$ denote refractive indices of the respective lens elements, and the reference symbols $v_1, v_2, \ldots$ represent Abbe's numbers of the respective lens elements.

Illustrated in FIG. 6 is an overall composition of the first embodiment of the endoscope according to the present invention which consists of an objective optical system 0, and image relaying optical systems $R_1, R_2, R_3$ and $R_4$. The optical objective system and the image relaying optical systems other than the (n−1)th or the nth image relaying optical system configured so as to produce distortion are used commonly in all the embodiments of the present invention which are to be described below.

In the first embodiment, the fourth image relaying optical system $R_4$, out of the image relaying optical systems $R_1, R_2, R_3$ and $R_4$, corresponds to the nth image relaying optical system mentioned above and comprises an aspherical surface ASP adopted for producing the positive distortion.

Figure 7:
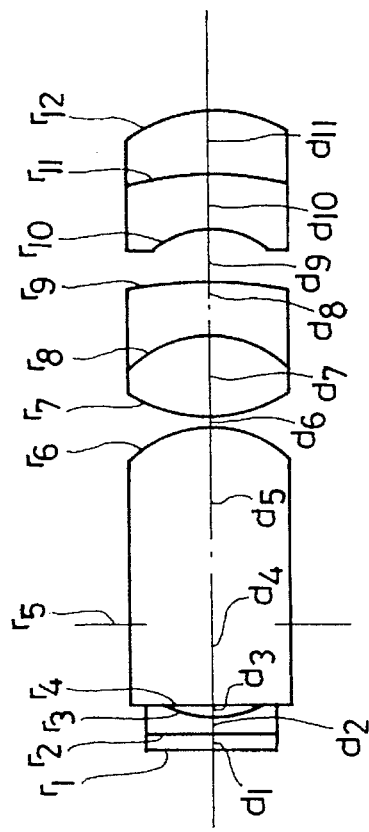
FIG. 7 shows a sectional view illustrating an objective optical system which is adopted in the first embodiment of the present invention.
Figure 8:
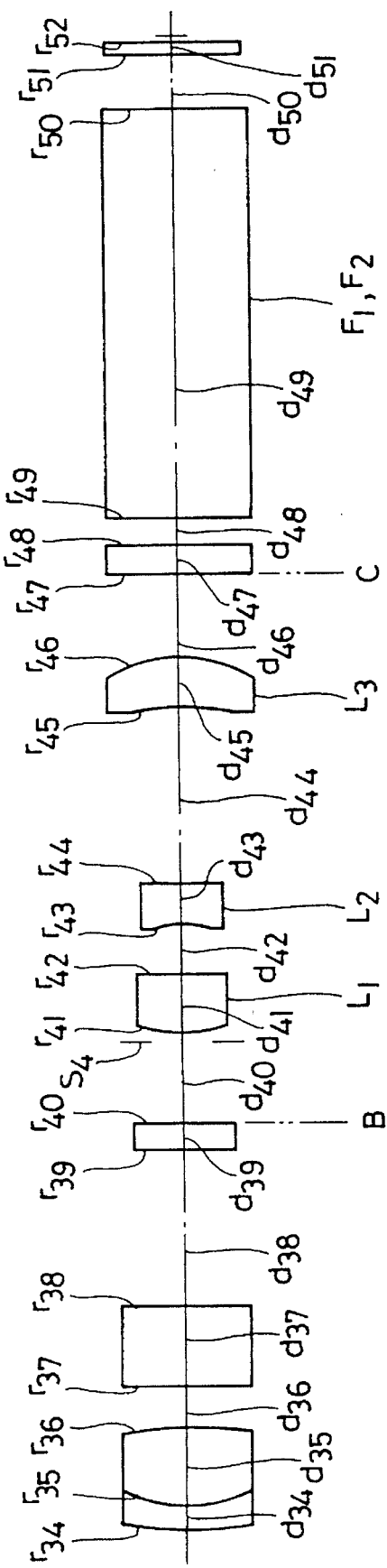
FIG. 8 shows a sectional view illustrating image relaying optical systems which are used in the first embodiment of the present invention.

FIG. 7 shows a sectional view illustrating the objective optical system 0 used in the first embodiment on an enlarged scale, whereas FIG. 8 shows a sectional view illustrating the image relaying optical system $R_4$ adopted in the first embodiment on an enlarged scale. In FIG. 8, the reference symbols $F_1$ and $F_2$ represent a low pass filter and an infrared light cutoff filter respectively which are adopted for TV camera. In FIG. 6, the reference symbol TV represents a TV camera, the reference symbol CU designates a control unit and the reference symbol M denotes a monitor.

In the first embodiment, the portion of the endoscope which is to be inserted into an object to be inspected can be prolonged by interposing, between the image relaying optical systems $R_2$ and $R_3$, one or plurality of image relaying optical systems each of which is the same as the image relaying optical system $R_1$. It is therefore possible to vary a length of the portion of the endoscope which is to be inserted into an object to be inspected by varying a number of the image relaying optical systems $R_1$ and $R_2$ to be disposed in the endoscope. Moreover, since no aspherical surface is used in the objective optical system 0 or the image relaying optical systems other than the image relaying optical system $R_4$, the image relaying optical systems to be used for prolonging the portion of the endoscope which is to be inserted into an object to be inspected can have small diameters, whereby the portion of the endoscope which is to be inserted into an object to be inspected can have a small diameter. The portion of the endoscope which is to be inserted into an object to be inspected can be prolonged also in the other embodiments of the present invention which is to be described below.

Figure 33A:
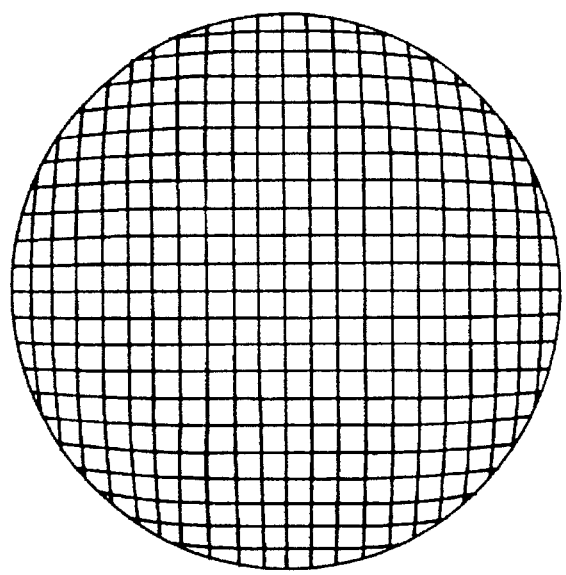
FIG. 33A shows a diagram visualizing appearance in water of an image formed by the first embodiment of the present invention.
Figure 33B:
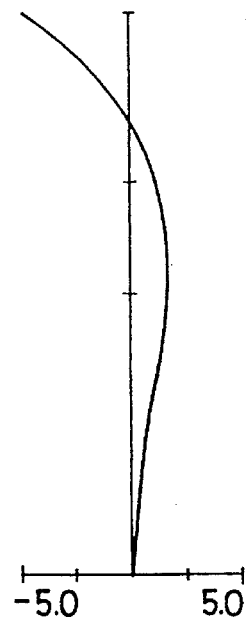
FIG. 33B shows a graph illustrating an aberration characteristic in water of the first embodiment of the present invention.

Appearance of an image formed in water by the first embodiment and distortion produced in water by the first embodiment are illustrated in FIG. 33A and FIG. 33B respectively. The first embodiment produces distortion of DT=−4.9% which is corrected at a level constituting no hindrance to practical use of the endoscope. Since distortion in water of the first embodiment is favorably corrected as described above, the endoscope preferred as the first embodiment is very effective for surgical operations of urinary organs and articulations while flowing physiological sodium chloride solution into human bodies. Further, the lens element having an aspherical surface can have a diameter 1.5 to 2 times as large as outside diameters of the lens elements composing the objective optical system.

Figure 9:
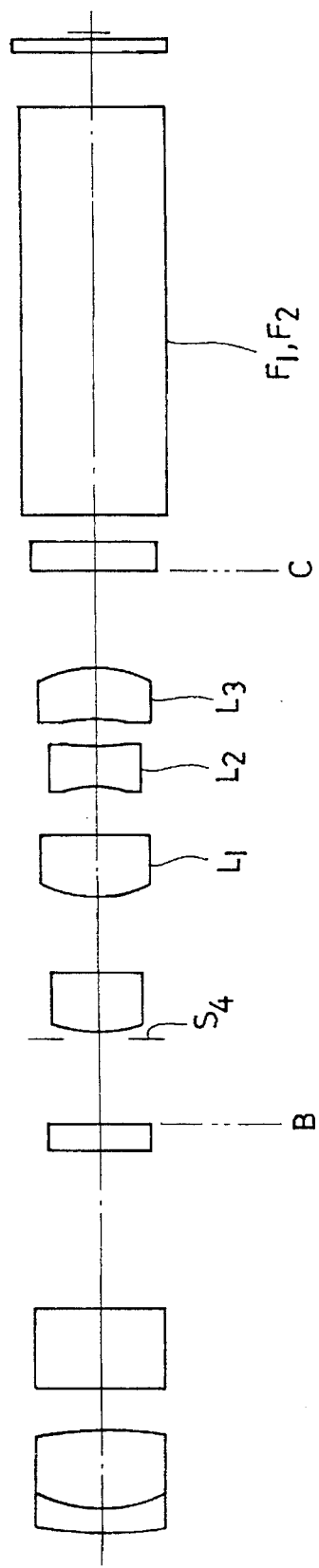
FIG. 9 shows a section view illustrating image relaying optical systems which are employed used in the first embodiment through a seventh embodiment of the endoscope according to the present invention.

The second embodiment has the same composition as that of the first embodiment, except for numerical data of $d_{40}$, $d_{44}$ and $d_{46}$ which have values of 3.5552, 0.4288 and 1.5409 respectively. In other words, the second embodiment is different from the first embodiment in that a plurality of lens elements $L_1$, $L_2$ and $L_3$ of the image relaying optical system $R_4$ are displaced as shown in FIG. 9, or $d_{40}$ and $d_{44}$ have values which are varied from those selected for the first embodiment as described above. Accordingly, the lens element $L_3$ is located relatively close to the lens elements $L_1$ and $L_2$, whereby the aspherical surface is brought nearer the pupil and distortion is reduced to DT=−8%. It is possible to vary an amount of distortion by changing a location of an aspherical surface. The distortion of −8% which is produced by the second embodiment is equal to the amount of distortion produced by only an objective optical system satisfying I=f·sin θ and the aspherical surface used in the second embodiment produces distortion of nearly zero. When the amount of distortion which is to be produced by the optical system can be varied, it is possible, for doctors and inspectors who are accostomed to observation of images affected by distortion produced by objective optical systems, to know what differences in appearance are produced between images affected by distortion and images having favorably corrected distortion by adopting the above-mentioned airspaces which have values varied from those used in the first embodiment. Further, for comparing new images of objects with images of the same objects which were photographed in the past by using optical systems producing distortion, the second embodiment is advantageous or preferable since it permits obtaining new images in the same photographing conditions as those for the images photographed in the past by adopting the abovementioned airspaces which are varied from those used in the first embodiment so as to modify the optical system into one which produces distortion. Furthermore, since the second embodiment permits obtaining a varied back focal length of the optical system by adopting varied values of $d_{40}$ and $d_{46}$, the optical system can be controlled so as to form an image on a light receiving surface of a TV set. Aberration characteristics of the second embodiment are visualized in FIGS. 18A to 18D.

The third embodiment has a composition similar to that of the first embodiment illustrated in FIG. 6A through FIG. 8D. In the third embodiment, however, aspherical surfaces which are adopted for favorably correcting aberrations, especially coma and curvature of field, are formed on the lens elements $L_1$ and $L_2$ shown in FIGS. 6A and 6B. Further, since the aspherical surface ASP which is formed on the lens element $L_2$ is located apart from the pupil, this aspherical surface serves for correction not only of coma and curvature of field but also of distortion. Aberration characteristics of the third embodiment are illustrated in FIGS. 19A to 19D.

The fourth embodiment has the same composition as that of the third embodiment, except for $d_{40}$, $d_{44}$ and $d_{46}$ which have values varied to 1.3460, 0.2130 and 1.3809 respectively as in the second embodiment so that distortion at the maximum image height is reduced to −14% from −5% in the third embodiment. Aberration characteristics of the fourth embodiment are visualized in FIGS. 20A to 20D.

The fifth embodiment has the same composition as that of the third embodiment and is configured so as to form, on a light receiving surface, images of objects located within a range of object distances from 4 mm to 2.13 mm by selecting $d_{40}$=1.1669 and $d_{46}$=1.5600. The fifth embodiment has the aberration characteristics illustrated in FIGS. 21A to 21D.

The sixth embodiment has the same composition as that of the first embodiment, except for a glass material which is selected for the lens element having the aspherical surface is different from that adopted for the first embodiment. This fact means that the endoscope according to the present invention permits selecting glass materials freely than the endoscopes which use aspherical surfaces in objective lens systems. In the sixth embodiment of the present invention, a glass material having a high refractive index is selected for the aspherical lens element. Aberration characteristics of the sixth embodiment are illustrated in FIGS. 22A to 22D.

The seventh embodiment has a composition which is similar to that of any one of the first embodiment through the sixth embodiment but is configured so as to be used with air, not water, as an object side medium. Aberration characteristics of the seventh embodiment are illustrated in FIGS. 23A to 23D.

Figure 10:
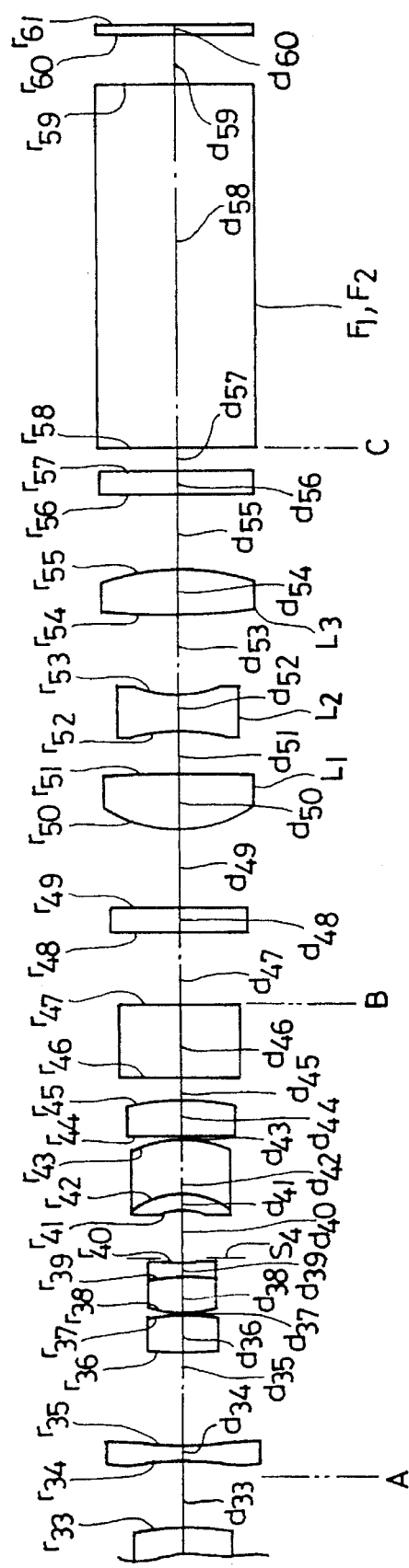
FIG. 10 shows a sectional view illustrating image relaying optical systems which are used in an eighth through a tenth embodiment of the endoscope according to the present invention.

The eighth embodiment has the same composition as that of the first embodiment, except for the image relaying optical systems which have the composition shown in FIG. 10 and an aspherical surface which is disposed on the object side of the image relaying optical system $R_4$. Aberration characteristics of the eighth embodiment are visualized in FIGS. 24A to 24D.

The ninth embodiment has the same composition as that of the eighth embodiment, and is configured so as to form images of objects located at farther object distances from 3.7 mm to 18.5 mm by adjusting $d_{49}$ and $d_{55}$ to 1.4882 and 0.8840 respectively. The parameters other than $d_{49}$ and $d_{55}$ are unchanged from those selected for the eighth embodiment. The ninth embodiment has the aberration characteristics visualized in FIGS. 25A to 25D.

The tenth embodiment has a composition which is similar to that of the eighth or ninth embodiment wherein an aspherical surface is disposed on the final surface $r_{32}$ of the image relaying optical system $R_3$ which is close to an image formed by the image relaying optical system $R_3$. Aberration characteristics of the tenth embodiment are illustrated in FIGS. 26A to 26D.

Figure 11:
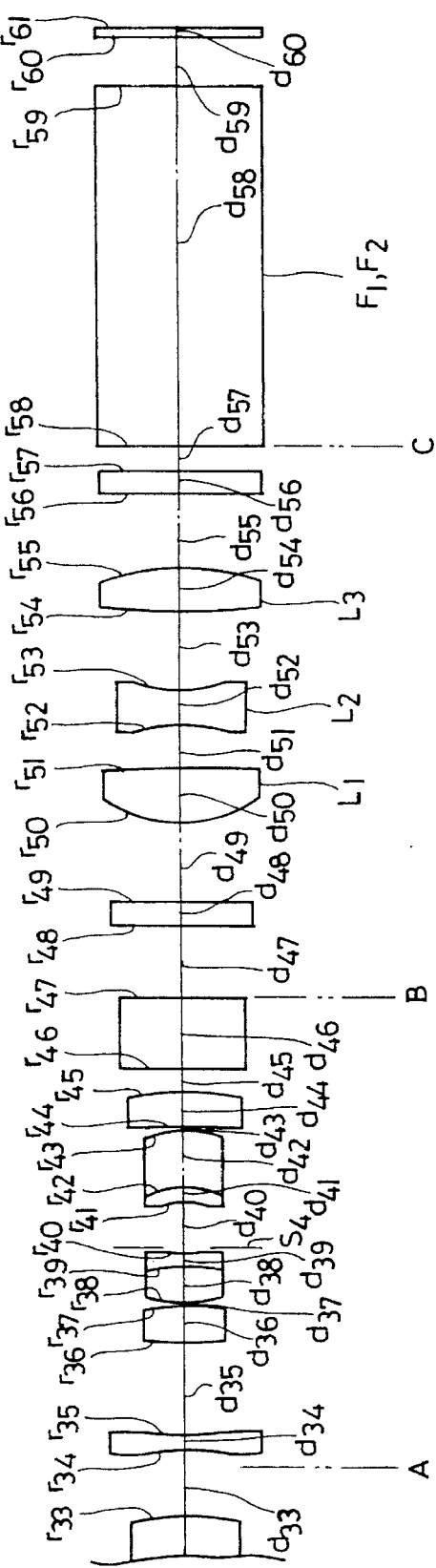
FIG. 11 shows a sectional view illustrating image relaying optical systems which are used in eleventh and twelfth embodiments of the endoscope according to the present invention.

The eleventh embodiment has the composition shown in FIG. 11 which is similar to that of the eighth embodiment, but is different from the eighth embodiment in that the eleventh embodiment is configured so as to used with an object side medium of air. Aberration characteristics of the tenth embodiment are illustrated in FIGS. 27A to 27D.

In the twelfth embodiment through the fourteenth embodiments, aspherical surfaces are disposed on both the sides of the pupil of the image relaying optical system $R_4$, i.e., on the side of the image relaying optical system $R_3$ and on the side of a light receiving side. Aberrations in air are corrected favorably even at wide angles, for example, 100° of the thirteenth embodiment, by producing a large amount of distortion with the aspherical surfaces disposed on both the sides of incidence and emergence.

Figure 12:
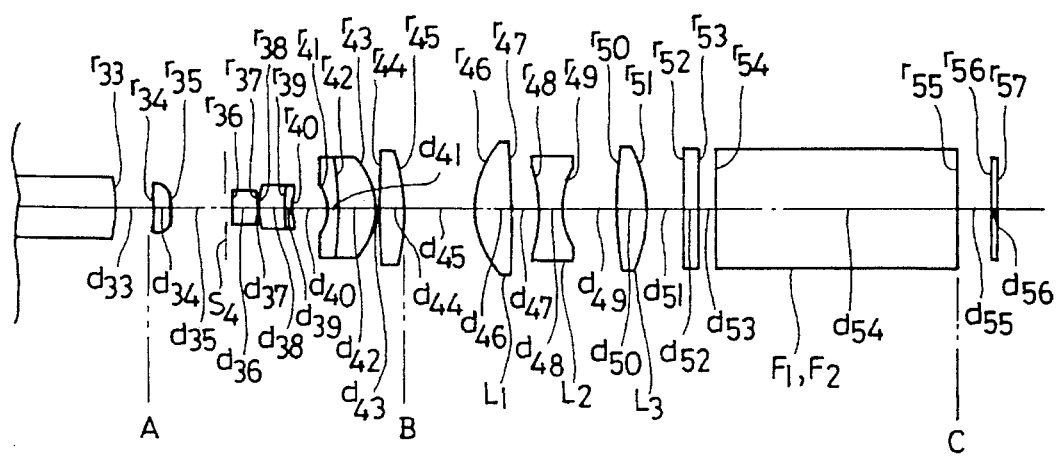
FIG. 12 shows a sectional view illustrating image relaying optical systems which are used in a thirteenth embodiment of the endoscope according to the present invention.
Figure 13:
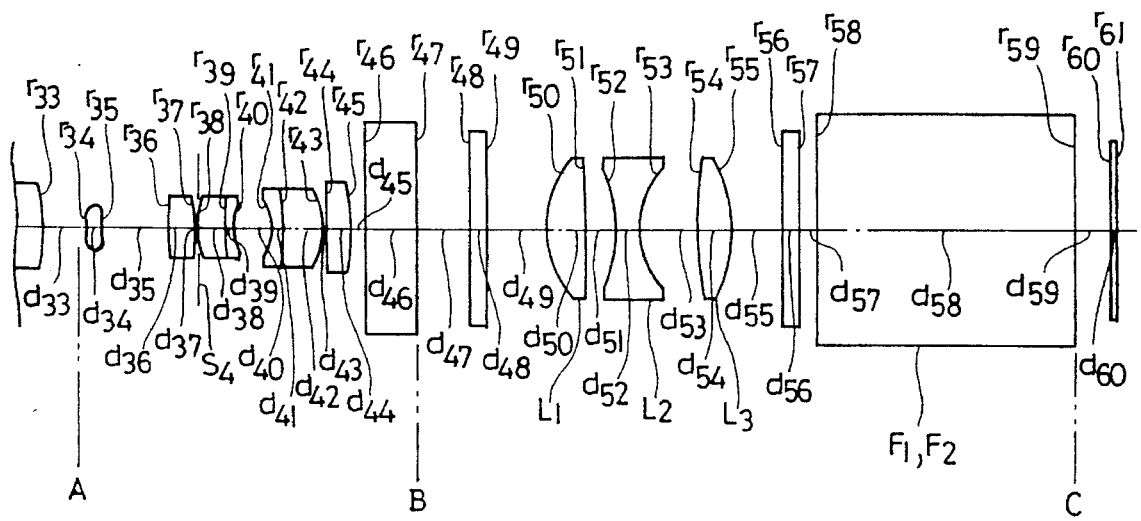
FIG. 13 shows a sectional view illustrating image relaying optical systems which are used in a fourteenth embodiment of the endoscope according to the present invention.

Out of these embodiments, the twelfth embodiment has a composition which is similar to that of the eleventh embodiment. Further, the thirteenth embodiment and the fourteenth embodiment adopt image relaying optical systems $R_4$ which have the compositions illustrated in FIG. 12 and FIG. 13 respectively. Aberration characteristics of the twelfth embodiment through the fourteenth embodiment are visualized in FIG. 28A through FIG. 30D respectively.

Each of the first embodiment through the fourteenth embodiment of the present invention described above is dividable at least one of the boundaries A, B and C for obtaining the effects which are described below:

When the endoscope is dividable at the boundary A, the image relaying optical system $R_4$ and a TV camera can be detached from the other sections, whereby the single image relaying optical system $R_4$ and the TV camera can be combined with an objective optical system and image relaying optical systems $R_1$, $R_2$, and $R_3$ which are different in lengths, thickness, etc.

When the endoscope is configured so as to be dividable at the boundary B, the divided section consisting of the objective optical system and the image relaying optical systems which are disposed on the object side of the boundary B can be used, like an ordinary endoscope equipped with an eyepiece lens system, for observing images by naked eyes.

Further, when the endoscope is configured so as to be dividable at the boundary C, the TV camera can be detached from the optical system comprising those from the objective optical system to the image relaying optical system $R_4$, whereby the TV camera can be exchanged, for example, with a camera having higher resolution or a still camera.

Figure 14:
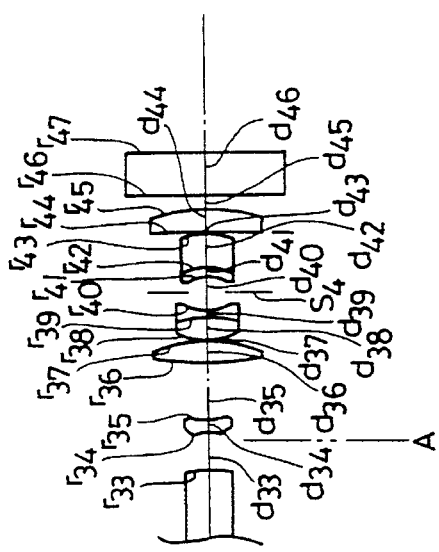
FIG. 14 shows a section view illustrating image relaying optical systems which are used in a fifteenth embodiment of the endoscope of the endoscope according to the present invention.

The fifteenth embodiment has the composition illustrated in FIG. 14 wherein the objective optical system 0 and the image relaying optical systems $R_1$, $R_2$ and $R_3$ have the compositions which are similar to those adopted for each of the embodiments already described above, but an eyepiece optical system E is disposed in place of the image relaying optical system $R_4$. An aspherical surface is disposed in the eyepiece optical system E for minimizing distortion in the endoscope as a whole by producing positive distortion. Aberration characteristics of the fifteenth embodiment are illustrated in FIGS. 31A to 31D. The fifteenth embodiment can be configured so as to be dividable at the boundary. A shown in FIG. 15 so that the eyepiece optical system E can be exchanged with other eyepiece optical systems having different magnifications and different distortion dependently on purpose of use of the endoscope.

The sixteenth embodiment has the composition shown in FIG. 15, and is configured so as to be dividable, like the fifteenth embodiment, at the boundary A shown in FIG. 15 and further at the boundary B. In the sixteenth embodiment, an eyepiece optical system E consists of a unit $E_1$ an another unit $E_2$, and an aspherical surface which produces positive distortion for correcting the negative distortion produced by the objective optical system is disposed in the unit $E_2$ located on the eye side of the boundary B. This aspherical surface satisfies the condition (10). Since the unit $E_2$ can be detached from the sixteenth embodiment and attached to the conventionally used ordinary endoscope, the sixteenth embodiment makes it possible to use the conventional ordinary endoscope as an endoscope having favorably corrected distortion by attaching the unit $E_2$ to such an endoscope. Further, when the eyepiece optical system of the sixteenth embodiment is disposed while corresponding the boundary B shown in FIG. 15 to the object point $O_4$ for the image relaying optical system $R_3$ in the first through fourteenth embodiments of the present invention, the endoscope can have a composition satisfying the abovementioned condition (6). Furthermore, when an optical path splitting prism is disposed in the airspace $d_{46}$ located on the image side of the aspherical surface in the unit $E_2$, a plurality of optical paths are available for permitting observation by a plurality of observers, whereby the sixteenth embodiment is usable as a lecture scope. Aberration characteristics of the sixteenth embodiment are visualized in FIGS. 32A to 32D.

Figure 34:
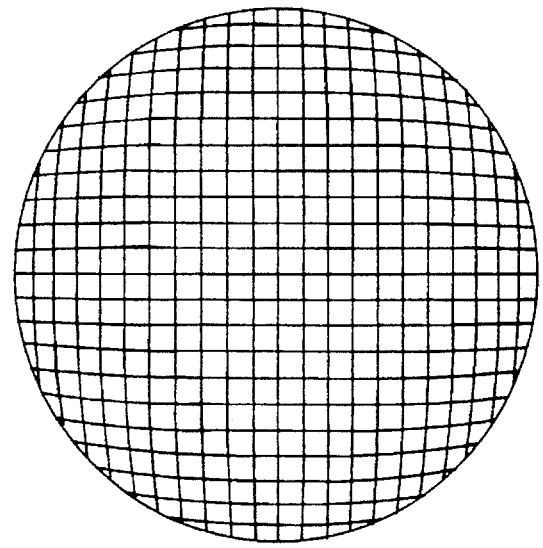
FIG. 34 through 36 shows illustrating appearances in water of images formed by the sixth embodiment, the fifteenth embodiment and the sixteenth embodiment respectively of the present invention.
Figure 35:
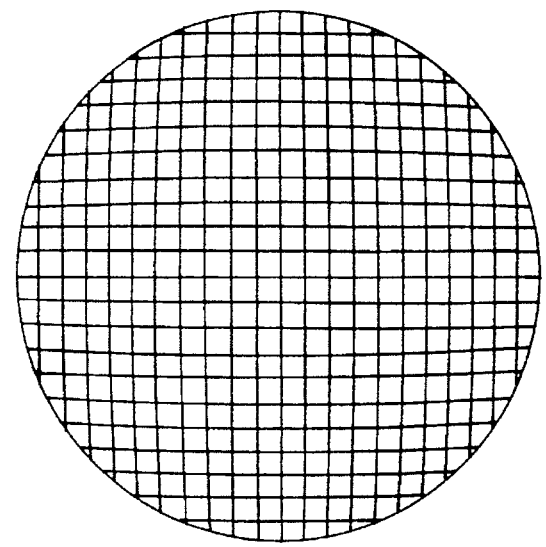
Figure 36:
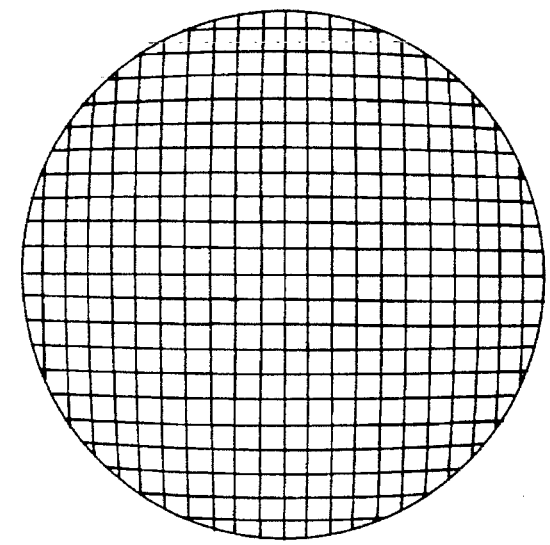

In addition, the sixth embodiment, the fifteenth embodiment and the eighteenth embodiment form images of a lattice-like object when the optical systems are located on an object side medium of a liquid as illustrated in FIG. 34, FIG. 35 and FIG. 36 respectively.

As is understood from the foregoing description, the endoscope according to the present invention uses an aberration correcting means such as an aspherical surface disposed in an image relaying optical system which is disposed near the image side and is capable of correcting aberrations, especially distortion, with no restrictions imposed on design or manufacturing of spherical lens elements, aspherical lens elements nor restrictions imposed on outside diameters or glass materials of the lens elements.

I claim:

1. An optical system for endoscopes comprising, in order from the object side:

an objective lens; and n image relaying lenses for relaying an image formed by said objective lens;

said objective lens and said image relaying lenses being disposed on a common optical axis;

said optical system comprising, in an (n−1)th one of said image relaying lenses, means for producing positive distortion cancelling negative distortion produced by said objective lens, said means for producing positive distortion being an aspherical surface and satisfying at least one of the following conditions (2) and (3):

(2) $|AS_{n-1}|L_{n-1} < 0.3$ (3) $|AS_{n-1}'|/L_{n-1} < 0.65$ wherein said reference symbol $AS_{n-1}$ represents a distance as measured from an image formed by an (n−2)th one of said image relaying lenses to said aspherical surface when said aspherical surface is located on an incidence side of a pupil of said (n−1)th one of said image relaying lenses, said reference symbol $AS_{n-1}'$ designates a distance as measured from an image formed by said (n−1)th one of said image relaying lenses to said aspherical surface when said aspherical surface is located on an emergence side of said pupil of said (n−1)th one of said image relaying lenses, said reference symbol $L_{n-1}$ denotes a distance defined by said image formed by said (n−2)th one of said image relaying lenses and said image formed by said (n−1)th one of said image relaying lenses, and n is greater than 2.

2. An optical system for endoscopes comprising, in order from the object side:

an objective lens; and n image relaying lenses for relaying an image formed by said objective lens;

said objective lens and said image relaying lenses being disposed on a common optical axis;

said optical system comprising, in an nth one of said image relaying lenses, means for producing positive distortion cancelling negative distortion produced by said objective lens, said means for producing positive distortion being an aspherical surface and satisfying at least one of the following conditions (6) and (7):

(6) $|AS_n|/L_n < 0.3$ (7) $|AS_n'|/L_n < 0.65$ wherein said reference symbol $AS_n$ represents a distance as measured from an image formed by said nth one of said image relaying lenses to said aspherical surface when said aspherical surface is located on an incidence side of a pupil of said nth one of said image relaying lenses, said reference symbol $AS_n'$ designates a distance as measured from an image formed by said nth one of said image relaying lenses to said aspherical surface, and said reference symbol $L_n$ denotes a distance defined by said image formed by said (n−1)th one of said image relaying lenses and said image formed by said nth one of said image relaying lenses, and n being greater than 2.

3. An optical system for endoscopes comprising, in order from the object side:

an objective lens; and n image relaying lenses for relaying an image formed by said objective lens;

said objective lens and said image relaying lenses being disposed on a common optical axis;

said optical system comprising, in an (n−1)th one of said image relaying lenses, means for producing positive distortion cancelling negative distortion produced by said objective lens, said means for producing positive distortion being an aspherical surface and satisfying at least one of the following conditions (4) and (5):

(4) $|AS_{n-1}|/L_{n-1}<0.65$
(5) $|AS_{n-1}'|/L_{n-1}<0.3$ wherein said reference symbol $AS_{n-1}$ represents a distance as measured from an image formed by an (n−2)th one of said image relaying lenses to said aspherical surface when said aspherical surface is located on an incidence side of a pupil of said (n−1)th one of said image relaying lenses, said reference symbol $AS_{n-1}'$ designates a distance as measured from an image formed by said (n−1)th one of said image relaying lenses to said aspherical surface when said aspherical surface is located on an emergence side of said pupil of said (n−1)th one of said image relaying lenses, said reference symbol $L_{n-1}$ denotes a distance defined by said image formed by said (n−2)th one of said image relaying lenses and said image formed by said (n−1)th one of said image relaying lenses, and n is greater than 2.

4. An optical system for endoscopes comprising, in order from the object side:

an objective lens; and n image relaying lenses for relaying an image formed by said objective lens;

said objective lens and said image relaying lenses being disposed on a common optical axis;

said optical system comprising, in an nth one of said image relaying lenses, means for producing positive distortion cancelling negative distortion produced by said objective lens, said means for producing positive distortion being an aspherical surface and satisfying at least one of the following conditions (8) and (9):

(8) $|AS_n|/L_n<0.65$
(9) $|AS_n'|/L_n<0.3$ wherein said reference symbol $AS_n$ represents a distance as measured from an image formed by said nth one of said image relaying lenses to said aspherical surface when said aspherical surface is located on an incidence side of a pupil of said nth one of said image relaying lenses, said reference symbol $AS_n'$ designates a distance as measured from an image formed by said nth one of said image relaying lenses to said aspherical surface, said reference symbol $L_n$ denotes a distance defined by said image formed by said (n−1)th one of said image relaying lenses and said image formed by said nth one of said image relaying lenses, and n is greater than 2.

5. An optical system according to one of claim 1, 2, 3 or 4, comprising an image pickup device for receiving an image formed by said nth image relaying lens.

6. An optical system according to one of claim 1, 2, 3 or 4, comprising an eyepiece for allowing observation of said formed image.

7. An optical system according to claim 6, wherein said means for producing positive distortion is an aspherical surface approximated by the following formula in which at least one of aspherical surface coefficients of fourth and higher orders has a positive value:

$$x = \frac{Cy^2}{1+\sqrt{1-C^2y^2}} + Ey^4 + Fy^6 + Gy^8 + Hy^{10}$$

wherein said reference symbols x and y represent coordinate values on a coordinate system wherein an optical axis is taken as an x axis taking a light receiving side of said optical system as positive, an intersection between said aspherical surface and said optical axis is taken as an origin, and a direction perpendicular to said x axis is taken as a y axis, said reference symbol C designates an inverse number of a radius of curvature of a sphere which is in contact with said aspherical surface on said optical axis, and said reference symbols E, F, G, and H denote aspherical surface coefficients of fourth, sixth, eighth, and tenth orders respectively.

8. An optical system according to one of claim 1 or 3, wherein said means for producing positive distortion is an aspherical surface approximated by the following formula in which at least one of aspherical surface coefficients of fourth and higher orders has a positive value:

$$x = \frac{Cy^2}{1+\sqrt{1-C^2y^2}} + Ey^4 + Fy^6 + Gy^8 + Hy^{10}$$

wherein said reference symbols x and y represent coordinate values on a coordinate system wherein an optical axis is taken as an x axis taking a light receiving side of said optical system as positive, an intersection between said aspherical surface and said optical axis is taken as an origin, and a direction perpendicular to said x axis is taken as a y axis, said reference symbol C designates an inverse number of a radius of curvature of a sphere which is in contact with said aspherical surface and said optical axis, and said reference symbols E, F, G, and H denote aspherical surface coefficients of fourth, sixth, eighth, and tenth orders respectively.

9. An optical system for endoscopes according to one of claim 1 or 3, wherein said image relaying lenses and said objective lens satisfy the following condition (1):

(1) $|DT_L/DT_0|>0.1$ wherein said reference symbol $DT_0$ represents a value of negative distortion at a maximum image height which is produced by said objective lens and said reference symbol $DT_L$ designates a value of positive distortion at a maximum image height which is produced by said image relaying lenses.

10. An optical system for endoscopes according to one of claim 1 or 3, further comprising:

an eyepiece for allowing observation of an image formed by said nth one of said image relaying lenses;

said image relaying lenses and said objective lens satisfying the following condition (1):

(1) $|DT_L/DT_0|>0.1$ wherein said reference symbol $DT_0$ represent a value of negative distortion at a maximum image height which is produced by said objective lens and said reference symbol $DT_L$ designates a value of positive distortion at a maximum image height which is produced by said image relaying lenses.

11. An optical system for endoscopes according to one of claim 2 or 4, wherein said image relaying lenses and said objective lens satisfy the following condition (1):

(1) $|DT_L/DT_0|>0.1$ wherein said reference symbol $DT_O$ represents a value of negative distortion at a maximum image height which is produced by said objective lens and said reference symbol $DT_L$ designates a value of positive distortion at a maximum image height which is produced by said image relaying lenses.

12. An optical system for endoscope according to one of claim 2 or 4, further comprising:

an eyepiece for allowing observation of an image formed by said nth one of said image relaying lenses; said image relaying lenses and said objective lens satisfying the following condition (1):

(1) $DT_L/|DT_O|>0.1$ wherein said reference symbol $DT_O$ represent a value of negative distortion at a maximum image height which is produced by said objective lens and said reference symbol $DT_L$ designates a value of positive distortion at a maximum image height which is produced by said image relaying lenses.

\* \* \* \* \*